US008987313B2

(12) United States Patent
Desai et al.

(10) Patent No.: US 8,987,313 B2
(45) Date of Patent: Mar. 24, 2015

(54) INHIBITORS OF CYTOCHROME P450

(75) Inventors: Manoj C. Desai, Pleasant Hill, CA (US);
Hon Chung Hui, San Mateo, CA (US);
Hongtao Liu, Cupertino, CA (US);
Jianyu Sun, Burnaby, CA (US);
Lianhong Xu, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/996,188

(22) PCT Filed: Dec. 20, 2011

(86) PCT No.: PCT/US2011/066250
§ 371 (c)(1),
(2), (4) Date: Jun. 20, 2013

(87) PCT Pub. No.: WO2012/088156
PCT Pub. Date: Jun. 28, 2012

(65) Prior Publication Data
US 2013/0309197 A1 Nov. 21, 2013

Related U.S. Application Data

(60) Provisional application No. 61/425,402, filed on Dec. 21, 2010.

(51) Int. Cl.
*A61K 31/426* (2006.01)
*A61K 31/497* (2006.01)
*A61K 31/445* (2006.01)
*A61K 31/535* (2006.01)
*C07D 417/14* (2006.01)
*A61K 31/427* (2006.01)
*A61K 31/437* (2006.01)
*A61K 31/454* (2006.01)
*A61K 31/496* (2006.01)
*A61K 31/5377* (2006.01)
*A61K 45/06* (2006.01)
*C07D 471/04* (2006.01)

(52) U.S. Cl.
CPC ............ *C07D 417/14* (2013.01); *A61K 31/427* (2013.01); *A61K 31/437* (2013.01); *A61K 31/454* (2013.01); *A61K 31/496* (2013.01); *A61K 31/5377* (2013.01); *A61K 45/06* (2013.01); *C07D 471/04* (2013.01)
USPC ................... 514/365; 514/236.8; 514/254.02; 514/303; 514/326

(58) Field of Classification Search
CPC . A61K 31/427; A61K 31/437; A61K 31/454; A61K 31/496; A61K 31/5377; A61K 45/06; C07D 417/14; C07D 471/04
USPC .................. 514/236.8, 254.02, 303, 326, 365
See application file for complete search history.

(56) References Cited

U.S. PATENT DOCUMENTS

| 8,088,770 | B2 * | 1/2012 | Desai et al. | 514/236.8 |
| 8,759,379 | B2 * | 6/2014 | Desai et al. | 514/365 |
| 2013/0274254 | A1 * | 10/2013 | Cannizzaro et al. | 514/232.2 |
| 2013/0280212 | A1 * | 10/2013 | Desai et al. | 424/85.4 |

FOREIGN PATENT DOCUMENTS

WO  WO-2008/103949 A1  8/2008

OTHER PUBLICATIONS

Ermolieff, J. et al. (Oct. 7, 1997). "Kinetic Properties of Saquinavir-Resistant Mutants of Human Immunodeficiency Virus Type 1 Protease and Their Implications in Drug Resistance in Vivo," *Biochemistry* 36(40)12364-12370.
International Search Report mailed on Feb. 28, 2012 for PCT Patent Application No. PCT/US2011/066250, filed on Dec. 20, 2011, three pages.
Kocienski, P.J. (May 1994). "Protecting Groups: An Overview," Chapter 1 in *Protecting Groups*, Thieme Publishing Group: New York, NY, pp. 1-20.
Kocienski, P.J. (May 1994). "Hydroxyl Protecting Groups," Chapter 2 in *Protecting Groups*, Thieme Publishing Group: New York, NY, pp. 21-94.
Kocienski, P.J. (May 1994). "Diol Protecting Groups," Chapter 3 in *Protecting Groups*, Thieme Publishing Group: New York, NY, pp. 95-117.
Kocienski, P.J. (May 1994). "Carboxyl Protecting Groups," Chapter 4 in *Protecting Groups*, Thieme Publishing Group: New York, NY, pp. 118-154.
Kocienski, P.J. (May 1994). "Carbonyl Protecting Groups," Chapter 5 in *Protecting Groups*, Thieme Publishing Group: New York, NY , pp. 155-184.

(Continued)

*Primary Examiner* — My-Chau T Tran
(74) *Attorney, Agent, or Firm* — Joel B. Silver

(57) ABSTRACT

The present application provides for a compound of formula I, or a salt thereof, compositions containing such compounds, therapeutic methods that include the administration of such compounds, and therapeutic methods that include the administration of such compounds with at least one additional therapeutic agent.

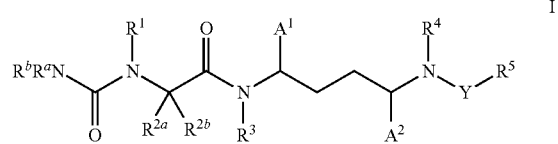

20 Claims, No Drawings

(56) References Cited

OTHER PUBLICATIONS

Kronbach, T. et al. (Jul. 1989). "Oxidation of Midazolam and Triazolam by Human Liver Cytochrome P450IIIA4," *Mol. Pharmacol.* 36(1):89-96.

Miners, J.O. et al. (Mar. 15, 1988). "Tolbutamide Hydroxylation by Human Liver Microsomes. Kinetic Characterisation and Relationship to Other Cytochrome P-450 Dependent Xenobiotic Oxidations," *Biochem. Pharmacol.* 37(6):1137-1144.

Toth, M.V. et al. (Dec. 1990). "A Simple, Continuous Fluorometric Assay for HIV Protease," *Int. J. Pert Protein Res.* 36(6):544-550.

Waxman, D.J. et al. (Jun. 1988). "Human Liver Microsomal Steroid Metabolism: Identification of the Major Microsomal Steroid Hormone 6 β-Hydroxylase Cytochrome P-450 Enzyme," *Arch. Biochem. Biophys.* 263(2):424-436.

Weislow, O.S. et al. (Apr. 19, 1989). "New Soluble-Formazan Assay for HIV-1 Cytopathic Effects: Application to High-Flux Screening of Synthetic and Natural Products for AIDS-Antiviral Activity," *J. Natl. Cancer Inst.* 81(8):577-586.

Written Opinion of the International Searching Authority mailed on Feb. 28, 2012 for PCT Patent Application No. PCT/US2011/066250, filed on Dec. 20, 2011, five pages.

* cited by examiner

INHIBITORS OF CYTOCHROME P450

PRIORITY OF INVENTION

This application is a National Phase filing under 35 U.S.C. §371 of International Application No. PCT/US2011/066250 having an international filing date of 20 Dec. 2011 which claims priority to U.S. Provisional Patent Application No. 61/425,402 filed 21 Dec. 2010. The entire contents of these applications are hereby incorporated herein by reference in their entirety.

FIELD OF THE INVENTION

This application relates generally to compounds and pharmaceutical compositions which improve the pharmacokinetics of a co-administered drug, and methods of improving, the pharmacokinetics of a drug by co-administration of the compounds with the drug.

BACKGROUND OF THE INVENTION

Oxidative metabolism by cytochrome P450 enzymes is one of the primary mechanisms of drug metabolism. It can be difficult to maintain therapeutically effective blood plasma levels of drugs which are rapidly metabolized by cytochrome P450 enzymes. Accordingly, the blood plasma levels of drugs which are susceptible to cytochrome P450 enzyme degradation can be maintained or enhanced by co-administration of cytochrome P450 inhibitors, thereby improving the pharmacokinetics of the drug.

While certain drugs are known to inhibit cytochrome P450 enzymes, more and/or improved inhibitors for cytochrome P450 monooxygenase are desirable. Particularly, it would be desirable to have cytochrome P450 monooxygenase inhibitors which do not have appreciable biological activity other than cytochrome P450 inhibition. Such inhibitors can be useful for minimizing undesirable biological activity (e.g., side effects). For example, it would be desirable to have P450 monooxygenase inhibitors that lack significant or have a reduced level of protease inhibitor activity. Such inhibitors could be useful for enhancing the effectiveness of antiretroviral drugs, while minimizing the possibility of eliciting viral resistance, especially against protease inhibitors.

SUMMARY OF THE INVENTION

One aspect of the present application is directed to compounds and pharmaceutical compositions which improve the pharmacokinetics of a co-administered drug. Representative examples of the invention also demonstrated little or no HIV protease inhibition activity. In one embodiment, the invention provides a compound which is a compound of formula I:

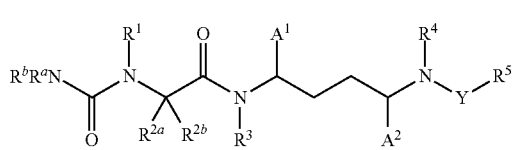

I wherein:
$A^1$ is $(C_1-C_6)$alkyl, aryl$(C_1-C_6)$alkyl, heteroaryl$(C_1-C_6)$alkyl, $(C_3-C_6)$carbocyclyl$(C_1-C_6)$alkyl or heterocyclyl$(C_1-C_6)$alkyl, wherein any $(C_1-C_6)$alkyl of $A^1$ is optionally substituted with one or more (e.g. 1, 2, 3, 4 or 5) $Z^2$ groups and wherein any aryl$(C_1-C_6)$alkyl, heteroaryl$(C_1-C_6)$alkyl, $(C_3-C_6)$carbocyclyl$(C_1-C_6)$alkyl or heterocyclyl$(C_1-C_6)$alkyl of $A^1$ is optionally substituted with one or more (e.g. 1, 2, 3, 4 or 5) $Z^3$ groups;

$A^2$ is $(C_1-C_6)$alkyl, aryl$(C_1-C_6)$alkyl, heteroaryl$(C_3-C_6)$alkyl, $(C_3-C_6)$carbocyclyl$(C_1-C_6)$alkyl or heterocyclyl$(C_1-C_6)$alkyl, wherein any $(C_1-C_6)$alkyl of $A^2$ is optionally substituted with one or more (e.g. 1, 2, 3, 4 or 5) $Z^2$ groups and wherein any aryl$(C_1-C_6)$alkyl, heteroaryl$(C_1-C_6)$alkyl, $(C_3-C_6)$carbocyclyl$(C_1-C_6)$alkyl or heterocyclyl$(C_1-C_6)$alkyl of $A^2$ is optionally substituted with one or more (e.g. 1, 2, 3, 4 or 5) $Z^3$ groups;

Y is —C(O)O— or —C(O)$NR^c$—;

$R^1$ is H or $(C_1-C_6)$alkyl, and $R^{2a}$ and $R^{2b}$ taken together with the carbon to which they are attached form a heterocyclyl or a carbocyclyl; or $R^{2b}$ is H, and $R^{2a}$ and $R^1$ taken together with the atoms to which they are attached form a heterocyclyl, wherein any heterocyclyl or carbocyclyl of $R^{2a}$ and $R^{2b}$ or $R^{2a}$ and $R^1$ is optionally substituted with one or more (e.g. 1, 2, 3, 4 or 5) $Z^1$ groups;

$R^3$ is H or $(C_1-C_6)$alkyl;
$R^4$ is H or $(C_1-C_6)$alkyl;
$R^5$ is aryl, aryl$(C_1-C_6)$alkyl, heteroaryl, heteroaryl$(C_1-C_6)$alkyl, heterocyclyl or heterocyclyl$(C_1-C_6)$alkyl, wherein any aryl, aryl$(C_1-C_6)$alkyl, heteroaryl, heteroaryl$(C_1-C_6)$alkyl, heterocyclyl or heterocyclyl$(C_1-C_6)$alkyl of $R^4$ is optionally substituted with one or more (e.g. 1, 2, 3, 4 or 5) $Z^4$ groups;

$R^a$ is H or $(C_1-C_6)$alkyl;
$R^b$ is heteroaryl$(C_1-C_6)$alkyl optionally substituted with one or more $Z^5$ groups;
$R^c$ is H or $(C_1-C_6)$alkyl;
each $R^d$ and $R^e$ is independently selected from H and $(C_1-C_6)$alkyl;
$R^f$ is H or $(C_1-C_6)$alkyl;
$R^g$ is $(C_1-C_6)$alkyl;
each $Z^1$ is independently selected from halogen, OH, —$CF_3$, —$OCF_3$, oxo, CN, $(C_1-C_6)$alkyl, —$O(C_1-C_6)$alkyl, —$S(C_1-C_6)$alkyl, —$SO(C_1-C_6)$alkyl, —$SO_2(C_1-C_6)$alkyl, —$NR^dR^e$—$NR^fC(O)R^g$, —$NR^fS(O)_2R^g$, heterocyclyl and heteroaryl;

each $Z^2$ is independently selected from OH, oxo, halogen, —$OCF_3$, CN, —$O(C_1-C_6)$alkyl, —$S(C_1-C_6)$alkyl, —$SO(C_1-C_6)$alkyl, —$SO_2(C_1-C_6)$alkyl, —$NR^dR^e$, —$NR^fC(O)R^g$ and —$NR^fS(O)_2R^g$;

each $Z^3$ is independently selected from OH, oxo, halogen, —$CF_3$, —$OCF_3$, $NO_2$, CN, $(C_1-C_6)$alkyl, —$O(C_1-C_6)$alkyl, —$S(C_1-C_6)$alkyl, —$SO(C_1-C_6)$alkyl, —$SO_2(C_1-C_6)$alkyl, —$NR^dR^e$, —$NR^fC(O)R^g$ and —$NR^fS(O)_2R^g$;

each $Z^4$ is independently selected from OH, oxo, halogen, —$CF_3$, —$OCF_3$, —$NO_2$, —CN, $(C_1-C_6)$alkyl, —$O(C_1-C_6)$alkyl, and —$NR^dR^e$; and each $Z^5$ is independently selected from OH, oxo, halogen, —$CF_3$, —$OCF_3$, —$NO_2$, —CN, $(C_1-C_6)$alkyl, —$O(C_1-C_6)$alkyl, and —$NR^dR^e$;

or a salt thereof.

In another embodiment, the invention provides a pharmaceutical composition comprising a compound of formula I, or a pharmaceutically acceptable salt thereof and a pharmaceutically acceptable carrier or excipient.

In another embodiment, the invention provides a pharmaceutical composition comprising: 1) a compound of formula I or pharmaceutically acceptable salt thereof, 2) one or more (e.g. 1, 2, 3 or 4) therapeutic agents, and 3) a pharmaceutically acceptable carrier or excipient.

In another embodiment, the invention provides a method for improving the pharmacokinetics of a therapeutic agent, comprising co-administration to a patient the therapeutic agent and a compound of formula I or a pharmaceutically acceptable salt thereof.

In another embodiment, the invention provides a method for increasing the blood plasma levels of a therapeutic agent, comprising co-administration to a patient the therapeutic agent and a compound of formula I or a pharmaceutically acceptable salt thereof.

In another embodiment, the invention provides a method for inhibiting cytochrome P450 monooxygenase in a patient comprising administering to a patient in need thereof an amount of a compound of formula I, or a pharmaceutically acceptable salt thereof, effective to inhibit cytochrome P450 monooxygenase.

In another embodiment, the invention provides a method for treating a viral infection, (e.g., HIV, HCV) comprising co-administration to a patient in need thereof a therapeutically effective amount of a compound of formula I, or a pharmaceutically acceptable salt thereof, in combination with a therapeutically effective amount of, one or more (e.g. 1, 2, 3, and 4) therapeutic agents which are metabolized by cytochrome P450 monooxygenase, and which are suitable for treating a viral infection (e.g., HIV, HCV).

In another embodiment, the invention provides a combination pharmaceutical agent comprising:

a) a first pharmaceutical composition comprising a compound of formula I, or a pharmaceutically acceptable salt thereof; and b) a second pharmaceutical composition comprising at least one therapeutically active agent which is metabolized by cytochrome P450 monooxygenase.

In another embodiment, the invention provides a combination pharmaceutical agent comprising:

a) a compound of formula I, or a pharmaceutically acceptable salt thereof; and b) at least one therapeutically active agent which is metabolized by cytochrome P450 monooxygenase.

In another embodiment the invention provides a compound of formula I, or a pharmaceutically acceptable salt thereof for use in medical therapy.

In another embodiment the invention provides the use of a compound of formula I, or a pharmaceutically acceptable salt thereof for the manufacture of a medicament useful for improving the pharmacokinetics of a therapeutic agent which is metabolized by cytochrome P450 monooxygenase in a patient.

In another embodiment the invention provides the use of a compound of formula I, or a pharmaceutically acceptable salt thereof for the manufacture of a medicament useful for increasing the blood plasma levels of a therapeutic agent which is metabolized by cytochrome P450 monooxygenase in a patient.

In another embodiment, the invention provides the use of a compound of formula I, or a pharmaceutically acceptable salt thereof for the manufacture of a medicament useful for inhibiting cytochrome P450 monooxygenase in a patient.

In another embodiment the invention provides the use of a compound of formula I or a pharmaceutically acceptable salt thereof, in combination with one or more (e.g. 1, 2, 3 or 4) therapeutic agents (e.g. agents with anti-HIV or anti-HCV properties) for the manufacture of a medicament useful for treating a viral infection (e.g., HIV, HCV).

In another embodiment the invention provides a compound of formula I or a pharmaceutically acceptable salt thereof, in combination with one or more (e.g. 1, 2, 3 or 4) therapeutic agents (e.g. agents with anti-HIV or anti-HCV properties) for the prophylactic or therapeutic treatment of a viral infection (e.g., HIV, HCV) in a patient.

In another embodiment the invention provides processes and intermediates disclosed herein that are useful for preparing compounds of formula I or salts thereof.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

Unless otherwise indicated, all documents, patents, and patent applications referenced herein are incorporated by reference in their entirety for all purposes.

DEFINITIONS

Unless stated otherwise, the following terms and phrases as used herein are intended to have the following meanings:

When trade names are used herein, applicants intend to independently include the tradename product and the active pharmaceutical ingredient(s) of the tradename product.

The term "alkyl" as used herein refers to a hydrocarbon containing normal, secondary or tertiary atoms. For example, an alkyl group can have 1 to 20 carbon atoms (i.e., $C_1$-$C_{20}$ alkyl), 1 to 10 carbon atoms (i.e., $C_1$-$C_{10}$ alkyl), 1 to 8 carbon atoms (i.e., $C_1$-$C_8$ alkyl) or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

The term "halogen" as used herein refers to fluoro, chloro, bromo and iodo.

The term "aryl" as used herein refers to a single aromatic ring or a bicyclic or multicyclic ring as described in the following definition. For example, an aryl group can have 6 to 20 carbon atoms, 6 to 14 carbon atoms, or 6 to 12 carbon atoms. Aryl includes a phenyl radical or an ortho-fused bicyclic or multicyclic radical having about 9 to 14 atoms in which at least one ring is aromatic (e.g. an aryl fused to one or more aryls or carbocycles). Such bicyclic or multicyclic rings may be optionally substituted with one or more (e.g. 1, 2 or 3) oxo groups on any carbocycle portion of the condensed ring. It is to be understood that the point of attachment of a bicyclic or multicyclic radical, as defined above, can be at any position of the ring including an aryl or a carbocycle portion of the ring. Typical aryl groups include, but are not limited to, phenyl, indenyl, naphthyl, 1,2,3,4-tetrahydronaphthyl, anthracenyl, and the like.

The term "arylalkyl" as used herein refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl ($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring or a multiple condensed ring as described in the following definition. The term "heteroaryl" includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term heteroaryl also includes multiple condensed ring systems (e.g. ring systems comprising 2 or 3 rings) wherein a heteroaryl group (as defined above) can be fused with one or more heteroaryls (e.g. naphthyridinyl), carbocycles (e.g. 5,6,7,8-tetrahydroquinolyl) or aryls (e.g. indazolyl) to form a multiple condensed ring. Such multiple condensed rings may be optionally substituted with one or more (e.g. 1, 2 or 3) oxo groups on the cycloalkyl portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, thiophenyl, imidazolyl, oxazolyl, thiazolyl, furyl, oxadiazolyl, thiadiazolyl, quinolyl, isoquinolyl, benzothiazolyl, benzoxazolyl, indazolyl, indolyl, quinoxalyl, quinazolyl, 5,6,7,8-tetrahydroisoquinolinyl and 4,5,6,7-tetrahydroindolyl.

The term "heterocyclyl" or "heterocycle" as used herein refers to a single saturated or partially unsaturated ring or a multiple condensed ring as described in the following definition. The term "heterocyclyl" or "heterocycle" includes single saturated or partially unsaturated rings (e.g. 3, 4, 5, 6, 7 or 8-membered ring) from about 1 to 7 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term heterocycle also includes multiple condensed ring systems (e.g. ring systems comprising 2 or 3 rings) wherein a heterocycle group (as defined above) can be fused with one or more heterocycles (e.g. decahydronapthyridinyl), heteroaryls (e.g. 1,2,3,4-tetrahydronaphthyridinyl), carbocycles (e.g. decahydroquinolyl) or aryls (e.g. 1,2,3,4-tetrahydroisoquinolyl) to form a multiple condensed ring. It is to be understood that the point of attachment of a heterocycle multiple condensed ring, as defined above, can be at any position of the ring including a heterocycle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, tetrahydrothiophenyl, dihydrooxazolyl, tetrahydropyranyl, tetrahydrothiopyranyl, 1,2,3,4-tetrahydroquinolyl, benzoxazinyl dihydrooxazolyl, thiazolidinyl, S,S-dioxothiazolidinyl and 4,5,6,7-tetrahydro-3H-imidazo[4,5-c]pyridinyl.

The term "heteroarylalkyl" as used herein refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e. heteroaryl($C_1$-$C_6$)alkyl). Heteroarylalkyl groups include, but are not limited to heteroaryl-$CH_2$—, heteroaryl-$CH(CH_3)$—, heteroaryl-$CH_2CH_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

The term "heterocyclylalkyl" as used herein refers to an alkyl radical as defined herein in which one of the hydrogen atoms bonded to a carbon atom is replaced with a heterocyclyl radical as described herein (i.e., a heterocyclyl-alkyl-moiety). The alkyl group of the "heterocyclylalkyl" is typically 1 to 6 carbon atoms (i.e. heterocyclyl($C_1$-$C_6$)alkyl). Typical heterocyclylalkyl groups include, but are not limited to heterocyclyl-$CH_2$—, heterocyclyl-$CH(CH_3)$—, heterocyclyl-$CH_2CH_2$—, 2-(heterocyclyl)ethan-1-yl, and the like, wherein the "heterocyclyl" portion includes any of the heterocyclyl groups described above. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Examples of heterocyclylalkyls include by way of example and not limitation 5-membered sulfur, oxygen, and/or nitrogen containing heterocycles such tetrahydrofuranylmethyl and pyrroldinylmethyl, etc., and 6-membered sulfur, oxygen, and/or nitrogen containing heterocycles such as piperidinylmethyl, piperazinylmethyl, morpholinylmethyl, etc.

The term "carbocycle" or "carbocyclyl" as used herein refers to a saturated (i.e., cycloalkyl) or partially unsaturated (e.g., cycloalkenyl, cycloalkadienyl, etc.) ring having 3 to 7 carbon atoms as a monocycle, 7 to 12 carbon atoms as a bicycle, and up to about 20 carbon atoms as a polycycle. Monocyclic carbocycles can also have 3 to 6 ring atoms (i.e. ($C_3$-$C_6$)carbocyclyl) as well as 5 to 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. The "carbocycle" or "carbocyclyl" may be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "carbocyclylalkyl" as used herein refers to an alkyl radical as defined herein in which one of the hydrogen atoms bonded to a carbon atom is replaced with a carbocyclyl radical as described herein (i.e., a carbocyclyl-alkyl-moiety). The alkyl group of the "carbocyclylalkyl" is typically 1 to 6 carbon atoms (i.e. carbocyclyl($C_1$-$C_6$)alkyl). Typical carbocyclyl alkyl groups include, but are not limited to carbocyclyl-$CH_2$—, carbocyclyl-$CH(CH_3)$—, carbocyclyl-$CH_2CH_2$—, 2-(carbocyclyl)ethan-1-yl, and the like, wherein the "carbocyclyl" portion includes any of the carbocyclyl groups described above.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The modifier "about" used in connection with a quantity is inclusive of the stated value and has the meaning dictated by the context (e.g., includes the degree of error associated with measurement of the particular quantity).

Protecting Groups

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG groups. In general, PG groups will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like. Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Stereoisomers

The term "stereoisomers" refers to compounds which have identical chemical constitution, but differ with regard to the arrangement of the atoms or groups in space (e.g. diastereomers and enantiomers).

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

One skilled in the art will recognize that stereoisomers or mixtures of stereoisomers of the compounds of the invention include enantiomers, diastereomers and other stereoisomers. For example, for a compound of formula I with the following structure:

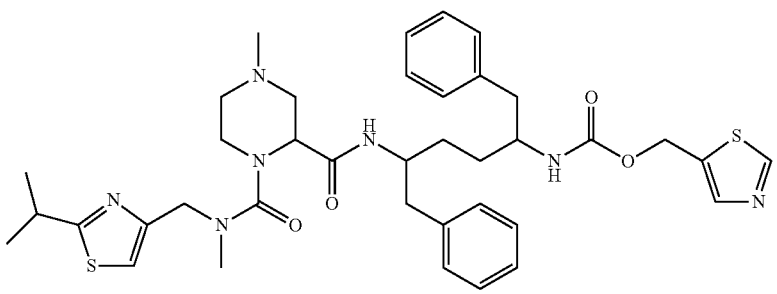 [SMILES: CC(C)c1nc(CN(C)C(=O)N2CCN(C)CC2C(=O)NC(CCC(Cc2ccccc2)NC(=O)OCc2cncs2)Cc2ccccc2)cs1]

contemplated stereoisomers include at least:
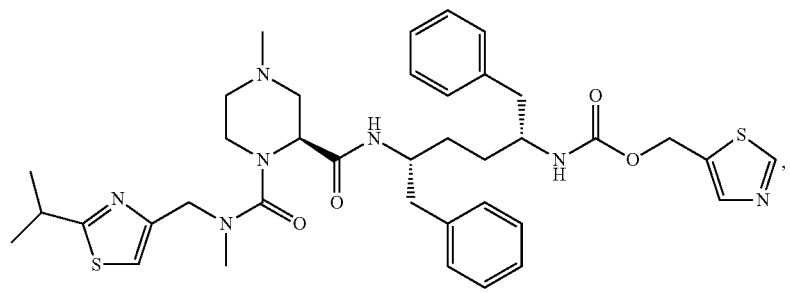
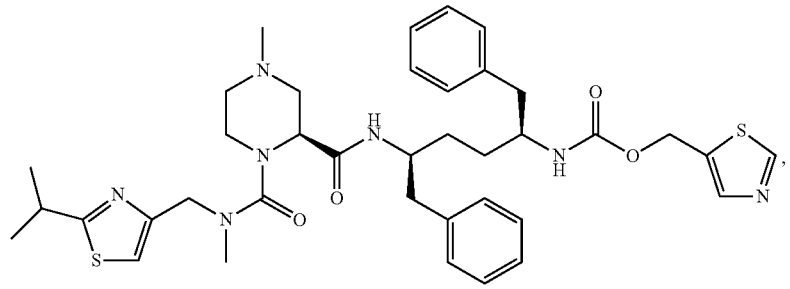
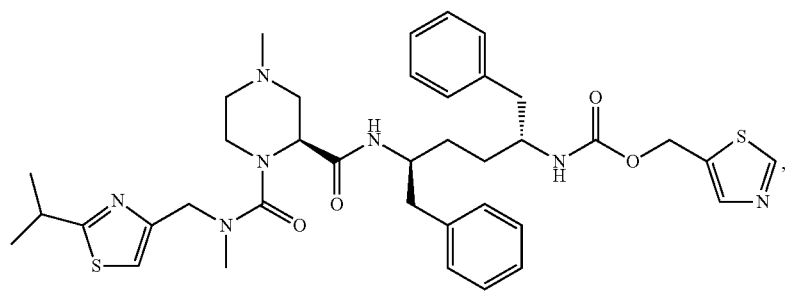
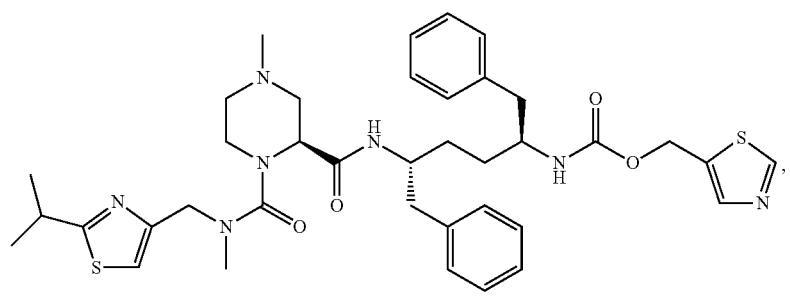
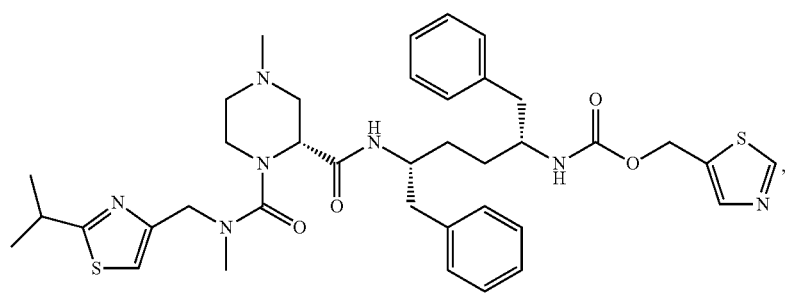

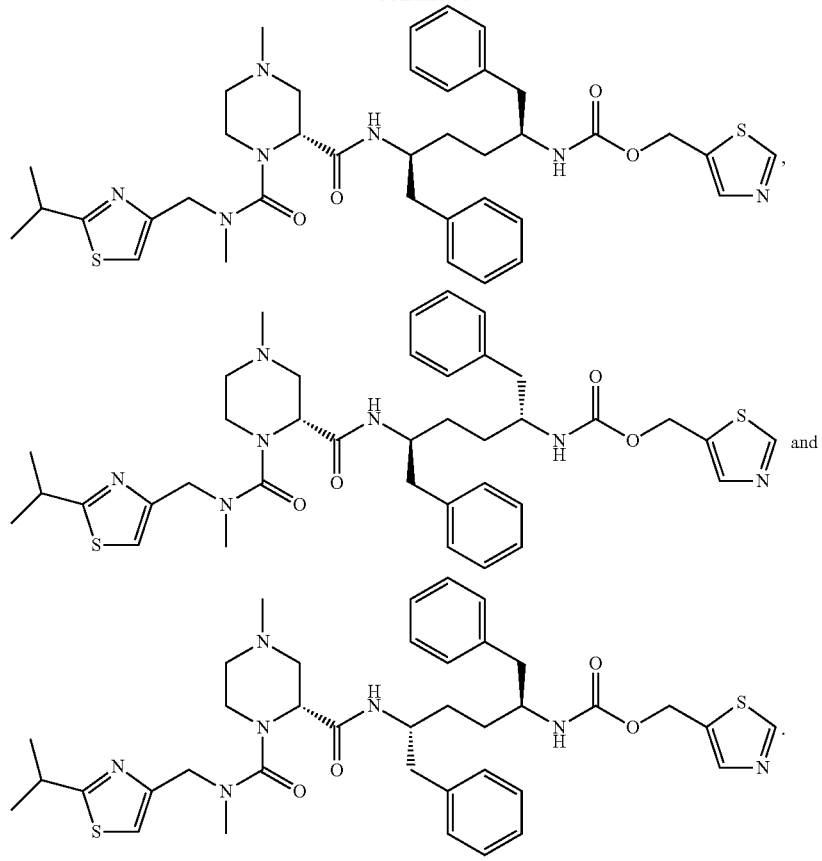

as well as mixtures of two or more of these stereoisomers. Thus, it is to be understood that when a bond is drawn in a non-stereochemical manner (e.g. flat) for a compound of the invention, the atom to which the bond is attached includes all stereochemical possibilities.

It is also to be understood that when a bond is drawn in a defined stereochemical manner (e.g. bold, bold-wedge, dashed or dashed-wedge), the atom to which the stereochemical bond is attached has the stereochemistry as shown unless otherwise noted. Thus, for a compound of the following formula:

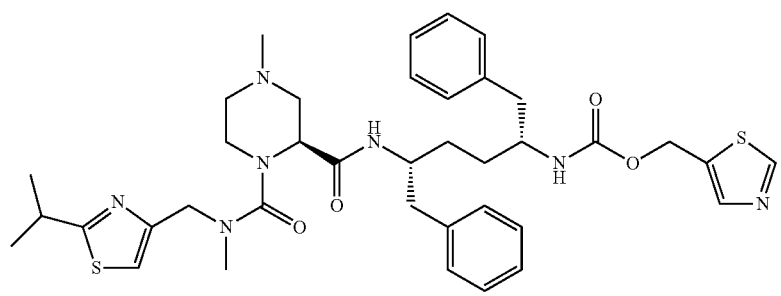 [SMILES: CC(C)c1nc(CN(C)C(=O)N2CCN(C)C[C@H]2C(=O)N[C@H](CC[C@H](Cc2ccccc2)NC(=O)OCc2cncs2)Cc2ccccc2)cs1]

the stereochemistry of the compound of the formula is as shown.

Compounds of Formula I

In one embodiment of the compounds of formula I, $R^1$ is H or $(C_1-C_6)$alkyl, and $R^{2a}$ and $R^{2b}$ taken together with the carbon to which they are attached form a heterocyclyl or a carbocyclyl, wherein any heterocyclyl or carbocyclyl of $R^{2a}$ and $R^{2b}$ is optionally substituted with one or more $Z^1$ groups.

In another embodiment of the compounds of formula I, $R^1$ is H and $R^{2a}$ and $R^{2b}$ taken together with the carbon to which they are attached form a heterocyclyl or a carbocyclyl, wherein any heterocyclyl or carbocyclyl of $R^{2a}$ and $R^{2b}$ is optionally substituted with one or more $Z^1$ groups.

In another embodiment of the compounds of formula I, $R^1$ is $CH_3$, and $R^{2a}$ and $R^{2b}$ taken together with the carbon to which they are attached form a heterocyclyl or a carbocyclyl, wherein any heterocyclyl or carbocyclyl of $R^{2a}$ and $R^{2b}$ is optionally substituted with one or more $Z^1$ groups.

In another embodiment of the compounds of formula I, $R^1$ is H or $(C_1-C_6)$alkyl, and $R^{2a}$ and $R^{2b}$ taken together with the carbon to which they are attached form a heterocyclyl, wherein any heterocyclyl of $R^{2a}$ and $R^{2b}$ is optionally substituted with one or more $Z^1$ groups.

In another embodiment of the compounds of formula I, $R^1$ is H, and $R^{2a}$ and $R^{2b}$ taken together with the carbon to which they are attached form a heterocyclyl, wherein any heterocyclyl of $R^{2a}$ and $R^{2b}$ is optionally substituted with one or more $Z^1$ groups.

In another embodiment of the compounds of formula I, $R^1$ is $CH_3$, and $R^{2a}$ and $R^{2b}$ together with the carbon to which they are attached form a heterocyclyl, wherein any heterocyclyl of $R^{2a}$ and $R^{2b}$ is optionally substituted with one or more $Z^1$ groups.

In another embodiment of the compounds of formula I, $R^1$ is H or $(C_1-C_6)$alkyl, and $R^{2a}$ and $R^{2b}$ taken together with the carbon to which they are attached form a piperidinyl, wherein the piperidinyl is optionally substituted with one or more $Z^1$ groups.

In another embodiment of the compounds of formula I, $R^1$ is H, and $R^{2a}$ and $R^{2b}$ taken together with the carbon to which they are attached form a piperidinyl, wherein the piperidinyl is optionally substituted with one or more $Z^1$ groups.

In another embodiment of the compounds of formula I, $R^1$ is $CH_3$, and $R^{2a}$ and $R^{2b}$ taken together with the carbon to which they are attached form a piperidinyl, wherein the piperidinyl is optionally substituted with one or more $Z^1$ groups.

In another embodiment of the compounds of formula I, $R^1$ is H or $(C_1-C_6)$alkyl, and $R^{2a}$ and $R^{2b}$ together with the carbon to which they are attached form a 1-methylpiperidinyl.

In another embodiment of the compounds of formula I, $R^1$ is H, and $R^{2a}$ and $R^{2b}$ together with the carbon to which they are attached form a 1-methylpiperidinyl.

In another embodiment of the compounds of formula I, $R^1$ is $CH_3$, and $R^{2a}$ and $R^{2b}$ together with the carbon to which they are attached form a 1-methylpiperidinyl.

In one embodiment of the compounds of formula I, $R^{2b}$ is H, and $R^{2a}$ and $R^1$ together with the atoms to which they are attached form a heterocyclyl, wherein any heterocyclyl of $R^{2a}$ and $R^1$ is optionally substituted with one or more $Z^1$ groups.

In another embodiment of the compounds of formula I, $R^{2b}$ is H, and $R^{2a}$ and $R^1$ taken together with the atoms to which they are attached form a piperazinyl, pyrrolidinyl, thiazolidinyl, S,S-dioxo-thiazolidinyl or 4,5,6,7-tetrahydro-3H-imidazo[4,5-c]pyridinyl, each of which is optionally substituted with one or more $Z^1$ groups.

In another embodiment of the compounds of formula I, $R^{2b}$ is H, and $R^{2a}$ and $R^1$ taken together with the atoms to which they are attached form a piperazinyl, 1-methylpiperazinyl, hydroxypyrrolidinyl, N—N-dimethylaminopyrrolidinyl, N-methylaminopyrrolidinyl, aminopyrrolidinyl, morpholinopyrrolidinyl, acetylaminopyrrolidinyl, pyrrolidinyl, thiazolidinyl, S,S-dioxo-thiazolidinyl or 4,5,6,7-tetrahydro-3H-imidazo[4,5-c]pyridinyl.

In one embodiment of the compounds of formula I, $Z^1$ is OH, oxo, $(C_1-C_6)$alkyl, $—NR^dR^e$, $NR^fC(O)R^g$ or heterocyclyl.

In one embodiment of the compounds of formula I, $R^d$ and $R^e$ are each independently H or $(C_1-C_6)$alkyl.

In another embodiment of the compounds of formula I, $R^d$ and $R^e$ are each independently H or $—CH_3$.

In another embodiment of the compounds of formula I, $R^d$ and $R^e$ are each H.

In another embodiment of the compounds of formula I, $R^d$ and $R^e$ are each $—CH_3$.

In another embodiment of the compounds of formula I, $Z^1$ is piperidine, morpholine, piperazine, N-methylpiperazine or pyrrolidine.

In another embodiment of the compounds of formula I, $Z^1$ is morpholine.

In one embodiment of the compounds of formula I, $R^f$ is H or $(C_1-C_6)$alkyl.

In another embodiment of the compounds of formula I, $R^g$ is H.

In one embodiment of the compounds of formula I, $R^g$ is $(C_1-C_6)$alkyl.

In another embodiment of the compounds of formula I, $R^g$ is $—CH_3$.

In another embodiment of the compounds of formula I, $Z^1$ is OH, $—CH_3$, $—NH_2$, $—N(CH_3)_2$, $—NHCH_3$, $—NHC(O)CH_3$ or morpholine.

In one embodiment of the compounds of formula I, $R^a$ is H or $(C_1-C_6)$alkyl.

In another embodiment of the compounds of formula I, $R^a$ is $(C_1-C_6)$alkyl.

In another embodiment of the compounds of formula I, $R^a$ is $—CH_3$.

In one embodiment of the compounds of formula I, $R^b$ is heteroaryl-$CH_2$—, wherein heteroaryl-$CH_2$— is optionally substituted with one or more $Z^5$ groups.

In another embodiment of the compounds of formula I, $R^b$ is a thiazol-4-ylmethyl, wherein the thiazol-4-ylmethyl is optionally substituted with one or more $Z^5$ groups.

In another embodiment of the compounds of formula I, $R^b$ is thiazolylmethyl substituted with $(C_1-C_6)$alkyl.

In another embodiment of the compounds of formula I, $R^b$ is 2-isopropylthiazol-4-ylmethyl.

In one embodiment of the compounds of formula I, Y is $—C(O)NR^c—$.

In one embodiment of the compounds of formula I, $R^c$ is H.

In another embodiment of the compounds of formula I, $R^c$ is methyl.

In one embodiment of the compounds of formula I, Y is $—C(O)O—$.

In one embodiment of the compounds of formula I, $R^3$ is H.

In another embodiment of the compounds of formula I, $R^3$ is $(C_1-C_6)$alkyl.

In another embodiment of the compounds of formula I, $R^3$ is methyl.

In one embodiment of the compounds of formula I, $R^4$ is H.

In another embodiment of the compounds of formula I, $R^4$ is $(C_1-C_6)$alkyl.

In another embodiment of the compounds of formula I, $R^4$ is methyl.

In one embodiment of the compounds of formula I, $R^5$ is heteroaryl$(C_1-C_6)$alkyl, wherein any heteroaryl$(C_1-C_6)$alkyl of $R^5$ is optionally substituted with one or more $Z^6$ groups.

In another embodiment of the compounds of formula I, $R^5$ is heteroaryl-$CH_2$—, wherein any heteroaryl-$CH_2$— of $R^5$ is optionally substituted with one or more $Z^6$ groups.

In another embodiment of the compounds of formula I, $R^5$ is heteroaryl$(C_1-C_6)$alkyl.

In another embodiment of the compounds of formula I, $R^5$ is heteroaryl-$CH_2$—.

In another embodiment of the compounds of formula I, $R^5$ is thiazolomethyl.

In another embodiment of the compounds of formula I, $R^5$ is thiazol-5-ylmethyl.

In one embodiment of the compounds of formula I, $A^1$ is aryl$(C_1-C_6)$alkyl, wherein any aryl$(C_1-C_6)$alkyl of $A^1$ is optionally substituted with one or more $Z^3$ groups.

In another embodiment of the compounds of formula I, $A^1$ is phenyl($C_1$-$C_6$)alkyl, wherein any phenyl($C_1$-$C_6$)alkyl of $A^1$ is optionally substituted with one or more $Z^3$ groups.

In another embodiment of the compounds of formula I, $A^1$ is phenylCH$_2$—, wherein any phenylCH$_2$— of $A^1$ is optionally substituted with one or more $Z^3$ groups.

In another embodiment of the compounds of formula I, $A^1$ is phenylCH$_2$—.

In one embodiment of the compounds of formula I, $A^2$ is aryl($C_1$-$C_6$)alkyl, wherein any aryl($C_1$-$C_6$)alkyl of $A^2$ is optionally substituted with one or more $Z^3$ groups.

In another embodiment of the compounds of formula I, $A^2$ is phenyl($C_1$-$C_6$)alkyl, wherein any phenyl($C_1$-$C_6$)alkyl of $A^2$ is optionally substituted with one or more $Z^3$ groups.

In another embodiment of the compounds of formula I, $A^2$ is phenylCH$_2$—, wherein any phenylCH$_2$— of $A^2$ is optionally substituted with one or more $Z^3$ groups.

In another embodiment of the compounds of formula I, $A^2$ is phenylCH$_2$—.

In one embodiment the invention provides a compound of formula I selected from:

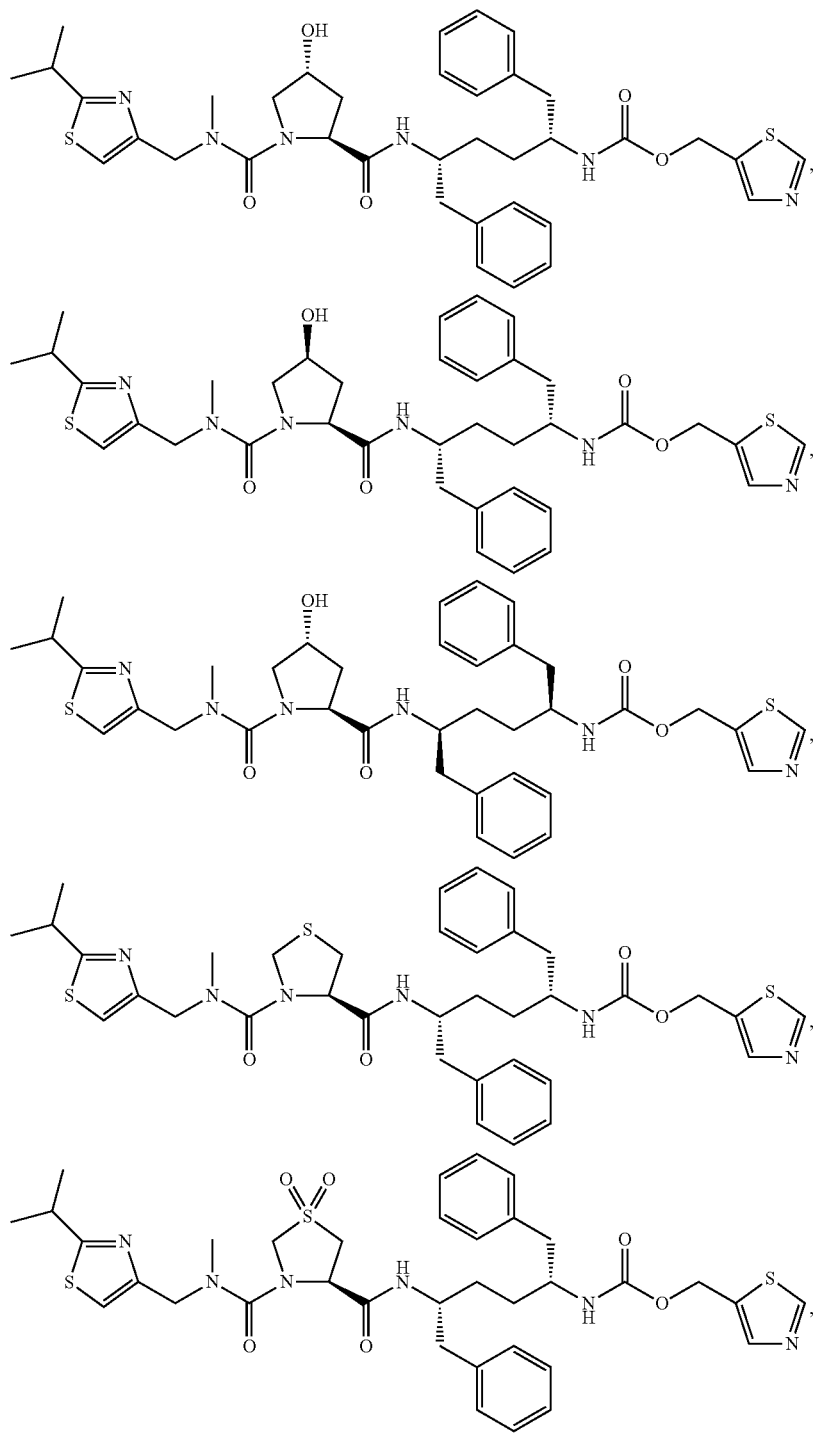

-continued
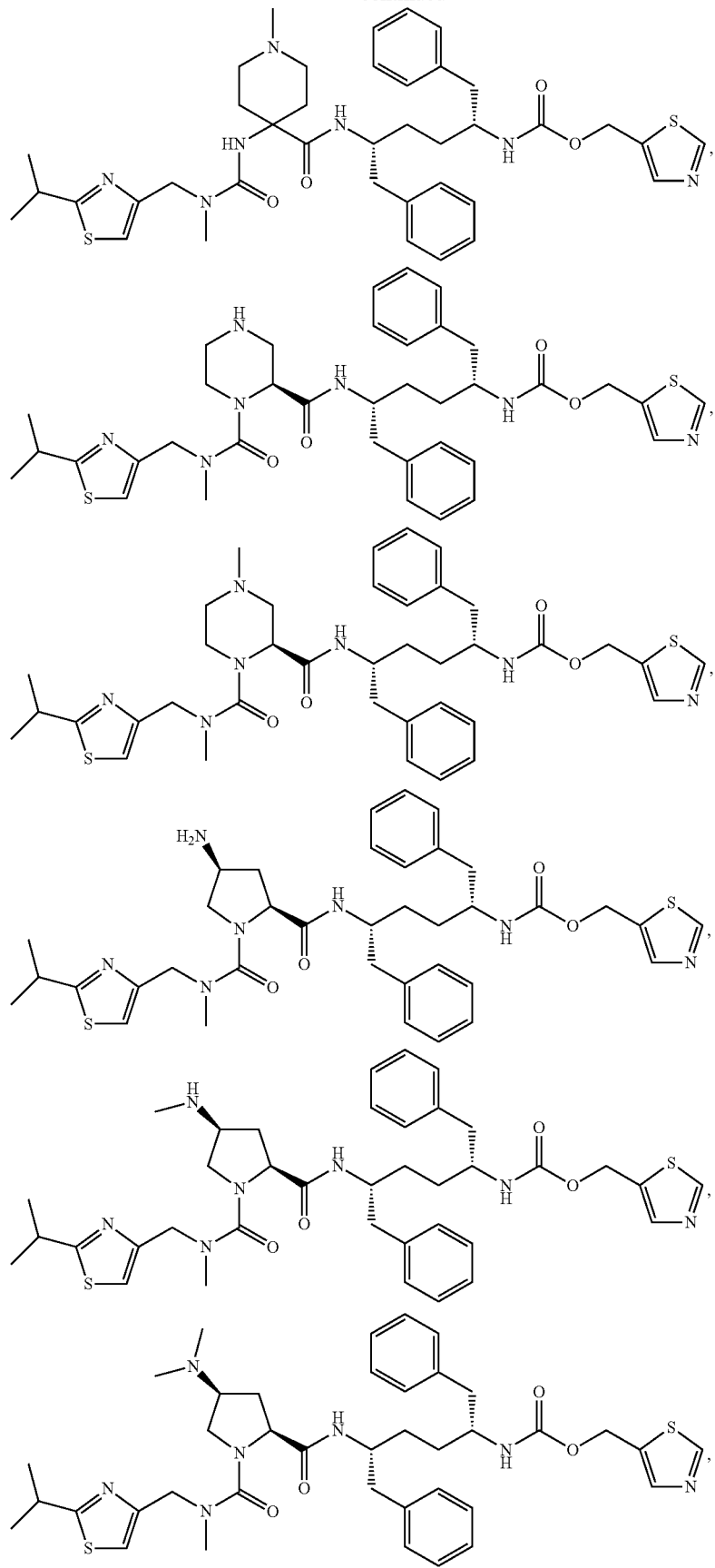

-continued
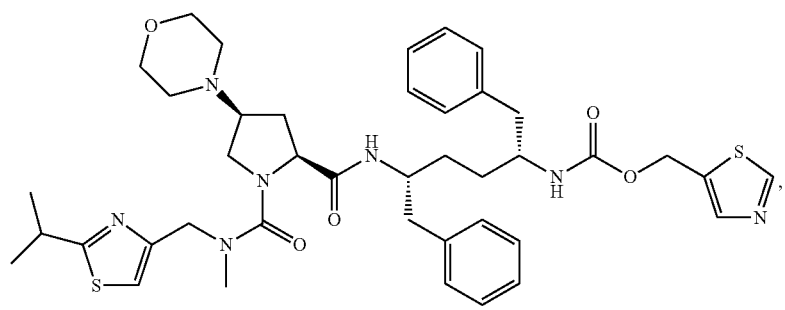
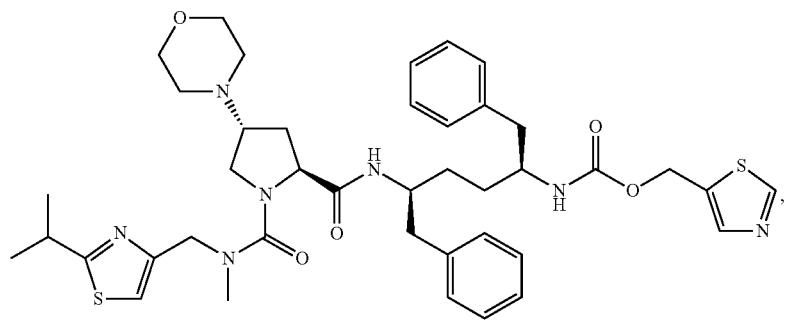
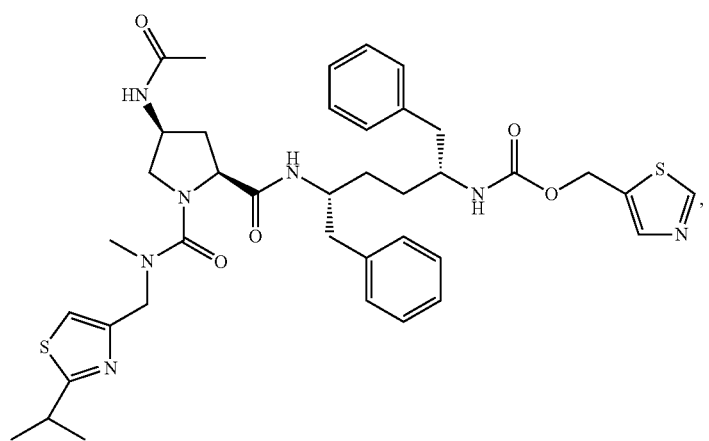
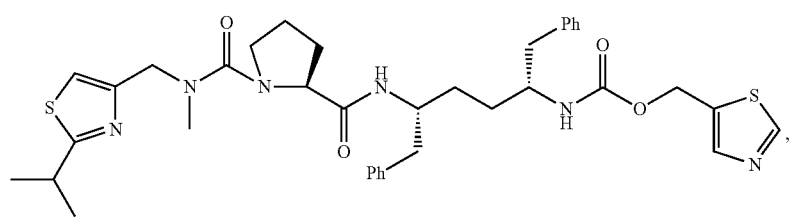
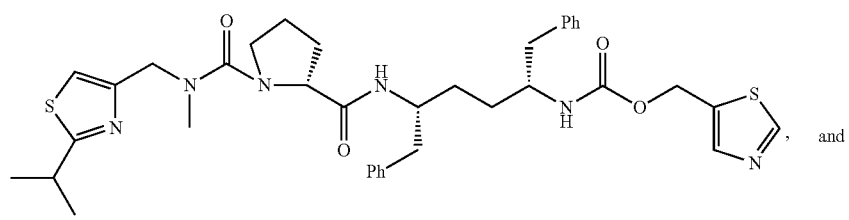

-continued

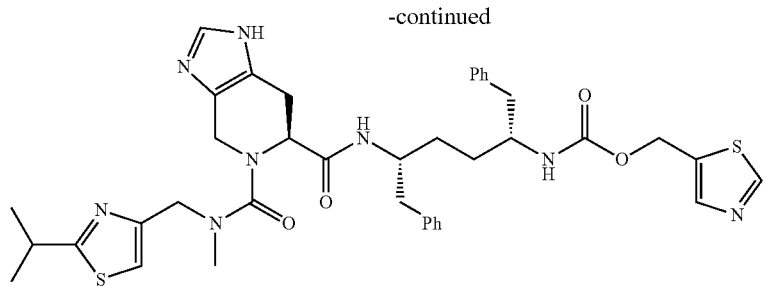

and salts thereof.

In one embodiment, the compound of formula I, has the structure of formula Ia:

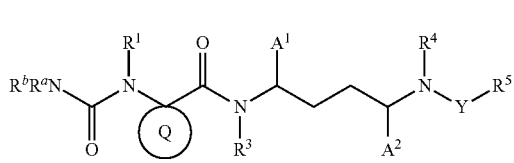

or a salt thereof, wherein $A^1$, $A^2$, $R^1$, $R^3$, $R^4$, $R^5$, $R^a$, $R^b$, Q and Y are as defined herein.

In one embodiment of the compounds of formula Ia, Q is a heterocyclyl or a carbocyclyl, wherein any heterocyclyl or carbocyclyl of Q is optionally substituted with one or more $Z^1$ groups.

In another embodiment of the compounds of formula Ia, Q is a heterocyclyl, wherein any heterocyclyl or of Q is optionally substituted with one or more $Z^1$ groups.

In another embodiment of the compounds of formula Ia, Q is a 6-membered heterocyclyl, wherein any 6-membered heterocyclyl or of Q is optionally substituted with one or more $Z^1$ groups.

In another embodiment of the compounds of formula Ia, Q is a piperidinyl, wherein the piperidinyl is optionally substituted with one or more $Z^1$ groups.

In another embodiment of the compounds of formula Ia, Q is 1-methylpiperidinyl.

In one embodiment of the compounds of formula Ia, $Z^1$ is OH, oxo, $(C_1\text{-}C_6)$alkyl, —$NR^dR^e$, —$NR^fC(O)R^g$ or heterocyclyl.

In one embodiment of the compounds of formula Ia, $R^d$ and $R^e$, are each independently H or $(C_1\text{-}C_6)$alkyl.

In another embodiment of the compounds of formula Ia, $R^d$ and $R^e$, are each independently H or —$CH_3$.

In another embodiment of the compounds of formula Ia, $R^d$ and $R^e$, are each H.

In another embodiment of the compounds of formula Ia, $R^d$ and $R^e$, are each —$CH_3$.

In another embodiment of the compounds of formula Ia, $Z^1$ is piperidine, morpholine, piperazine, N-methylpiperazine or pyrrolidine.

In another embodiment of the compounds of formula Ia, $Z^1$ is morpholine.

In one embodiment of the compounds of formula Ia, $R^f$ is H or $(C_1\text{-}C_6)$alkyl.

In another embodiment of the compounds of formula Ia, $R^f$ is H.

In one embodiment of the compounds of formula Ia, $R^g$ is $(C_1\text{-}C_6)$alkyl.

In another embodiment of the compounds of formula Ia, $R^g$ is —$CH_3$.

In another embodiment of the compounds of formula Ia, $Z^1$ is OH, —$CH_3$, —$NH_2$, —$N(CH_3)_2$, —$NHCH_3$, —$NHC(O)CH_3$ or morpholine.

In one embodiment of the compounds of formula Ia, $R^a$ is H or $(C_1\text{-}C_6)$alkyl.

In another embodiment of the compounds of formula Ia, $R^a$ is $(C_1\text{-}C_6)$alkyl.

In another embodiment of the compounds of formula Ia, $R^a$ is —$CH_3$.

In one embodiment of the compounds of formula Ia, $R^b$ is heteroaryl-$CH_2$—, wherein heteroaryl-$CH_2$— is optionally substituted with one or more $Z^5$ groups.

In another embodiment of the compounds of formula Ia, $R^b$ is a thiazol-4-ylmethyl, wherein the thiazol-4-ylmethyl is optionally substituted with one or more $Z^5$ groups.

In another embodiment of the compounds of formula Ia, $R^b$ is a thiazolylmethyl substituted with $(C_1\text{-}C_6)$alkyl.

In another embodiment of the compounds of formula Ia, $R^b$ is 2-isopropylthiazol-4-ylmethyl.

In one embodiment of the compounds of formula Ia, Y is —$C(O)NR^c$—.

In one embodiment of the compounds of formula Ia, $R^c$ is H.

In another embodiment of the compounds of formula Ia, $R^c$ is methyl.

In one embodiment of the compounds of formula Ia, Y is —$C(O)O$—.

In one embodiment of the compounds of formula Ia, $R^3$ is H.

In another embodiment of the compounds of formula Ia, $R^3$ is $(C_1\text{-}C_6)$alkyl.

In another embodiment of the compounds of formula Ia, $R^3$ is methyl.

In one embodiment of the compounds of formula Ia, $R^4$ is H.

In another embodiment of the compounds of formula Ia, $R^4$ is $(C_1\text{-}C_6)$alkyl.

In another embodiment of the compounds of formula Ia, $R^4$ is methyl.

In one embodiment of the compounds of formula Ia, $R^5$ is heteroaryl$(C_1\text{-}C_6)$alkyl, wherein any heteroaryl$(C_1\text{-}C_6)$alkyl of $R^5$ is optionally substituted with one or more $Z^4$ groups.

In another embodiment of the compounds of formula Ia, $R^5$ is heteroaryl-$CH_2$—, wherein any heteroaryl-$CH_2$— of $R^5$ is optionally substituted with one or more $Z^4$ groups.

In another embodiment of the compounds of formula Ia, $R^5$ is heteroaryl$(C_1\text{-}C_6)$alkyl.

In another embodiment of the compounds of formula Ia, $R^5$ is heteroaryl-$CH_2$—.

In another embodiment of the compounds of formula Ia, $R^5$ is thiazolomethyl.

In another embodiment of the compounds of formula Ia, $R^5$ is thiazol-5-ylmethyl.

In one embodiment of the compounds of formula Ia, $A^1$ is aryl($C_1$-$C_6$)alkyl, wherein any aryl($C_1$-$C_6$)alkyl of $A^1$ is optionally substituted with one or more $Z^3$ groups.

In another embodiment of the compounds of formula Ia, $A^1$ is phenyl($C_1$-$C_6$)alkyl, wherein any phenyl($C_1$-$C_6$)alkyl of $A^1$ is optionally substituted with one or more $Z^3$ groups.

In another embodiment of the compounds of formula Ia, $A^1$ is phenyl$CH_2$—, wherein any phenyl$CH_2$— of $A^1$ is optionally substituted with one or more $Z^3$ groups.

In another embodiment of the compounds of formula Ia, $A^1$ is phenyl$CH_2$—.

In one embodiment of the compounds of formula Ia, $A^2$ is aryl($C_1$-$C_6$)alkyl, wherein any aryl($C_1$-$C_6$)alkyl of $A^2$ is optionally substituted with one or more $Z^3$ groups.

In another embodiment of the compounds of formula Ia, $A^2$ is phenyl($C_1$-$C_6$)alkyl, wherein any phenyl($C_1$-$C_6$)alkyl of $A^2$ is optionally substituted with one or more $Z^3$ groups.

In another embodiment of the compounds of formula Ia, $A^2$ is phenyl$CH_2$—, wherein any phenyl$CH_2$— of $A^2$ is optionally substituted with one or more $Z^3$ groups.

In another embodiment of the compounds of formula Ia, $A^2$ is phenyl$CH_2$—.

In one embodiment, the compound of formula I, has the structure of formula Ib:

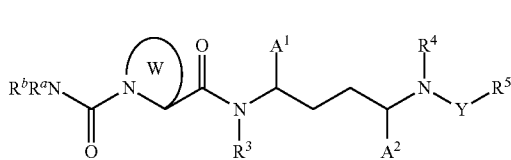

Ib or a salt thereof, wherein $A^1$, $A^2$, $R^3$, $R^4$, $R^5$, $R^a$, $R^b$, W and Y are as defined herein.

In one embodiment of the compounds of formula Ib, W is a heterocyclyl, wherein any heterocyclyl of W is optionally substituted with one or more $Z^1$ groups.

In another embodiment of the compounds of formula Ib, W is a 5 or 6-membered heterocyclyl, wherein any 5 or 6-membered heterocyclyl of W is optionally substituted with one or more $Z^1$ groups.

In another embodiment of the compounds of formula Ib, W is a 9 or 10-membered bicyclic heterocyclyl, wherein any 9 or 10-membered bicyclic heterocyclyl of W is optionally substituted with one or more $Z^1$ groups.

In another embodiment of the compounds of formula Ib, W is piperazinyl, pyrrolidinyl, thiazolidinyl, S,S-dioxo-thiazolidinyl or 4,5,6,7-tetrahydro-3H-imidazo[4,5-c]pyridinyl, each optionally substituted with one or more $Z^1$ groups.

In another embodiment of the compounds of formula Ib, W is piperazinyl, 1-methylpiperazinyl, hydroxypyrrolidinyl, N—N-dimethylaminopyrrolidinyl, N-methylaminopyrrolidinyl, aminopyrrolidinyl, morpholinopyrrolidinyl, acetylaminopyrrolidinyl, pyrrolidinyl, thiazolidinyl, S,S-dioxothiazolidinyl or 4,5,6,7-tetrahydro-3H-imidazo[4,5-c]pyridinyl.

In one embodiment of the compounds of formula Ib, $Z^1$ is OH, oxo, ($C_1$-$C_6$)alkyl, —$NR^dR^e$ or —$NR^fC(O)R^g$.

In one embodiment of the compounds of formula Ib, $R^d$ and $R^e$, are each independently H or ($C_1$-$C_6$)alkyl.

In another embodiment of the compounds of formula Ib, $R^d$ and $R^e$, are each independently H or —$CH_3$.

In another embodiment of the compounds of formula Ib, $R^d$ and $R^e$, are each H.

In another embodiment of the compounds of formula Ib, $R^d$ and $R^e$, are each —$CH_3$.

In another embodiment of the compounds of formula Ib, $Z^1$ is piperidine, morpholine, piperazine, N-methylpiperazine or pyrrolidine.

In another embodiment of the compounds of formula Ib, $Z^1$ is morpholine.

In one embodiment of the compounds of formula Ib, $R^f$ is H or ($C_1$-$C_6$)alkyl.

In another embodiment of the compounds of formula Ib, W is H.

In one embodiment of the compounds of formula Ib, $R^g$ is ($C_1$-$C_6$)alkyl.

In another embodiment of the compounds of formula Ib, $R^g$ is —$CH_3$.

In another embodiment of the compounds of formula Ib, $Z^1$ is OH, —$CH_3$, —$NH_2$, —$N(CH_3)_2$, —$NHCH_3$, —$NHC(O)CH_3$ or morpholine.

In one embodiment of the compounds of formula Ib, $R^a$ is H or ($C_1$-$C_6$)alkyl.

In another embodiment of the compounds of formula Ib, $R^a$ is ($C_1$-$C_6$)alkyl.

In another embodiment of the compounds of formula Ib, $R^a$ is —$CH_3$.

In one embodiment of the compounds of formula Ib, $R^b$ is heteroaryl-$CH_2$—, wherein any heteroaryl-$CH_2$— of $R^b$ is optionally substituted with one or more $Z^5$ groups.

In another embodiment of the compounds of formula Ib, $R^b$ is a thiazol-4-ylmethyl, wherein the thiazol-4-ylmethyl is optionally substituted with one or more $Z^5$ groups.

In another embodiment of the compounds of formula Ib, $R^b$ is thiazolylmethyl substituted with ($C_1$-$C_6$)alkyl.

In another embodiment of the compounds of formula Ib, $R^b$ is 2-isopropylthiazol-4-ylmethyl.

In one embodiment of the compounds of formula Ib, Y is —C(O)$NR^c$—.

In one embodiment of the compounds of formula Ib, $R^c$ is H.

In another embodiment of the compounds of formula Ib, $R^c$ is methyl.

In one embodiment of the compounds of formula Ib, Y is —C(O)O—.

In one embodiment of the compounds of formula Ib, $R^3$ is H.

In another embodiment of the compounds of formula Ib, $R^3$ is ($C_1$-$C_6$)alkyl.

In another embodiment of the compounds of formula Ib, $R^3$ is methyl.

In one embodiment of the compounds of formula Ib, $R^4$ is H.

In another embodiment of the compounds of formula Ib, $R^4$ is ($C_1$-$C_6$)alkyl.

In another embodiment of the compounds of formula Ib, $R^4$ is methyl.

In one embodiment of the compounds of formula Ib, $R^5$ is heteroaryl($C_1$-$C_6$)alkyl, wherein any heteroaryl($C_1$-$C_6$)alkyl of $R^5$ is optionally substituted with one or more $Z^4$ groups.

In another embodiment of the compounds of formula Ib, $R^5$ is heteroaryl-$CH_2$—, wherein any heteroaryl-$CH_2$— of $R^5$ is optionally substituted with one or more $Z^4$ groups.

In another embodiment of the compounds of formula Ib, $R^5$ is heteroaryl($C_1$-$C_6$)alkyl.

In another embodiment of the compounds of formula Ib, $R^5$ is heteroaryl-$CH_2$—.

In another embodiment of the compounds of formula Ib, $R^5$ is thiazolomethyl.

In another embodiment of the compounds of formula Ib, $R^5$ is thiazol-5-ylmethyl.

In one embodiment of the compounds of formula Ib, $A^1$ is aryl($C_1$-$C_6$)alkyl, wherein any aryl($C_1$-$C_6$)alkyl of $A^1$ is optionally substituted with one or more $Z^3$ groups.

In another embodiment of the compounds of formula Ib, $A^1$ is phenyl($C_1$-$C_6$)alkyl, wherein any phenyl($C_1$-$C_6$)alkyl of $A^1$ is optionally substituted with one or more $Z^3$ groups.

In another embodiment of the compounds of formula Ib, $A^1$ is phenylCH$_2$—, wherein any phenylCH$_2$— of $A^1$ is optionally substituted with one or more $Z^3$ groups.

In another embodiment of the compounds of formula Ib, $A^1$ is phenylCH$_2$—.

In one embodiment of the compounds of formula Ib, $A^2$ is aryl($C_1$-$C_6$)alkyl, wherein any aryl($C_1$-$C_6$)alkyl of $A^2$ is optionally substituted with one or more $Z^3$ groups.

In another embodiment of the compounds of formula Ib, $A^2$ is phenyl($C_1$-$C_6$)alkyl, wherein any phenyl($C_1$-$C_6$)alkyl of $A^2$ is optionally substituted with one or more $Z^3$ groups.

In another embodiment of the compounds of formula Ib, $A^2$ is phenylCH$_2$—, wherein any phenylCH$_2$— of $A^2$ is optionally substituted with one or more $Z^3$ groups.

In another embodiment of the compounds of formula Ib, $A^2$ is phenylCH$_2$—.

In one embodiment, the compounds of formula I, have the structure of formula Ic:

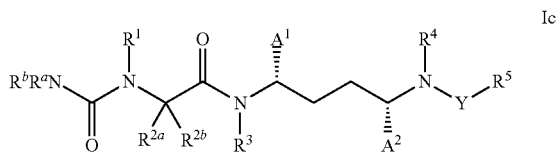

wherein $A^1$, $A^2$, $R^3$, $R^4$, $R^5$, $R^a$, $R^b$, $R2^a$, $R2^b$ and Y are as defined herein.

In one embodiment, the compounds of formula Ic are at least 60% a single stereoisomer at both the carbon attached to the $A^1$ substituent and the carbon attached to the $A^2$ substituent. In another embodiment, the compounds of formula Ic are at least 70% a single stereoisomer at both the carbon attached to the $A^1$ substituent and the carbon attached to the $A^2$ substituent. In another embodiment, the compounds of formula Ic are at least 80% a single stereoisomer at both the carbon attached to the $A^1$ substituent and the carbon attached to the $A^2$ substituent. In another embodiment, the compounds of formula Ic are at least 90% a single stereoisomer at both the carbon attached to the $A^1$ substituent and the carbon attached to the $A^2$ substituent. In another embodiment, the compounds of formula Ic are at least 95% a single stereoisomer at both the carbon attached to the $A^1$ substituent and the carbon attached to the $A^2$ substituent.

In one embodiment of the compounds of formula Ic, $R^1$ is H or ($C_1$-$C_6$)alkyl, and $R^{2a}$ and $R^{2b}$ taken together with the carbon to which they are attached form a heterocyclyl or a carbocyclyl, wherein any heterocyclyl or carbocyclyl of $R^{2a}$ and $R^{2b}$ is optionally substituted with one or more $Z^1$ groups.

In another embodiment of the compounds of formula Ic, $R^1$ is H and $R^{2a}$ and $R^{2b}$ taken together with the carbon to which they are attached form a heterocyclyl or a carbocyclyl, wherein any heterocyclyl or carbocyclyl of $R^{2a}$ and $R^{2b}$ is optionally substituted with one or more $Z^1$ groups.

In another embodiment of the compounds of formula Ic, $R^1$ is $CH_3$, and $R^{2a}$ and $R^{2b}$ taken together with the carbon to which they are attached form a heterocyclyl or a carbocyclyl, wherein any heterocyclyl or carbocyclyl of $R^{2a}$ and $R^{2b}$ is optionally substituted with one or more $Z^1$ groups.

In another embodiment of the compounds of formula Ic, $R^1$ is H or ($C_1$-$C_6$)alkyl, and $R^{2a}$ and $R^{2b}$ taken together with the carbon to which they are attached form a heterocyclyl, wherein any heterocyclyl of $R^{2a}$ and $R^{2b}$ is optionally substituted with one or more $Z^1$ groups.

In another embodiment of the compounds of formula Ic, $R^1$ is H, and $R^{2a}$ and $R^{2b}$ taken together with the carbon to which they are attached form a heterocyclyl, wherein any heterocyclyl of $R^{2a}$ and $R^{2b}$ is optionally substituted with one or more $Z^1$ groups.

In another embodiment of the compounds of formula Ic, $R^1$ is $CH_3$, and $R^{2a}$ and $R^{2b}$ together with the carbon to which they are attached form a heterocyclyl, wherein any heterocyclyl of $R^{2a}$ and $R^{2b}$ is optionally substituted with one or more $Z^1$ groups.

In another embodiment of the compounds of formula Ic, $R^1$ is H or ($C_1$-$C_6$)alkyl, and $R^{2a}$ and $R^{2b}$ taken together with the carbon to which they are attached form a piperidinyl, wherein the piperidinyl is optionally substituted with one or more $Z^1$ groups.

In another embodiment of the compounds of formula Ic, $R^1$ is H, and $R^{2a}$ and $R^{2b}$ taken together with the carbon to which they are attached form a piperidinyl, wherein the piperidinyl is optionally substituted with one or more $Z^1$ groups.

In another embodiment of the compounds of formula Ic, $R^1$ is $CH_3$, and $R^{2a}$ and $R^{2b}$ taken together with the carbon to which they are attached form a piperidinyl, wherein the piperidinyl is optionally substituted with one or more $Z^1$ groups.

In another embodiment of the compounds of formula Ic, $R^1$ is H or ($C_1$-$C_6$)alkyl, and $R^{2a}$ and $R^{2b}$ together with the carbon to which they are attached form a 1-methylpiperidinyl.

In another embodiment of the compounds of formula Ic, $R^1$ is H, and $R^{2a}$ and $R^{2b}$ together with the carbon to which they are attached form a 1-methylpiperidinyl.

In another embodiment of the compounds of formula Ic, $R^1$ is $CH_3$, and $R^{2a}$ and $R^{2b}$ together with the carbon to which they are attached form a 1-methylpiperidinyl.

In one embodiment of the compounds of formula Ic, $R^{2b}$ is H, and $R^{2a}$ and $R^1$ together with the atoms to which they are attached form a heterocyclyl, wherein any heterocyclyl of $R^{2a}$ and $R^1$ is optionally substituted with one or more $Z^1$ groups.

In another embodiment of the compounds of formula Ic, $R^{2b}$ is H, and $R^{2a}$ and $R^1$ taken together with the atoms to which they are attached form a piperazinyl, pyrrolidinyl, thiazolidinyl, S,S-dioxo-thiazolidinyl or 4,5,6,7-tetrahydro-3H-imidazo[4,5-c]pyridinyl, each of which is optionally substituted with one or more $Z^1$ groups.

In another embodiment of the compounds of formula Ic, $R^{2b}$ is H, and $R^{2a}$ and $R^1$ taken together with the atoms to which they are attached form a piperazinyl, 1-methylpiperazinyl, hydroxypyrrolidinyl, N—N-dimethylaminopyrrolidinyl, N-methylaminopyrrolidinyl, aminopyrrolidinyl, morpholinopyrrolidinyl, acetylaminopyrrolidinyl, pyrrolidinyl, thiazolidinyl, S,S-dioxo-thiazolidinyl or 4,5,6,7-tetrahydro-3H-imidazo[4,5-c]pyridinyl.

In one embodiment of the compounds of formula Ic, $Z^1$ is OH, oxo, ($C_1$-$C_6$)alkyl, —$NR^dR^e$, $NR^fC(O)R^g$ or heterocyclyl.

In one embodiment of the compounds of formula Ic, $R^d$ and $R^e$ are each independently H or ($C_1$-$C_6$)alkyl.

In another embodiment of the compounds of formula Ic, $R^d$ and $R^e$ are each independently H or —$CH_3$.

In another embodiment of the compounds of formula Ic, $R^d$ and $R^e$ are each H.

In another embodiment of the compounds of formula Ic, $R^d$ and $R^e$ are each —$CH_3$.

In another embodiment of the compounds of formula Ic, $Z^1$ is piperidine, morpholine, piperazine, N-methylpiperazine or pyrrolidine.

In another embodiment of the compounds of formula Ic, $Z^1$ is morpholine.

In one embodiment of the compounds of formula Ic, $R^f$ is H or $(C_1-C_6)$alkyl.

In another embodiment of the compounds of formula Ic, $R^f$ is H.

In one embodiment of the compounds of formula Ic, $R^g$ is $(C_1-C_6)$alkyl.

In another embodiment of the compounds of formula Ic, $R^g$ is —$CH_3$.

In another embodiment of the compounds of formula Ic, $Z^1$ is OH, —$CH_3$, —$NH_2$, —$N(CH_3)_2$, —$NHCH_3$, —NHC(O)$CH_3$ or morpholine.

In one embodiment of the compounds of formula Ic, $R^a$ is H or $(C_1-C_6)$alkyl.

In another embodiment of the compounds of formula Ic, $R^a$ is $(C_1-C_6)$alkyl.

In another embodiment of the compounds of formula Ic, $R^a$ is —$CH_3$.

In one embodiment of the compounds of formula Ic, $R^b$ is heteroaryl-$CH_2$—, wherein heteroaryl-$CH_2$— is optionally substituted with one or more $Z^5$ groups.

In another embodiment of the compounds of formula Ic, $R^b$ is a thiazol-4-ylmethyl, wherein the thiazol-4-ylmethyl is optionally substituted with one or more $Z^5$ groups.

In another embodiment of the compounds of formula Ic, $R^b$ is thiazolylmethyl substituted with $(C_1-C_6)$alkyl.

In another embodiment of the compounds of formula Ic, $R^b$ is 2-isopropylthiazol-4-ylmethyl.

In one embodiment of the compounds of formula Ic, Y is —C(O)$NR^c$—.

In one embodiment of the compounds of formula Ic, $R^c$ is H.

In another embodiment of the compounds of formula Ic, $R^c$ is methyl.

In one embodiment of the compounds of formula Ic, Y is —C(O)O—.

In one embodiment of the compounds of formula Ic, $R^3$ is H.

In another embodiment of the compounds of formula Ic, $R^3$ is $(C_1-C_6)$alkyl.

In another embodiment of the compounds of formula Ic, $R^3$ is methyl.

In one embodiment of the compounds of formula Ic, $R^4$ is H.

In another embodiment of the compounds of formula Ic, $R^4$ is $(C_1-C_6)$alkyl.

In another embodiment of the compounds of formula Ic, $R^4$ is methyl.

In one embodiment of the compounds of formula Ic, $R^5$ is heteroaryl$(C_1-C_6)$alkyl, wherein any heteroaryl$(C_1-C_6)$alkyl of $R^5$ is optionally substituted with one or more $Z^6$ groups.

In another embodiment of the compounds of formula Ic, $R^5$ is heteroaryl-$CH_2$—, wherein any heteroaryl-$CH_2$— of $R^5$ is optionally substituted with one or more $Z^6$ groups.

In another embodiment of the compounds of formula Ic, $R^5$ is heteroaryl$(C_1-C_6)$alkyl.

In another embodiment of the compounds of formula Ic, $R^5$ is heteroaryl-$CH_2$—.

In another embodiment of the compounds of formula Ic, $R^5$ is thiazolomethyl.

In another embodiment of the compounds of formula Ic, $R^5$ is thiazol-5-ylmethyl.

In one embodiment of the compounds of formula Ic, $A^1$ is aryl$(C_1-C_6)$alkyl, wherein any aryl$(C_1-C_6)$alkyl of $A^1$ is optionally substituted with one or more $Z^3$ groups.

In another embodiment of the compounds of formula Ic, $A^1$ is phenyl$(C_1-C_6)$alkyl, wherein any phenyl$(C_1-C_6)$alkyl of $A^1$ is optionally substituted with one or more $Z^3$ groups.

In another embodiment of the compounds of formula Ic, $A^1$ is phenyl$CH_2$—, wherein any phenyl$CH_2$— of $A^1$ is optionally substituted with one or more $Z^3$ groups.

In another embodiment of the compounds of formula Ic, $A^1$ is phenyl$CH_2$—.

In one embodiment of the compounds of formula Ic, $A^2$ is aryl$(C_1-C_6)$alkyl, wherein any aryl$(C_1-C_6)$alkyl of $A^2$ is optionally substituted with one or more $Z^3$ groups.

In another embodiment of the compounds of formula Ic, $A^2$ is phenyl$(C_1-C_6)$alkyl, wherein any phenyl$(C_1-C_6)$alkyl of $A^2$ is optionally substituted with one or more $Z^3$ groups.

In another embodiment of the compounds of formula Ic, $A^2$ is phenyl$CH_2$—, wherein any phenyl$CH_2$— of $A^2$ is optionally substituted with one or more $Z^3$ groups.

In another embodiment of the compounds of formula Ic, $A^2$ is phenyl$CH_2$—.

In one embodiment, the compound of the invention has an inhibition activity against P450 at a level equal to or better than the inhibition activity of a compound as represented by an $IC_{50}$ of less than about 2000 nM, less than about 1500 nM, less than about 1000 nM, less than about 900 nM, less than about 800 nM, less than about 700 nM, less than about 650 nM, less than about 600 nM, less than about 550 nM, less than about 500 nM, less than about 400 nM, less than about 350 nM, less than about 300 nM, less than about 250 nM, less than about 200 nM, less than about 100 nM, or less than about 50 nM.

In another embodiment, the compound of the invention has an inhibition activity against an isozyme of P450, e.g., 3A in a range represented by $IC_{50}$ from about 2000 nM to about 100 nM, from about 1000 nM to about 100 nM, from about 900 nM to about 200 nM, from about 800 nM to about 300 nM, from about 700 nM to about 200 nM, from about 600 nM to about 200 nM, from about 500 nM to about 200 nM, from about 700 nM to about 300 nM, from about 600 nM to about 300 nM, from about 700 nM to about 400 nM, from about 600 nM to about 400 nM, from about 400 nM to about 100 nM, from about 300 nM to about 100 nM, or from about 600 nM to about 150 nM.

In another embodiment, the compound of the invention has an inhibition activity against P450 at a level equal to or better than the inhibition activity of a compound as represented by an $IC_{50}$ of less than about 2000 nM, less than about 1500 nM, less than about 1000 nM, less than about 900 nM, less than about 800 nM, less than about 700 nM, less than about 650 nM, less than about 600 nM, less than about 550 nM, less than about 500 nM, less than about 400 nM, less than about 350 nM, less than about 300 nM, less than about 250 nM, less than about 200 nM, less than about 100 nM, or less than about 50 nM, provided that such compound also does not substantially exhibit biological activities other than its inhibition activity against P450. For example, the compound of the invention can have a reduced or not significant activity of protease inhibition, including without any limitation a level of protease inhibition as represented by HIV $EC_{50}$ of greater than about 1000 nM, greater than about 900 nM, greater than about 800 nM, greater than about 700 nM, greater than about 600 nM, greater than about 500 nM, greater than about 400 nM, greater than about 300 nM, greater than about 200 nM, greater than about 100 nM, greater than about 50 nM, greater than about 40 nM, greater than about 30 nM, greater than about 20 nM, greater than about 10 nM, greater than about 5 nM, or greater than about 1 nM.

In another embodiment, the compound of the invention has an inhibition activity specifically against one or more isozymes of P450 including without limitation 1A2, 2B6, 2C8, 2C19, 2C9, 2D6, 2E1, and 3A4, 5, 7, etc.

In another embodiment, the compound of the invention has an inhibition activity specifically against an isozyme of P450 that is involved in metabolizing anti-viral drugs, e.g., indinavir, nelfinavir, ritonavir, saquinavir etc.

In another embodiment, the compound of the invention has an inhibition activity specifically against one or more isozymes of P450, but not the other(s). For example, the compound of the present invention can have an inhibition activity specifically against P450 3A, but a reduced, insubstantial, or minimum inhibition activity against another isozyme of P450, e.g., P450 2C9.

Pharmaceutical Formulations

The compounds of this invention can be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, e.g. a compound of the present invention, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents.

Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty add and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty adds and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 1 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients provided by the present invention the formulations of this invention may include other agents conventional in the art having regard to the type of formulation in question, for example those suitable for oral administration may include flavoring agents.

The invention further provides veterinary compositions comprising at least one active ingredient, e.g., a compound of the present invention together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

In one embodiment, the invention provides pharmaceutical compositions comprising a compound of the invention, or a pharmaceutically acceptable salt thereof, and a pharmaceutically acceptable carrier or excipient.

In another embodiment, the invention provides pharmaceutical compositions comprising a compound of the invention, or a pharmaceutically acceptable salt thereof, in combination with at least one additional therapeutic agent, and a pharmaceutically acceptable carrier or excipient.

Combination Pharmaceutical Agent

Compounds of the invention can be combined with one or more additional therapeutic agents in a single composition to form a combination pharmaceutical agent.

According to the invention, the therapeutic agent used in combination with the compound of the invention can be any therapeutic agent having a therapeutic effect when used in combination with the compound of the invention. For example, the therapeutic agent used in combination with the compound of the invention can be any therapeutic agent that is accessible to oxidative metabolism by cytochrome P450 enzymes, especially cytochrome P450 monooxygenase, e.g., 1A2, 2B6, 2C8, 2C19, 2C9, 2D6, 2E1, 3A4,5,7, etc.

In one embodiment of the invention, the therapeutic agent used in combination with the compound of the invention can be any anti-viral agent, e.g., anti-HIV, anti-HCV, etc., anti-bacterial agent, anti-fungal agent, immuno-modulator, e.g., immunosuppressant, anti-neoplastic agent, chemotherapeutic agent, agents useful for treating cardiovascular conditions, neurological conditions, etc.

In another embodiment of the invention, the therapeutic agent used in combination with the compound of the invention can be any proton pump inhibitor, anti-epileptics, NSAID, oral hypoglycemic agent, angiotensin II, sulfonylureas, beta blocker, antidepressant, antipsychotics, or anesthetics, or a combination thereof.

In another embodiment, the invention provides a combination pharmaceutical agent comprising:

a) a first pharmaceutical composition comprising a compound of the invention, or a pharmaceutically acceptable salt thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Routes of Administration

One or more compounds of the invention are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the certain compounds of this invention is that they are orally bioavailable and can be dosed orally.

Doses

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

Co-Administration

Co-administration includes administration of any compound of the invention with one or more other active therapeutic agents in a single unitary dosage form (i.e. administration of a combination pharmaceutical agent).

Co-administration also includes administration of any compound of the invention as a unitary dosage form along with one or more other active therapeutic agents each in a unitary dosage form for simultaneous or sequential administration to a patient (i.e. combination therapy). Co-administration also includes administration of any compound of the invention with one or more active therapeutic agents as a unitary dosage form along with one or more active therapeutic agents each in a unitary dosage or optionally combined together to form a unitary dosage (or a combination thereof) for simultaneous or sequential administration to a patient (i.e. combination therapy). The unitary dosage forms (i.e. combination therapy) may be administered as a simultaneous or sequential regimen. When administered sequentially, the combination may be administered in two or more administrations.

Co-administration includes administration of unit dosages (as described above) of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

Co-administration of a compound of the invention with one or more other active therapeutic agents also refers to simultaneous or sequential administration of a compound of the invention and one or more other active therapeutic agents, such that therapeutically effective amounts of the compound of the invention and one or more other active therapeutic agents are both present in the body of the patient.

In one embodiment, the compounds of the invention can be used alone, e.g., for inhibiting cytochrome P450 monooxygenase. In another embodiment, the compounds of the present invention are used in combination with other active therapeutic ingredients or agents. Preferably, the other active therapeutic ingredients or agents are metabolized or accessible to the oxidative metabolism by cytochrome P450 enzymes, e.g., monooxygenase enzymes such as 1A2, 2B6, 2C8, 2C19, 2C9, 2D6, 2E1, 3A4,5,7, etc.

Combinations

Combinations (for use in combination therapy) of the compounds of the present invention are typically selected based on the condition to be treated, cross-reactivities of ingredients and pharmaco-properties of the combination. For example, when treating an infection (e.g., HIV or HCV), the compositions of the invention are combined with anti-infective agents (such as those agents selected form the classes of compounds described herein).

In one embodiment, non-limiting examples of suitable combinations include combinations of one or more compounds of the present invention with one or more anti-viral agents, e.g., anti-HIV, anti-HCV, etc., anti-bacterial agents, anti-fungal agents, immuno-modulators, e.g., immunosuppressant, anti-neoplastic agents, chemotherapeutic agents, agents useful for treating cardiovascular conditions, neurological conditions, etc.

In another embodiment, non-limiting examples of suitable combinations include combinations of one or more compounds of the present invention with one or more proton pump inhibitors, anti-epileptics, NSAIDs, oral hypoglycemic agents, angiotensin II, sulfonylureas, beta blockers, antidepressants, antipsychotics, or anesthetics, or a combination thereof.

In another embodiment, non-limiting examples of suitable combinations include combinations of one or more compounds of the present invention with one or more HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, and other drugs for treating HIV, interferons, ribavirin analogs, HCV NS3 protease inhibitors, alpha-glucosidase 1 inhibitors, hepatoprotectants, nucleoside or nucleotide inhibitors of HCV, non-nucleoside inhibitors of HCV, and other drugs for treating HCV.

In another embodiment, the invention provides pharmaceutical compositions comprising a compound of the invention, or a pharmaceutically acceptable salt, thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, CCR5 inhibitors, and combinations thereof, and a pharmaceutically acceptable carrier or excipient.

In another embodiment, the invention provides pharmaceutical compositions comprising a compound of the invention, or a pharmaceutically acceptable salt, thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

It is also contemplated that the compounds of invention can be used with any other active therapeutic agent or ingredient which is appreciably metabolized by cytochrome P450 monooxygenase enzymes, e.g. cytochrome P450 monooxygenase 3A, thereby reducing the amount or rate at which the other active therapeutic agent or ingredient is metabolized, whereby the pharmacokinetics of the other active therapeutic agent or ingredient is improved. The pharmacokinetics of a drug will determine the concentration of the drug at its intended site of therapeutic activity in an organism. Typical, but non-limiting, pharmacokinetic parameters measured are the half-life ($t_{1/2}$), maximum concentration ($C_{max}$), mean residence time (MRT), rate of clearance (CL) and volume of distribution ($V_D$). Non-limiting examples of improved pharmacokinetic parameters would be increased $t_{1/2}$, increased MRT, increased $C_{max}$ and decreased CL. In mammals, these parameters are usually determined by measuring the concentration of the drug in the blood over a period of time using conventional analytical techniques. Pharmacokinetic improvements usually include elevating the blood plasma levels of the other therapeutic agent or ingredient at a given time point or maintaining a therapeutically effective blood plasma level of the other therapeutic active agent or ingredient for a longer time period—compared to blood plasma levels of the other therapeutic agent or ingredient administered without the compound of the present invention. Although the blood may not be the optimal site of therapeutic activity for the drug, the concentration at the site of therapeutic activity is usually proportional to the concentration in the blood at a particular time point for a given dose of drug.

In another embodiment, the invention provides a method for improving the pharmacokinetics of a drug which is metabolized by cytochrome P450 monooxygenase, comprising administering to a patient treated with said drug, a therapeutically effective amount of a compound of the present invention, or a pharmaceutically acceptable salt thereof. In another aspect of this embodiment, the $t_{1/2}$ is increased. In another aspect of this embodiment, the $C_{max}$ is increased. In another aspect of this embodiment, the MRT is increased. In another aspect of this embodiment, the CL is decreased. In another aspect of this embodiment, co-administration of a therapeutically effective amount of a compound of formula I improves at least one of the pharmacokinetic parameters of the drug by at least about 10% to about 500%. In another aspect of this embodiment, co-administration of a therapeutically effective amount of a compound of formula I improves at least one of the pharmacokinetic parameters of the drug by at least about 10%. In another aspect of this embodiment, co-administration of a therapeutically effective amount of a compound of formula I improves at least one of the pharmacokinetic parameters of the drug by at least about 25%. In another aspect of this embodiment, co-administration of a therapeutically effective amount of a compound of formula I improves at least one of the pharmacokinetic parameters of the drug by at least about 50%. In another aspect of this embodiment, co-administration of a therapeutically effective amount of a compound of formula I improves at least one of the pharmacokinetic parameters of the drug by at least about 100%. In another aspect of this embodiment, co-administration of a therapeutically effective amount of a compound of formula I improves at least one of the pharmacokinetic parameters of the drug by at least about 200%. In another aspect of this embodiment, co-administration of a therapeutically effective amount of a compound of formula I improves at least one of the pharmacokinetic parameters of the drug by at least about 500%.

In another embodiment, the invention provides a method for improving the pharmacokinetics of a drug which is metabolized by cytochrome P450 monooxygenase, comprising administering to a patient treated with said drug, a therapeutically effective amount of a combination comprising said drug and a compound of the present invention, or a pharmaceutically acceptable salt thereof. In another aspect of this embodiment, the $t_{1/2}$ is increased. In another aspect of this embodiment, the $C_{max}$ is increased. In another aspect of this embodiment, the MRT is increased. In another aspect of this embodiment, the CL is decreased. In another aspect of this embodiment, the therapeutically effective amount of the combination improves at least one of the pharmacokinetic parameters of the drug by at least about 10% to about 500%. In another aspect of this embodiment, the therapeutically effective amount of the combination improves at least one of the pharmacokinetic parameters of the drug by at least about 10%. In another aspect of this embodiment, the therapeutically effective amount of the combination improves at least one of the pharmacokinetic parameters of the drug by at least about 25%. In another aspect of this embodiment, the therapeutically effective amount of the combination improves at least one of the pharmacokinetic parameters of the drug by at least about 50%. In another aspect of this embodiment, the therapeutically effective amount of the combination improves at least one of the pharmacokinetic parameters of the drug by at least about 100%. In another aspect of this embodiment, the therapeutically effective amount of the combination improves at least one of the pharmacokinetic parameters of the drug by at least about 200%. In another aspect of this embodiment, the therapeutically effective amount of the combination improves at least one of the pharmacokinetic parameters of the drug by at least about 500%.

In another embodiment, the invention provides a method for improving the pharmacokinetics of a drug which is metabolized by cytochrome P450 monooxygenase 3A, comprising administering to a patient treated with said drug, a therapeutically effective amount of a compound of the present invention, or a pharmaceutically acceptable salt thereof. In another aspect of this embodiment, the $t_{1/2}$ is increased. In another aspect of this embodiment, the $C_{max}$ is increased. In another aspect of this embodiment, the MRT is increased. In another aspect of this embodiment, the CL is decreased. In another aspect of this embodiment, co-administration of a therapeutically effective amount of a compound of formula I improves at least one of the pharmacokinetic parameters of the drug by at least about 10% to about 500%. In another aspect of this embodiment, co-administration of a therapeutically effective amount of a compound of formula I improves at least one of the pharmacokinetic parameters of the drug by at least about 10%. In another aspect of this embodiment, co-administration of a therapeutically effective amount of a compound of formula I improves at least one of the pharmacokinetic parameters of the drug by at least about 25%. In another aspect of this embodiment, co-administration of a therapeutically effective amount of a compound of formula I improves at least one of the pharmacokinetic parameters of the drug by at least about 50%. In another aspect of this embodiment, co-administration of a therapeutically effective amount of a compound of formula I improves at least one of the pharmacokinetic parameters of the drug by at least about 100%. In another aspect of this embodiment, co-administration of a therapeutically effective amount of a compound of formula I improves at least one of the pharmacokinetic parameters of the drug by at least about 200%. In another aspect of this embodiment, co-administration of a therapeutically effective amount of a compound of formula I improves at least one of the pharmacokinetic parameters of the drug by at least about 500%.

In another embodiment, the invention provides a method for increasing blood plasma levels of a drug which is metabolized by cytochrome P450 monooxygenase, comprising administering to a patient treated with said drug, a therapeutically effective amount of a compound of the invention, or a pharmaceutically acceptable salt thereof. In another aspect of this embodiment, co-administration of a therapeutically effective amount of a compound of formula I increases at least one of the blood plasma levels of the drug by at least about 10% to about 500%. In another aspect of this embodiment, co-administration of a therapeutically effective amount of a compound of formula I increases at least one of the blood plasma levels of the drug by at least about 10%. In another aspect of this embodiment, co-administration of a therapeutically effective amount of a compound of formula I increases at least one of the blood plasma levels of the drug by at least about 25%. In another aspect of this embodiment, co-administration of a therapeutically effective amount of a compound of formula I increases at least one of the blood plasma levels of the drug by at least about 50%. In another aspect of this embodiment, co-administration of a therapeutically effective amount of a compound of formula I increases at least one of the blood plasma levels of the drug by at least about 100%. In another aspect of this embodiment, co-administration of a therapeutically effective amount of a compound of formula I increases at least one of the blood plasma levels of the drug by at least about 200%. In another aspect of this embodiment, co-administration of a therapeutically effective amount of a compound of formula I increases at least one of the blood plasma levels of the drug by at least about 500%.

In another embodiment, the invention provides a method for increasing blood plasma levels of a drug which is metabolized by cytochrome P450 monooxygenase, comprising administering to a patient treated with said drug, a therapeutically effective amount of a combination comprising said drug and a compound of the present invention, or a pharmaceutically acceptable salt thereof. In another aspect of this embodiment, the therapeutically effective amount of the combination increases at least one of the blood plasma levels of the drug by at least about 10% to about 500%. In another aspect of this embodiment, the therapeutically effective amount of the combination increases at least one of the blood plasma levels of the drug by at least about 10%. In another aspect of this embodiment, the therapeutically effective amount of the combination increases at least one of the blood plasma levels of the drug by at least about 25%. In another aspect of this embodiment, the therapeutically effective amount of the combination increases at least one of the blood plasma levels of the drug by at least about 50%. In another aspect of this embodiment, the therapeutically effective amount of the combination increases at least one of the blood plasma levels of the drug by at least about 100%. In another aspect of this embodiment, the therapeutically effective amount of the combination increases at least one of the blood plasma levels of the drug by at least about 200%. In another aspect of this embodiment, the therapeutically effective amount of the combination increases at least one of the blood plasma levels of the drug by at least about 500%.

In another embodiment, the invention provides a method for increasing blood plasma levels of a drug which is metabolized by cytochrome P450 monooxygenase 3A, comprising administering to a patient treated with said drug, a therapeutically effective amount of a compound of the present invention, or a pharmaceutically acceptable salt thereof. In another aspect of this embodiment, co-administration of a therapeutically effective amount of a compound of formula I increases at least one of the blood plasma levels of the drug by at least about 10% to about 500%. In another aspect of this embodiment, co-administration of a therapeutically effective amount of a compound of formula I increases at least one of the blood plasma levels of the drug by at least about 10%. In another aspect of this embodiment, co-administration of a therapeutically effective amount of a compound of formula I increases at least one of the blood plasma levels of the drug by at least about 25%. In another aspect of this embodiment, co-administration of a therapeutically effective amount of a compound of formula I increases at least one of the blood plasma levels of the drug by at least about 50%. In another aspect of this embodiment, co-administration of a therapeutically effective amount of a compound of formula I increases at least one of the blood plasma levels of the drug by at least about 100%. In another aspect of this embodiment, co-administration of a therapeutically effective amount of a compound of formula I increases at least one of the blood plasma levels of the drug by at least about 200%. In another aspect of this embodiment, co-administration of a therapeutically effective amount of a compound of formula I increases at least one of the blood plasma levels of the drug by at least about 500%.

In another embodiment, the invention provides a method for increasing blood plasma levels of a drug which is metabolized by cytochrome P450 monooxygenase, comprising administering to a patient treated with said drug, a therapeutically effective amount of a compound of the invention, or a pharmaceutically acceptable salt thereof, and wherein the amount of the compound of the present invention administered is effective to inhibit cytochrome P450 monooxygenase. In another aspect of this embodiment, at least one of the blood plasma levels of the drug is increased by at least about 10% to about 500%. In another aspect of this embodiment, at least one of the blood plasma levels of the drug is increased by at least about 10%. In another aspect of this embodiment, at least one of the blood plasma levels of the drug is increased by at least about 25%. In another aspect of this embodiment, at least one of the blood plasma levels of the drug is increased by at least about 50%. In another aspect of this embodiment, at least one of the blood plasma levels of the drug is increased by at least about 100%. In another aspect of this embodiment, at least one of the blood plasma levels of the drug is increased by at least about 200%. In another aspect of this embodiment, at least one of the blood plasma levels of the drug is increased by at least about 500%.

In another embodiment, the invention provides a method for inhibiting cytochrome P450 monooxygenase in a patient comprising administering to a patient in need thereof an amount of a compound of the invention, or a pharmaceutically acceptable salt thereof, effective to inhibit cytochrome P450 monooxygenase.

In another embodiment, the invention provides a method for inhibiting cytochrome P450 monooxygenase 3A in a patient comprising administering to a patient in need thereof an amount of a compound of the invention, or a pharmaceutically acceptable salt thereof, effective to inhibit cytochrome P450 monooxygenase 3A.

In another embodiment, the invention provides a method for inhibiting cytochrome P450 monooxygenase comprising contacting cytochrome P450 monooxygenase with an amount of a compound of the invention, or a pharmaceutically acceptable salt thereof, effective to inhibit cytochrome P450 monooxygenase.

In another embodiment, the invention provides a method for inhibiting cytochrome P450 monooxygenase 3A comprising contacting cytochrome P450 monooxygenase 3A with an amount of a compound of the invention, or a pharmaceutically acceptable salt thereof, effective to inhibit cytochrome P450 monooxygenase 3A.

In another embodiment, the invention provides a method for treating an HIV infection comprising administering to a patient in need thereof a therapeutically effective amount of a compound of the present invention, or a pharmaceutically acceptable salt thereof, in combination with a therapeutically effective amount of one or more additional therapeutic agents selected from the group consisting of consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors and other drugs for treating HIV.

In another embodiment, the invention provides a method for treating an HCV infection comprising administering to a patient in need thereof a therapeutically effective amount of the present invention, or a pharmaceutically acceptable salt thereof, in combination with a therapeutically effective amount of one or more additional therapeutic agents selected from the group consisting of interferons, ribavirin analogs, NS3 protease inhibitors, alpha-glucosidase 1 inhibitors, hepatoprotectants, non-nucleoside inhibitors of HCV, and other drugs for treating HCV.

In another embodiment, the invention provides for the use of a compound of the invention, or a pharmaceutically acceptable salt thereof, for the preparation of a medicament for inhibiting cytochrome P450 monooxygenase in a patient.

In another embodiment, the invention provides for the use of a compound of the invention, or a pharmaceutically acceptable salt thereof, for the preparation of a medicament for inhibiting cytochrome P450 monooxygenase 3A in a patient.

EXAMPLES

Exemplary methods for preparing the compounds of formula (I) are provided below. These methods are intended to illustrate the nature of such preparations and are not intended to limit the scope of applicable methods. While the examples specify certain reaction conditions, one skilled in the art will understand how to vary the specific reaction conditions to obtain the full scope of the invention.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example; boiling point and molecular weight for distillation and sublimation, presence or absence of polar functional groups for chromatography, stability of materials in acidic and basic media in multiphase extractions; and the like. One skilled in the art will apply techniques most likely to achieve the desired separation.

It will be appreciated that synthetic intermediates may bear one or more protecting groups.

Example 1

Preparation of Compound 5

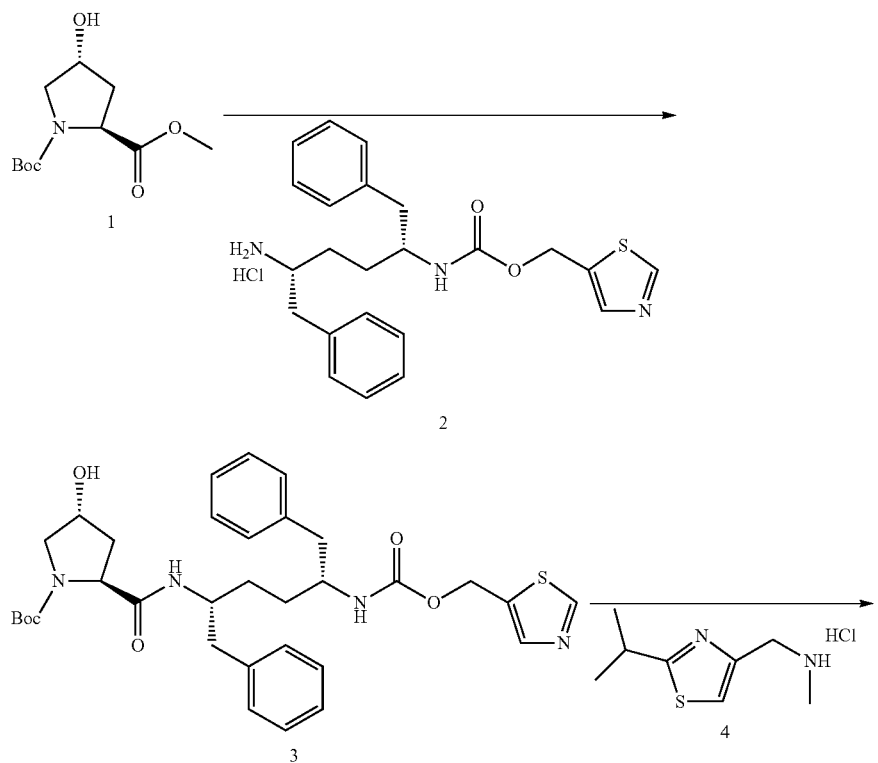

-continued

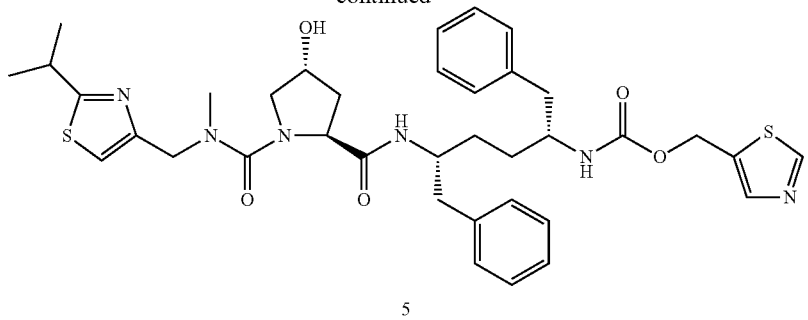

5

Compound 3 (150 mg, 0.24 mmol) was dissolved in DCM and 4N HCl in dioxane was added. The reaction material was allowed to stir for 30-45 minutes and then concentrated under reduced pressure and dried to give the corresponding Boc-deprotected proline.

Triphosgene (26 mg, 0.09 mmol) was dissolved in anhydrous DCM (3 mL) and stirred under nitrogen in an ice bath. Compound 4 (49 mg, 0.29 mmol) was mixed with DIPEA (84 µL, 0.48 mmol) in anhydrous DCM (2 mL) and then added dropwise to the triphosgene solution over 30-45 minutes and further stirred for 30 minutes after the addition was complete. The above proline material was dissolved in a small amount of anhydrous DMF and mixed with DIPEA (84 uL, 0.48 mmol). This was added to the reaction in one portion which was allowed reaction to warm to room temperature and stir for 16 hours. The reaction material was diluted with EtOAc and washed with saturated aqueous sodium bicarbonate solution (3×) and saturated sodium chloride solution. The organic extract was dried over anhydrous sodium sulfate and concentrated under reduced pressure. The material was purified with CombiFlash (0-10% MeOH in DCM) and then prep $C_{18}$ HPLC to give compound 5 (28 mg, 16%). $^1$H NMR (CD$_3$OD): δ 8.98 (s, 1H), 7.83 (s, 1H), 7.50 (m, 1H), 7.18 (m, 10H), 5.21 (m, 2H), 4.52 (m, 3H), 4.27 (m, 1H), 4.05 (m, 1H), 3.76 (m, 1H), 3.60 (m, 1H), 3.32 (m, 2H), 2.87 (s, 3H), 2.68 (m, 4H), 2.02 (m, 1H), 1.50 (m, 5H), 1.39 (d, J=6.9 Hz, 6H). Mass Spectrum (m/e): (M+H)$^+$ 719.2, (M−H)$^-$ 716.9.

Preparation of Compound 3

Commercially available (Aldrich) compound 1 (490 mg, 2 mmol) was dissolved in MeOH. NaOH (88 mg, 2.2 mmol) was dissolved in water and added to the reaction and stirred for 4 hours. The reaction was acidified to pH 3 with aqueous citric acid and then extracted with EtOAc (4×). The extracts were dried over anhydrous sodium sulfate and concentrated under reduced pressure. The material was dissolved in anhydrous DMF (10 mL) and HOBt (306 mg, 2 mmol) and compound 2 (1.3 g, 3 mmol), prepared by the method described in PCT/US2008/054788, was added. EDC (0.444 mL, 3 mmol) was added and the reaction was stirred for 10 minutes. TEA (1.1 mL, 8 mmol) was added and the material was stirred for 4 hours. The reaction material was diluted with EtOAc and washed with saturated aqueous sodium bicarbonate solution (3×) and saturated sodium chloride solution. The organic extracts were dried over anhydrous sodium sulfate and concentrated under reduced pressure. The material was purified with CombiFlash (0-10% MeOH in DCM) to give compound 3 (820 mg, 66%). Mass Spectrum (m/e): (M+H)$^+$ 623.0, (M−H)$^-$ 621.0.

Example 2

Preparation of Compound 8

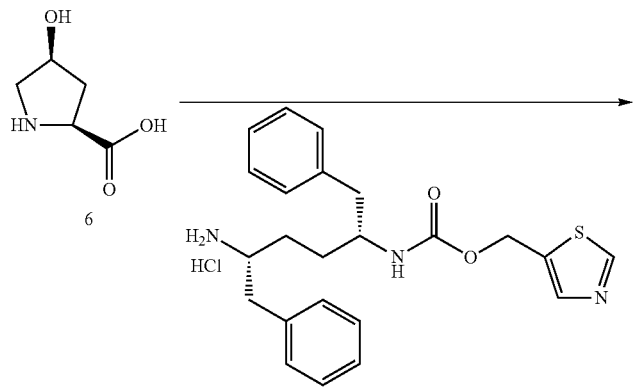

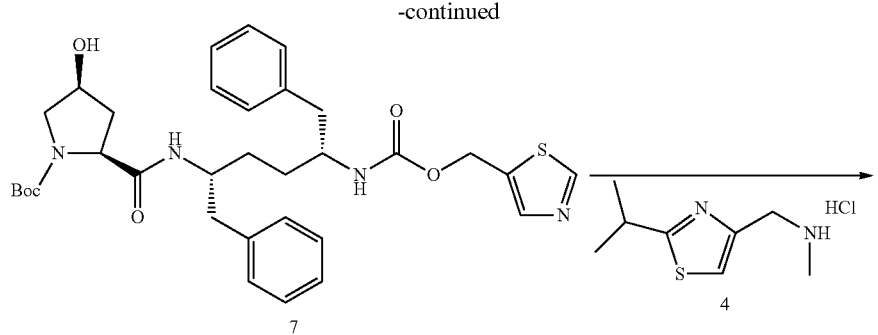

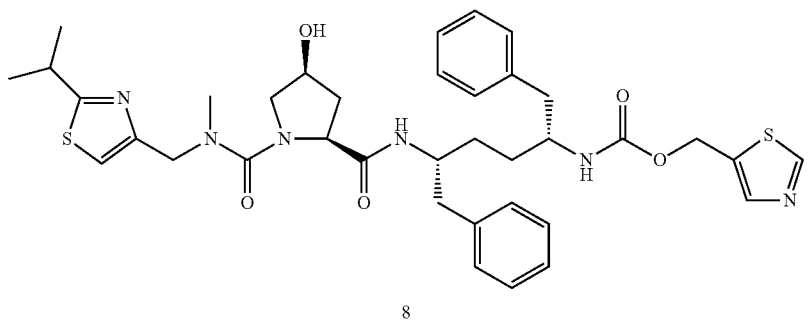

Compound 7 (345 mg, 0.55 mmol) was dissolved in DCM (3 mL) and 4N HCl in dioxane (3 mL) was added. The material was allowed to stir for 45 minutes and was then concentrated under reduced pressure. The material was dissolved in EtOAc and washed with saturated aqueous sodium bicarbonate solution (3×) and saturated sodium chloride solution. The organic extracts were dried over anhydrous sodium sulfate and concentrated under reduced pressure to give the corresponding Boc-deprotected proline.

Triphosgene (59 mg, 0.2 mmol) was dissolved in anhydrous DCM (5 mL) and stirred under nitrogen in an ice bath. Compound 4 was mixed (113 mg, 0.67 mmol) with DIPEA (193 μL, 1.11 mmol) in anhydrous DCM (2 mL) and then added dropwise to the triphosgene solution over 40 minutes. The above proline material was dissolved in anhydrous DCM (2 mL) and mixed with DIPEA (0.193 mL, 1.11 mmol) and added to the reaction in one portion. The reaction was allowed to warm to room temperature and stir for 16 hours. The reaction material was concentrated under reduced pressure, dissolved with EtOAc and washed with saturated aqueous sodium bicarbonate solution (3×) and saturated sodium chloride solution. The organic extracts were dried over anhydrous sodium sulfate and concentrated under reduced pressure. The material was purified with CombiFlash (0-10% MeOH in DCM) and then prep $C_{18}$ HPLC to give compound 8 (209 mg, 53%). $^1$H NMR (CD$_3$OD): δ 8.98 (s, 1H), 7.82 (s, 1H), 7.18 (m, 11H), 5.21 (m, 2H), 4.43 (m, 3H), 4.25 (m, 1H), 4.03 (m, 1H), 3.69 (m, 2H), 3.31 (m, 2H), 2.85 (s, 3H), 2.71 (m, 4H), 2.30 (m, 1H), 1.72 (m, 1H), 1.48 (m, 4H), 1.39 (d, J=6.9 Hz, 6H). Mass Spectrum (m/e): (M+H)$^+$ 719.2, (M−H)$^−$ 716.8.

Preparation of Compound 7

Commercially available (Aldrich) compound 6 (525 mg, 4 mmol) was dissolved in water (10 mL) and THF (5 L). NaOH (aq) was added to give pH 9-10. Boc anhydride (959 mg, 4.4 mmol) was dissolved in THF (2 mL) and added to the reaction dropwise. The reaction was maintained at a pH 9-10 with NaOH (aq). Upon completion, the reaction was acidified to pH of 3 with dilute HCl (aq) and extracted with EtOAc (2×). The organic extracts were dried over anhydrous sodium sulfate and concentrated under reduced pressure to give a Boc-protected proline (compound 6a) as a solid. This solid was washed with hexanes (3×) and dried under high vacuum to give the intermediate (882 mg, 95%) which was then dissolved in anhydrous DMF (5 mL). HOBt (641 mg, 4.18 mmol) and EDAC (874 mg, 4.56 mmol) were added and stirred for 15 minutes. Compound 2 (1.87 g, 4.2 mmol) and TEA (1.1 ml, 7.6 mmol) were added and the reaction was stirred for 4 hours. The reaction material was diluted with EtOAc and washed with saturated aqueous sodium bicarbonate solution (3×) and saturated aqueous sodium chloride solution. The organic extracts were dried over anhydrous sodium sulfate and concentrated under reduced pressure. The material was purified with CombiFlash (0-10% MeOH in DCM) to give compound 7 (345 mg, 15%). Mass Spectrum (m/e): (M+H)$^+$ 623.1, (M−H)$^−$ 620.6.

Example 3

Preparation of Compound 11

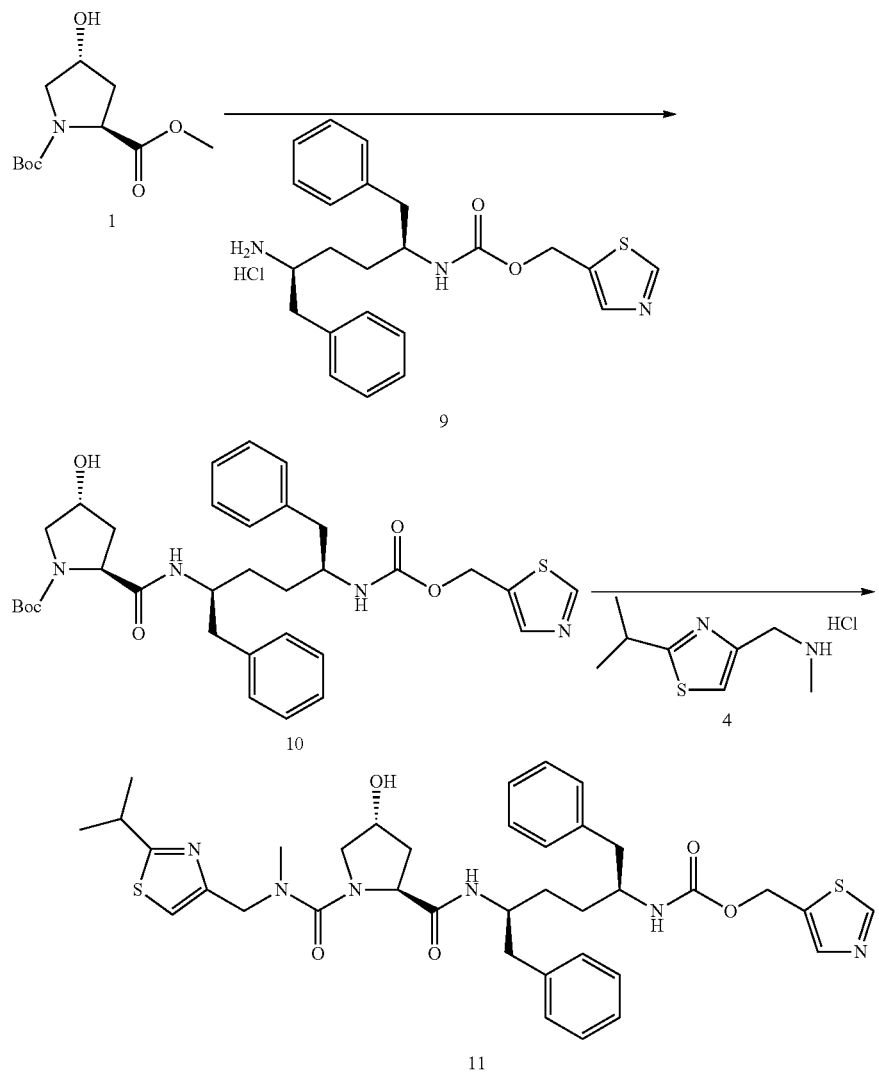

Compound 10 (730 mg, 1.17 mmol) was dissolved in DCM (10 mL) and TFA (2.5 mL) was added and stirred for 3 hours. The reaction mixture was concentrated under reduced pressure, dissolved in EtOAc and washed with saturated aqueous sodium bicarbonate solution (3×) and saturated sodium chloride solution. The organic extract was dried over anhydrous sodium sulfate and concentrated under reduced pressure to give the corresponding Boc-deprotected proline.

Triphosgene (31 mg, 0.1 mmol) was dissolved in anhydrous DCM (2 mL) and stirred under nitrogen in an ice bath. Compound 4 (59 mg, 0.345 mmol) was mixed with DIPEA (0.10 mL, 0.574 mmol) in anhydrous DCM (2 mL) and then added dropwise to the triphosgene solution over 10 minutes. The above proline material (150 mg, 0.287 mmol) was dissolved in anhydrous DCM (2 mL) and mixed with DIPEA (0.10 mL, 0.574 mmol) and added to the reaction in one portion. The reaction was allowed to warm to room temperature and stir for 16 hours. The reaction material was concentrated under reduced pressure, dissolved with EtOAc and washed with saturated aqueous sodium bicarbonate solution (2×) and saturated sodium chloride solution. The organic extracts were dried over anhydrous sodium sulfate and concentrated under reduced pressure. The material was purified with CombiFlash (0-10% MeOH in DCM) to give compound 11 (58 mg, 28%). $^1$H NMR (CD$_3$OD): δ 8.97 (s, 1H), 7.83 (m, 2H), 7.17 (m, 11H), 5.20 (m, 2H), 4.47 (m, 3H), 4.27 (m, 1H), 4.18 (m, 1H), 3.79 (m, 1H), 3.64 (m, 1H), 3.32 (m, 2H), 2.88 (s, 3H), 2.66 (m, 4H), 1.91 (m, 1H), 1.48 (m, 4H), 1.34 (d, J=6.9 Hz, 6H).

Mass Spectrum (m/e): (M+H)$^+$ 719.1, (M−H)$^-$ 717.0.

Preparation of compound 10

Compound 1 (490 mg, 2 mmol) was dissolved in MeOH (10 mL). NaOH (88 mg, 2.2 mmol) was dissolved in water (5 mL) then added to the reaction and stirred for 6 hours. The reaction was acidified to pH 3 with 5% aqueous citric acid and then extracted with EtOAc (2×). The extracts were dried over anhydrous sodium sulfate and concentrated under reduced pressure. The resulting acid was dissolved in anhydrous DMF (20 mL). HOBt (307 mg, 2 mmol) and compound 9 (892 mg, 2 mmol), prepared by the method described in PCT/US2008/054788, were added. EDAC (422 mg, 2.2 mmol) was added and the reaction was stirred for 30 minutes. DIPEA (1.2 mL, 7 mmol) was added and the reaction was stirred for 16 hours. The reaction material was diluted with EtOAc and washed with saturated aqueous sodium bicarbonate solution (3×) and saturated sodium chloride solution. The organic extracts were dried over anhydrous sodium sulfate and concentrated under reduced pressure. The material was purified with CombiFlash (0-10% MeOH in DCM) to give compound 10 (735 mg, 59%). Mass Spectrum (m/e): (M+H)+ 623.0, (M−H)− 620.8.

Example 4

Preparation of Compound 16 over anhydrous sodium sulfate and concentrated under reduced pressure to give the corresponding Boc-deprotected amine (0.96 g).

Triphosgene (30 mg, 0.1 mmol) was dissolved in anhydrous DCM (2 mL) and stirred under nitrogen in an ice bath. The above amine material (52 mg, 0.1 mmol) was dissolved in anhydrous DCM (2 mL) and mixed with DIPEA (34 μL, 0.2 mmol). The above amine solution was added dropwise to the triphosgene solution over 10 minutes and stirred for 35 minutes. Compound 4 (20 mg, 0.12 mmol) was mixed with DIPEA (34 μL, 0.2 mmol) in anhydrous DCM (2 mL) and then added to the reaction dropwise over 5 minutes. The reaction was allowed to warm to room temperature and stir for 48 hours. The reaction material was concentrated under reduced pressure, dissolved in EtOAc and washed with saturated aqueous sodium bicarbonate solution (2×) and saturated sodium chloride solution. The organic extracts were dried over anhydrous sodium sulfate and concentrated under reduced pressure. The crude material was purified with Prep

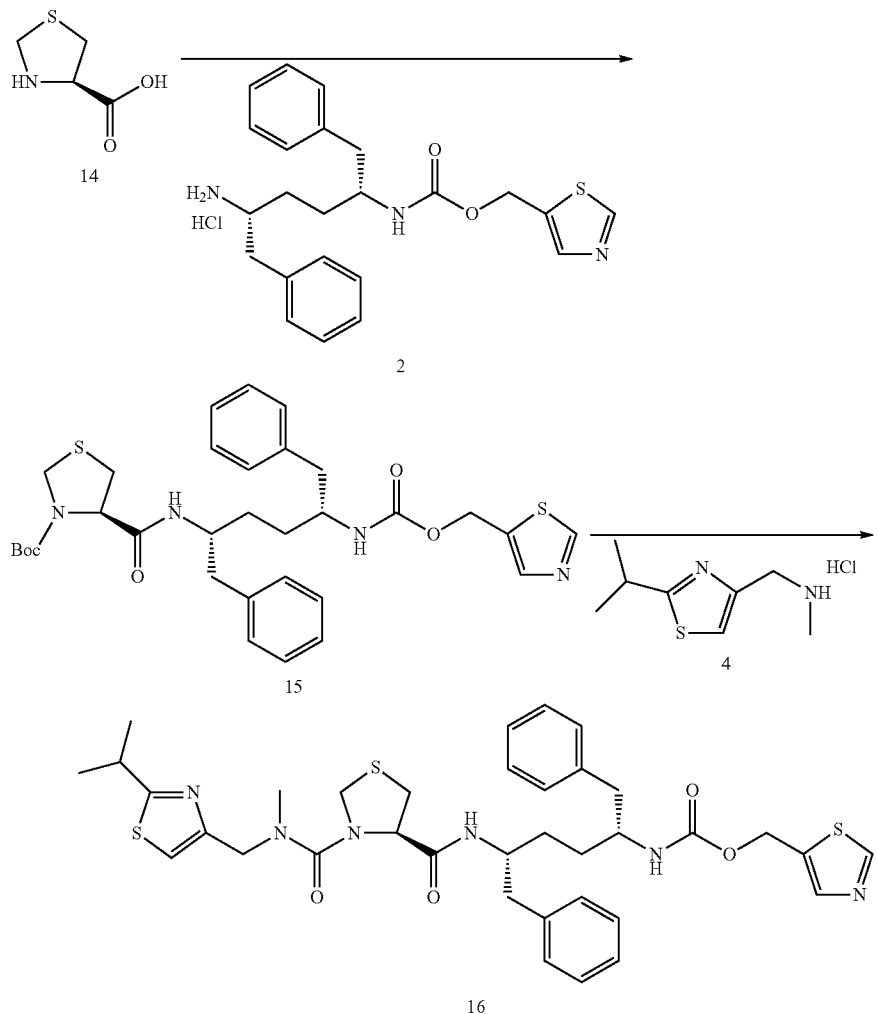

Compound 15 (1.18 g, 1.89 mmol) was dissolved in DCM (10 mL) and TFA (3 mL) was added. The reaction was stirred for 90 minutes and concentrated under reduced pressure. The solid was dissolved in EtOAc and washed with saturated aqueous sodium bicarbonate solution (3×) and saturated sodium chloride solution. The organic extracts were dried C18 HPLC to give compound 16 (25 mg, 35%). 1H NMR (CD3OD): δ 9.13 (s, 1H), 7.91 (s, 1H), 7.71 (m, 1H), 7.36 (s, 1H), 7.17 (m, 11H), 5.23 (m, 2H), 4.86 (m, 1H), 4.51 (m, 3H), 4.19 (m, 1H), 3.97 (m, 1H), 3.82 (m, 1H), 3.38 (m, 1H), 3.05 (m, 2H), 2.82 (s, 3H), 2.71 (m, 4H), 1.56 (m, 4H), 1.41 (m, 6H). Mass Spectrum (m/e): (M+H)+ 721.0, (M−H)− 718.8.

Preparation of Compound 15

Commercially available (Aldrich) compound 14 (1.33 g, 10 mmol) was dissolved in DCM and TEA (2.8 mL, 20 mmol). Boc anhydride (2.6 g, 12 mmol) was added in portions over 30 minutes. The reaction material was concentrated under reduced pressure to give an oil which was then washed with hexanes (4×). The material was dissolved in EtOAc and washed with aqueous citric acid solution. The organic extracts were dried over anhydrous sodium sulfate and concentrated under reduced pressure to give a solid (1.64 g, 70%). N-Boc-thiaproline (446 mg, 2 mmol) was dissolved in anhydrous DMF (10 mL) and HOBt (306 mg, 2 mmol) and EDAC (422 mg, 2.2 mmol) were added. The reaction was stirred for 30 minutes and compound 2 (892 mg, 2 mmol) and TEA (0.556 mL, 4 mmol) were added. The material was stirred for 90 minutes, diluted with EtOAc and washed with saturated aqueous sodium bicarbonate solution (2×) and saturated sodium chloride solution. The organic extracts were dried over anhydrous sodium sulfate and concentrated under reduced pressure. The crude material was purified with CombiFlash (0-5% MeOH in DCM) to give compound 15 (1.18 g, 95%). Mass Spectrum (m/e): (M+H)+ 625.0, (M−H)− 622.8.

Example 5

Preparation of Compound 18

Compound 17 (220 mg, 0.335 mmol) was dissolved in DCM (3 mL) and TFA (2 mL) was added. The reaction was stirred for 60 minutes and concentrated under reduced pressure. The reaction material was dissolved in EtOAc and washed with saturated aqueous sodium bicarbonate solution (3×) and saturated sodium chloride solution. The organic extracts were dried over anhydrous sodium sulfate and concentrated under reduced pressure to give the corresponding Boc-deprotected free amine.

Triphosgene (56 mg, 0.188 mmol) was dissolved in anhydrous DCM (2 mL) and stirred under nitrogen in an ice bath. The above amine material (52 mg, 0.1 mmol) was dissolved in anhydrous DCM (2 mL) and mixed with DIPEA (33 μL, 0.188 mmol). The above amine solution was added dropwise to the triphosgene solution over 10 minutes and allowed to stir for an additional 35 minutes. Compound 4 (64 mg, 0.376 mmol) was mixed with DIPEA (33 μL, 0.188 mmol) in anhydrous DCM (2 mL) and added to the reaction dropwise over 5 minutes. The reaction was allowed to warm to room temperature and stir for 64 hours. The reaction material was concentrated under reduced pressure, dissolved with EtOAc and washed with saturated aqueous sodium bicarbonate solution (2×) and saturated sodium chloride solution. The organic extracts were dried over anhydrous sodium sulfate and concentrated under reduced pressure. The crude material was purified with CombiFlash (0-10% MeOH in DCM) and then

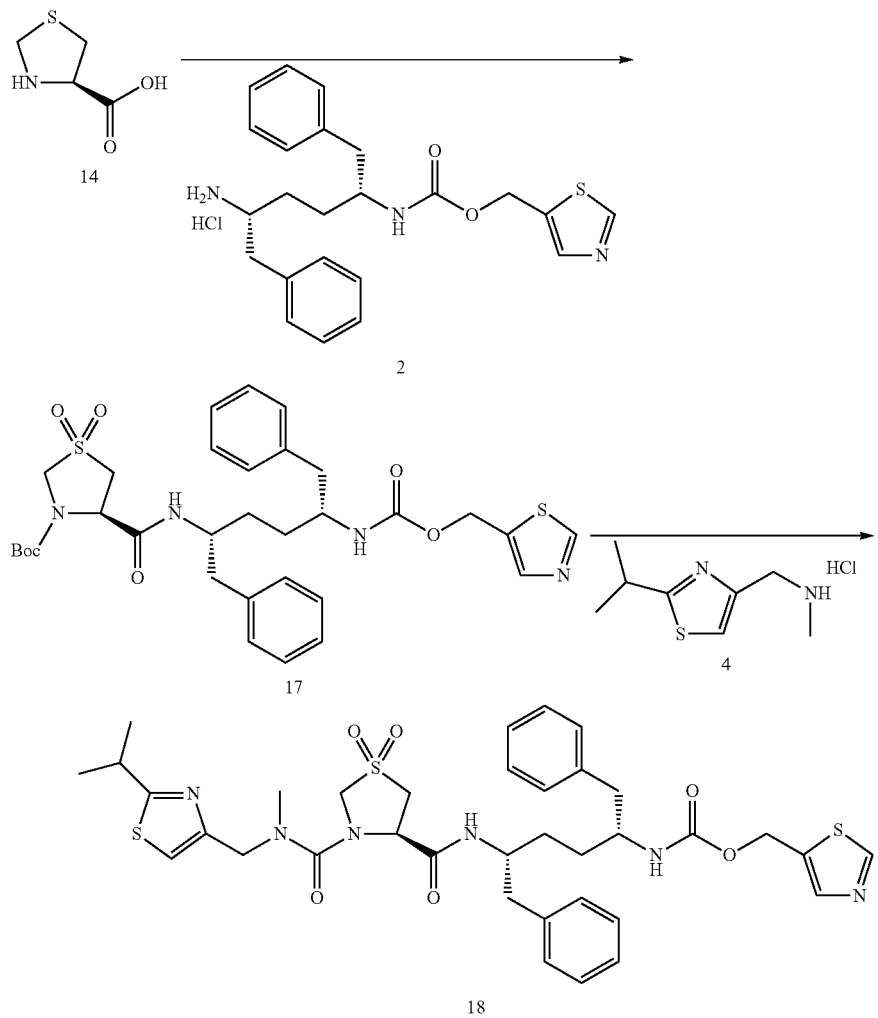

Prep C$_{18}$ HPLC to give compound 18 (17 mg, 12%). $^1$H NMR (CD$_3$OD): δ 8.98 (s, 1H), 7.84 (s, 1H), 7.29 (s, 1H), 7.16 (m, 10H), 5.23 (m, 2H), 5.19 (m, 1H), 4.75 (m, 1H), 4.38 (m, 2H), 4.22 (m, 1H), 3.82 (m, 1H), 3.34 (m, 3H), 2.82 (s, 3H), 2.72 (m, 4H), 1.58 (m, 4H), 1.39 (m, 6H). Mass Spectrum (m/e): (M+H)$^+$ 753.1, (M−H)$^-$ 750.8.

Preparation of Compound 17

Compound 14 (1.33 g, 10 mmol) was combined with DCM and TEA (2.8 mL, 20 mmol). Boc anhydride (2.6 g, 12 mmol) was added in portions over 30 minutes. The reaction was concentrated under reduced pressure to give an oil which was then washed with hexanes (4×). The material was dissolved in EtOAc and washed with aqueous citric acid solution. The organic extracts were dried over anhydrous sodium sulfate and concentrated under reduced pressure to give a solid (1.64 g, 70%). N-Boc-thiaproline (466 mg, 2 mmol) was dissolved in HOAc and stirred in an ice bath. 32% Peracetic acid (4.2 ml, 20 mmol) was added over 30 minutes and the reaction was stirred at room temperature for 16 hours. The reaction mixture was diluted with EtOAc and washed with saturated aqueous sodium chloride solution (5×). The organic extracts were dried over anhydrous sodium sulfate and concentrated under reduced pressure to give the sulfone acid (184 mg, 35%) which was then mixed with HOBt (106 mg, 0.69 mmol) and dissolved in anhydrous DMF (5 mL). EDAC (159 mg, 0.83 mmol) was added and stirred for 30 minutes. Compound 2 (310 mg, 0.69 mmol) and TEA (0.288 mL, 2.1 mmol) were then added and stirred for 2-3 hours. The reaction was then diluted with EtOAc and washed with saturated aqueous sodium bicarbonate solution (2×) and saturated sodium chloride solution. The organic extracts were dried over anhydrous sodium sulfate and concentrated under reduced pressure. The crude material was purified with CombiFlash (0-10% MeOH in DCM) to give compound 17 (220 mg, 49%). Mass Spectrum (m/e): (M+H)$^+$ 656.9, (M−H)$^-$ 654.8.

Example 6

Preparation of Compound 21

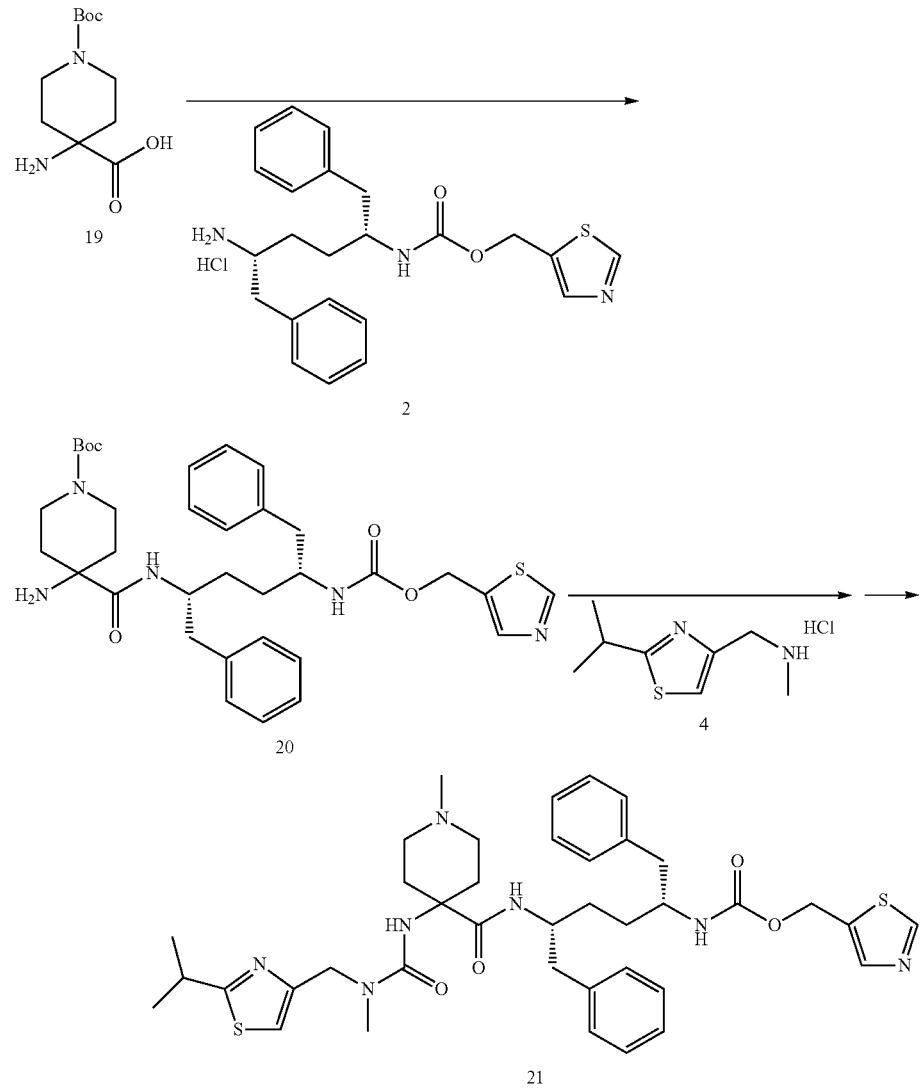

Triphosgene (28 mg, 0.094 mmol) was dissolved in anhydrous DCM (10 mL) and stirred under nitrogen in an ice bath. Compound 20 (120 mg, 0.189 mmol) was dissolved in anhydrous DCM (5 mL) and mixed with DIPEA (33 µL, 0.189 mmol) and added dropwise to the triphosgene solution over 15-20 minutes. The mixture was stirred for an additional 60 minutes. Compound 4 (45 mg, 0.378 mmol) was mixed with DIPEA (33 µL, 0.188 mmol) in anhydrous DCM (3 mL) and added to the reaction in one portion. The reaction mixture was allowed to warm to room temperature and stir for 16 hours. Additional compound 4 (45 mg, 0.378 mmol) with DIPEA (33 µL, 0.188 mmol) was added and stirred at 40° C. for 4 hours. The reaction material was concentrated under reduced pressure, dissolved with EtOAc and washed with saturated aqueous sodium bicarbonate solution (2×) and saturated sodium chloride solution. The organic extracts were dried over anhydrous sodium sulfate and concentrated under reduced pressure. The crude material was purified with Prep $C_{18}$ HPLC to give the desired intermediate (40 mg, 25%).

The intermediate was dissolved in small amount of MeOH and 4N HCl in dioxane (5 mL) was added. After stirring for 1 hour the mixture was concentrated under reduced pressure. The resulting material was dissolved in MeOH and $CH_3CN$ and 37% aqueous formaldehyde solution (18 µL, 0.24 mmol) and HOAc (5.5 µL, 0.096 mmol) were added. The reaction material was stirred for 15 minutes and $NaBH(OAc)_3$ (20 mg, 0.096 mmol) was added. After 1 hour of stirring additional formaldehyde solution and $NaBH(OAc)_3$ were added. The reaction material was then concentrated under reduced pressure, dissolved with EtOAc and washed with saturated aqueous sodium bicarbonate solution (2×) and saturated sodium chloride solution. The organic extracts were dried over anhydrous sodium sulfate and concentrated under reduced pressure. The crude material was purified with Prep $C_{18}$ HPLC to give compound 21 (30 mg, 84%). $^1$H NMR ($CD_3OD$): δ 8.97 (s, 1H), 7.81 (s, 1H), 7.47 (m, 1H), 7.17 (m, 11H), 6.79 (m, 1H), 5.20 (m, 2H), 4.55 (s, 2H), 4.18 (m, 1H), 3.78 (m, 1H), 3.32 (m, 2H), 2.97 (m, 6H), 2.72 (m, 7H), 2.16 (m, 4H), 1.54 (m, 4H), 1.36 (d, J=6.9 Hz, 6H). Mass Spectrum (m/e): $(M+H)^+$ 746.2, $(M-H)^-$ +HOAc 804.1.

Preparation of Compound 20

Commercially available compound 19 (244 mg, 1 mmol) with HOBt (153 mg, 1 mmol) and compound 2 (446 mg, 1 mmol) were combined in anhydrous DMF (10 mL). EDAC (210 mg, 1.1 mmol) was added and the reaction was stirred for 45 minutes. TEA (350 µL, 2.5 mmol) was added and the reaction was stirred for an additional 16 hours. The reaction material was diluted with EtOAc and washed with saturated aqueous sodium bicarbonate solution (2×) and saturated sodium chloride solution. The organic extracts were dried over anhydrous sodium sulfate and concentrated under reduced pressure. The crude material was purified with CombiFlash (0-5% MeOH in DCM) and then Prep $C_{18}$ HPLC to give compound 20 (120 mg, 19%). Mass Spectrum (m/e): $(M+H)^+$ 636.0, $(M-H)^-$ 633.9.

Example 7

Preparation of Compound 24 and Compound 25

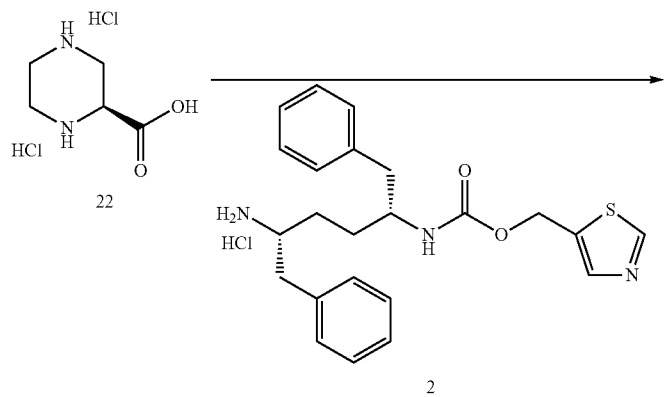

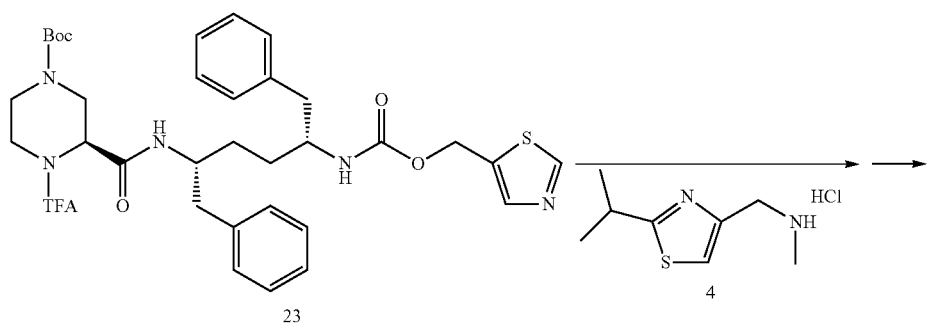

-continued

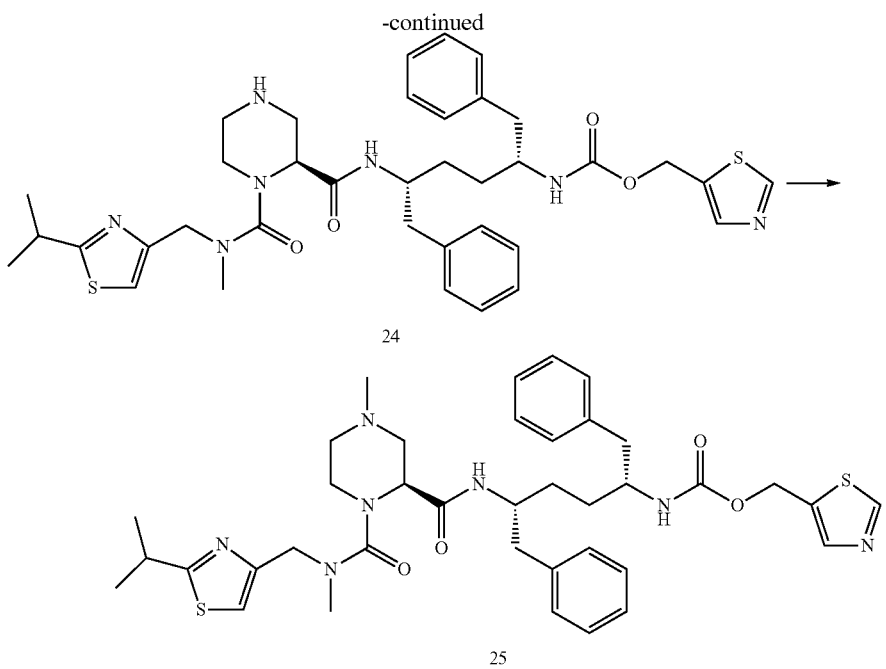

Compound 24 (20 mg, 0.024 mmol) was dissolved in MeOH and CH$_3$CN. 37% Aqueous formaldehyde solution (18 μL, 0.24 mmol) and HOAc (2.7 μL, 0.048 mmol) were added and the reaction was allowed to stir for 30 minutes. NaBH(OAc)$_3$ (25 mg, 0.12 mmol) was added and the reaction was stirred for 1 hour. Additional formaldehyde solution and NaBH(OAc)$_3$ were added and the reaction was stirred for 45 minutes. The reaction material was concentrated under reduced pressure, dissolved with EtOAc and washed with saturated aqueous sodium bicarbonate solution (2×) and saturated sodium chloride solution. The organic extracts were dried over anhydrous sodium sulfate and concentrated under reduced pressure to give compound 25 (15 mg, 85%). $^1$H NMR (CD$_3$OD): δ 8.97 (s, 1H), 7.82 (s, 1H), 7.17 (m, 11H), 5.21 (m, 2H), 4.40 (s, 2H), 4.16 (m, 2H), 4.07 (m, 1H), 3.79 (m, 1H), 3.37 (m, 1H), 3.10 (m, 1H), 2.95 (m, 1H), 2.79 (s, 3H), 2.72 (m, 4H), 2.50 (m, 1H), 2.23 (m, 5H), 1.54 (m, 4H), 1.38 (d, J=6.9 Hz, 6H). Mass Spectrum (m/e): (M+H)$^+$ 732.2, (M–H)$^-$ 730.1.

Preparation of Compound 24

Preparation of compound 23: Commercially available (Fluka) compound 22 (0.897 g, 4.4 mmol) was mixed with dioxane (5 mL) and water (5 mL). NaOH (528 mg, 13.2 mmol) was dissolved in water (5 mL) and added to above mixture to give a pH of 10. Boc anhydride (1.06 g, 4.86 mmol) was dissolved in dioxane (5 mL) and added to the reaction in portions while maintaining reaction at pH of 10 with NaOH (aq). The reaction was stirred for 16 hours and then concentrated under reduced pressure. The resulting material was mixed with EtOH (30 mL), EtOTFA was added (1.6 mL, 13.2 mmol) and the reaction was allowed to stir at 70° C. for 16 hours. Additional EtOTFA (1.6 mL, 13.2 mmol) was added and the reaction was stirred for an additional 24 hours. The reaction material was concentrated under reduced pressure, dissolved with EtOAc and washed with citric acid solution (2×) and saturated sodium chloride solution. The organic extracts were dried over anhydrous sodium sulfate and concentrated under reduced pressure. The material was purified with CombiFlash (0-10% MeOH in DCM) and then Prep C$_{18}$ HPLC to give the intermediate acid (240 mg, 17%).

The resulting acid was then dissolved in anhydrous DMF (5 mL). HOBt (113 mg, 0.736 mmol) and EDAC (155 mg, 0.81 mmol) were added and the reaction was stirred for 45 minutes. Compound 2 (328 mg, 0.736 mmol) and TEA (256 μL, 1.84 mmol) were added and after 3 hours of stirring the reaction was diluted with EtOAc and washed with saturated aqueous sodium bicarbonate solution (2×) and saturated sodium chloride solution. The organic extracts were dried over anhydrous sodium sulfate and concentrated under reduced pressure. The material was purified with CombiFlash (0-5% MeOH in DCM) to give compound 23 (476 mg, 90%). Mass Spectrum (m/e): (M+H)$^+$ 718.0, (M–H)$^-$ 716.1.

Preparation of compound 24: Compound 23 (476 mg, 0.564 mmol) was dissolved in MeOH (5 mL) and water (2 mL). 1M NaOH (aq) was added to give a pH of 13-14 and the reaction was stirred for 90 minutes. The reaction material was diluted with saturated aqueous sodium bicarbonate solution and extracted with EtOAc. The organic extracts were washed with saturated aqueous sodium bicarbonate solution (2×) and saturated sodium chloride solution, dried over anhydrous sodium sulfate and concentrated under reduced pressure. The crude material was purified with CombiFlash (0-5% MeOH in DCM) to give TFA-deprotected amine.

Triphosgene (167 mg, 0.564 mmol) was dissolved in anhydrous DCM (10 mL) and stirred under nitrogen in an ice bath. Compound 4 (102 mg, 0.845 mmol) was mixed with TEA (78 μL, 0.564 mmol) in anhydrous DCM (5 mL) and was then added dropwise to the triphosgene solution over 15-20 minutes. The reaction material was stirred for 45 minutes. The free amine from above (350 mg, 0.564 mmol) was dissolved in anhydrous DCM (5 mL) and mixed with TEA (78 μL, 0.564 mmol) and added to the reaction in one portion. The reaction was allowed to warm to room temperature and stir for an additional 16 hours. The reaction was then stirred at 40° C. for 16 hours. The reaction material was then concentrated under reduced pressure, dissolved with EtOAc and washed with saturated aqueous sodium bicarbonate solution (2×) and saturated sodium chloride solution. The organic extracts were dried over anhydrous sodium sulfate and concentrated under reduced pressure. The crude material was purified with Prep C$_{18}$ HPLC to give the desired intermediate (40 mg, 9%). The resulting material was dissolved in a small amount of MeOH and 4N HCl in dioxane (3 mL) was added. The reaction was stirred for 30 minutes and concentrated under reduced pressure. The crude material was purified with Prep C$_{18}$ HPLC to give compound 24 (30 mg, 85%). $^1$H NMR (CD$_3$OD): δ 8.97 (s, 1H), 7.83 (s, 1H), 7.16 (m, 1H), 5.22 (m, 2H), 4.38 (m, 2H), 4.22 (m, 1H), 4.07 (m, 1H), 3.81 (m, 1H), 3.18 (m, 2H), 2.79 (s, 3H), 2.70 (m, 8H), 1.56 (m, 4H), 1.38 (d, J=6.9 Hz, 6H). Mass Spectrum (m/e): (M+H)$^+$ 718.1, (M−H)$^-$ 716.1.

Example 8

Preparation of Compound 29 and Compound 30

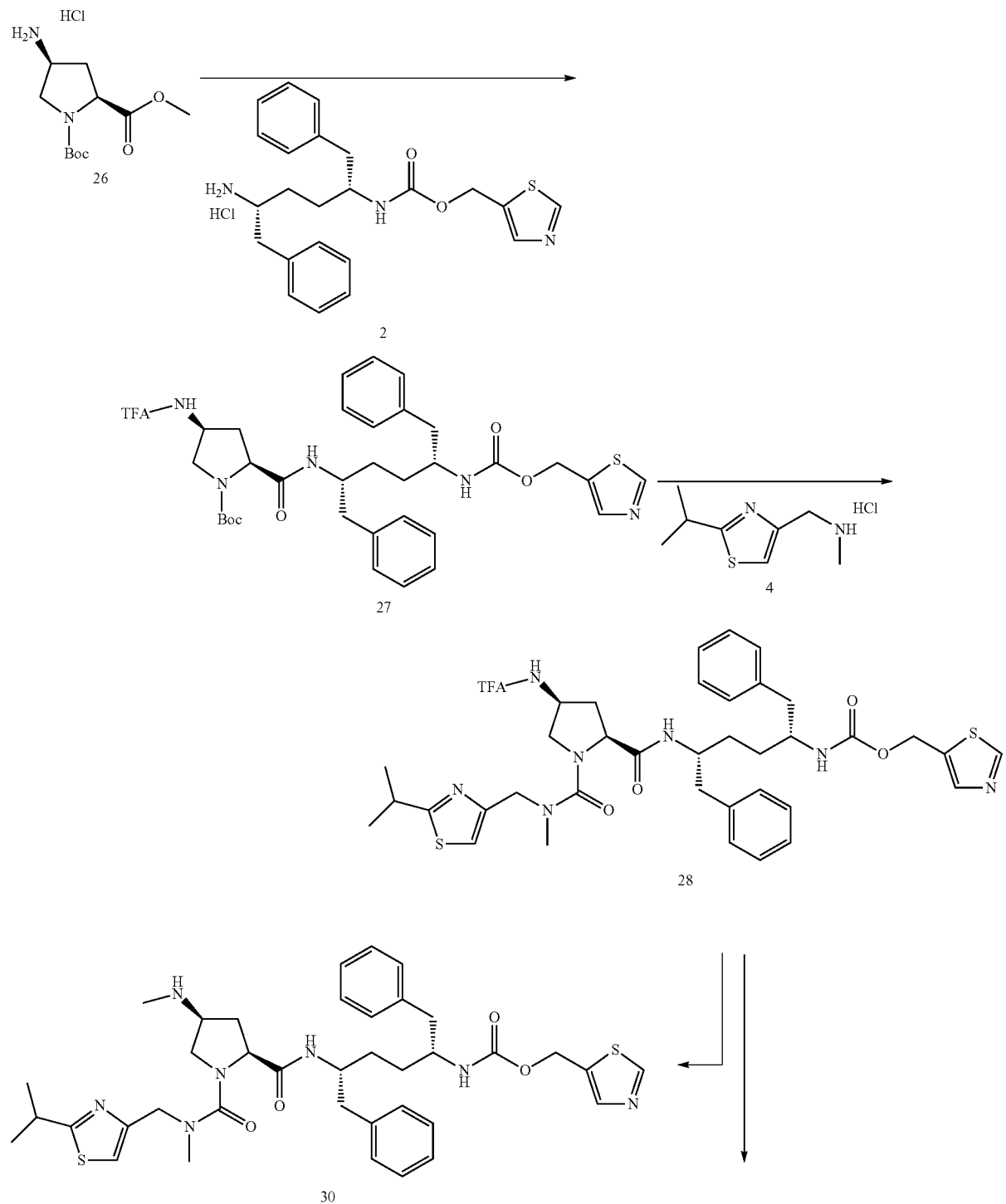

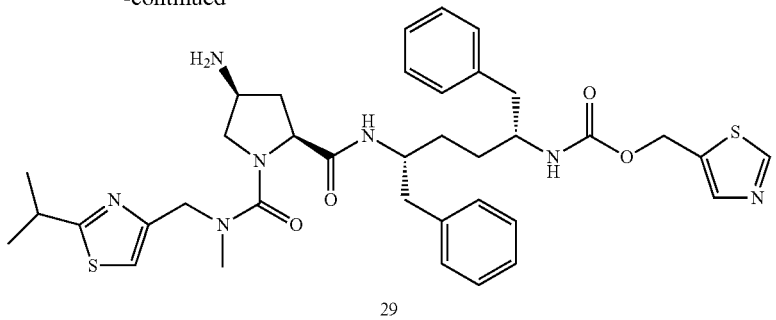

29

Preparation of compound 29: Compound 28 (225 mg, 0.276 mmol) was dissolved in MeOH and water. 1N NaOH (aq) was added to give a pH of 13. The reaction was stirred for 16 hours. The pH was adjusted to 10 with dilute HCl(aq). The reaction material was concentrated in reduced pressure, dissolved with EtOAc and washed saturated aqueous sodium bicarbonate solution (3×) and saturated sodium chloride solution. The organic extracts were dried over anhydrous sodium sulfate and concentrated under reduced pressure to give compound 29 (172 mg, 87%). $^1$H NMR (CD$_3$OD): δ 8.98 (s, 1H), 7.83 (s, 1H), 7.19 (m, 11H), 5.21 (m, 2H), 4.52 (m, 3H), 4.04 (m, 1H), 3.68 (m, 2H), 3.19 (m, 3H), 2.86 (s, 3H), 2.75 (m, 5H), 1.31 (m, 1H), 1.48 (m, 5H), 1.38 (d, J=6.9 Hz, 6H). Mass Spectrum (m/e): (M+H)$^+$ 718.1, (M−H)$^-$ 716.0.

Preparation of compound 30: Compound 28 (50 mg, 0.07 mmol) was dissolved in anhydrous DMF (2 mL). K$_2$CO$_3$ (15 mg, 0.105 mmol) and MeI (5.2 μL, 0.084 mmol) were added and the reaction was stirred for 16 hours. The reaction mixture was then diluted with EtOAc and washed with saturated aqueous sodium bicarbonate solution (2×) and saturated sodium chloride solution. The organic extracts were dried over anhydrous sodium sulfate and concentrated under reduced pressure. The material was dissolved in MeOH and water and NaOH (aq) was added to give a pH of 13. The reaction was stirred for 60 minutes. The pH was adjusted to 10 with HCl (aq). The reaction material was concentrated under reduced pressure and dissolved with EtOAc and washed with saturated aqueous sodium bicarbonate solution (3×) and saturated sodium chloride solution. The organic extracts were dried over anhydrous sodium sulfate and concentrated under reduced pressure. The crude material was purified with prep C$_{18}$ HPLC to give compound 30 (28 mg, 55%). $^1$H NMR (CD$_3$OD): δ 8.98 (s, 1H), 7.83 (s, 1H), 7.19 (m, 11H), 5.21 (m, 2H), 4.48 (m, 3H), 4.03 (m, 1H), 3.80 (m, 2H), 3.58 (m, 2H), 2.79 (s, 3H), 2.72 (m, 4H), 2.68 (s, 3H), 2.43 (m, 1H), 1.86 (m, 1H), 1.54 (m, 4H), 1.39 (d, J=6.9 Hz, 6H). Mass Spectrum (m/e): (M+H)$^+$ 732.2, (M−H)$^-$ +HOAc 790.0.

Preparation of Compound 28

Preparation of compound 27: Commercially available (CNH Technologies, Inc.) compound 26 (400 mg, 1.42 mmol) was dissolved in EtOH (10 mL) and water. NaOH (114 mg, 2.85 mmol) was dissolved in water (5 mL) then added to the reaction and stirred for 3 hours. HCl(aq) was added to give a pH of 9. The resulting reaction material was concentrated under reduced pressure and then mixed with EtOH. EtOTFA (844 μL, 7.1 mmol) and TEA (197 μL, 1.42 mmol) were added and the reaction was stirred at 45° C. for 16 hours. The reaction material was concentrated under reduced pressure, dissolved with EtOAc and washed with citric acid solution (2×) and saturated sodium chloride solution. The organic extracts were dried over anhydrous sodium sulfate and concentrated under reduced pressure to give the bis-protected acid (464 mg, 1.42 mmol). The resulting acid was then mixed with HOBt (222 mg, 1.45 mmol) and EDAC (306 mg, 1.6 mmol) and dissolved in anhydrous DMF (15 mL). The reaction solution was stirred for 30 minutes and compound 2 (647 mg, 1.45 mmol) and TEA (504 μL, 3.63 mmol) were added. The reaction material was stirred for 2 hours and was then diluted with EtOAc and washed with saturated aqueous sodium bicarbonate solution (2×) and saturated sodium chloride solution. The organic extracts were dried over anhydrous sodium sulfate and concentrated under reduced pressure. The crude material was purified with CombiFlash (0-5% MeOH in DCM) to give compound 27 (757 mg, 74%). Mass Spectrum (m/e): (M+H)$^+$ 718.0, (M−H)$^-$ 716.0

Preparation of compound 28: Compound 27 (549 mg, 0.89 mmol) was dissolved in MeOH (2 mL) and 4N HCl in dioxane (5 mL) was added. The reaction material was stirred for 30-45 minutes and then concentrated in reduced pressure. The material was dissolved with EtOAc and washed with saturated aqueous sodium bicarbonate solution (2×) and saturated sodium chloride solution. The organic extracts were dried over anhydrous sodium sulfate and concentrated under reduced pressure to give the corresponding Boc-deprotected proline.

Triphosgene (158 mg, 0.534 mmol) was dissolved in anhydrous DCM (20 mL) and stirred under nitrogen in an ice bath. The above amine material was dissolved in DCM (10 mL) and mixed with DIPEA (155 μL, 0.89 mmol) and added dropwise to the triphosgene solution over 20 minutes. The reaction material was stirred for 60 minutes. Compound 4 (214 mg, 1.78 mmol) was mixed with DIPEA (155 μL, 0.89 mmol) in anhydrous DCM (5 mL) and then added to the reaction in one portion. The reaction was allowed to warm to room temperature and stir for 16 hours. The reaction material was then concentrated under reduced pressure, dissolved with EtOAc and washed with saturated aqueous sodium bicarbonate solution (3×) and saturated sodium chloride solution. The organic extracts were dried over anhydrous sodium sulfate and concentrated under reduced pressure. The crude material was purified with CombiFlash (0-5% MeOH in DCM) and then prep C$_{18}$ HPLC to give compound 28 (560 mg, 77%). Mass Spectrum (nil e): (M+H)$^+$ 814.1, (M−H)$^-$ 812.1.

Example 9

Preparation of Compound 31 and Compound 32

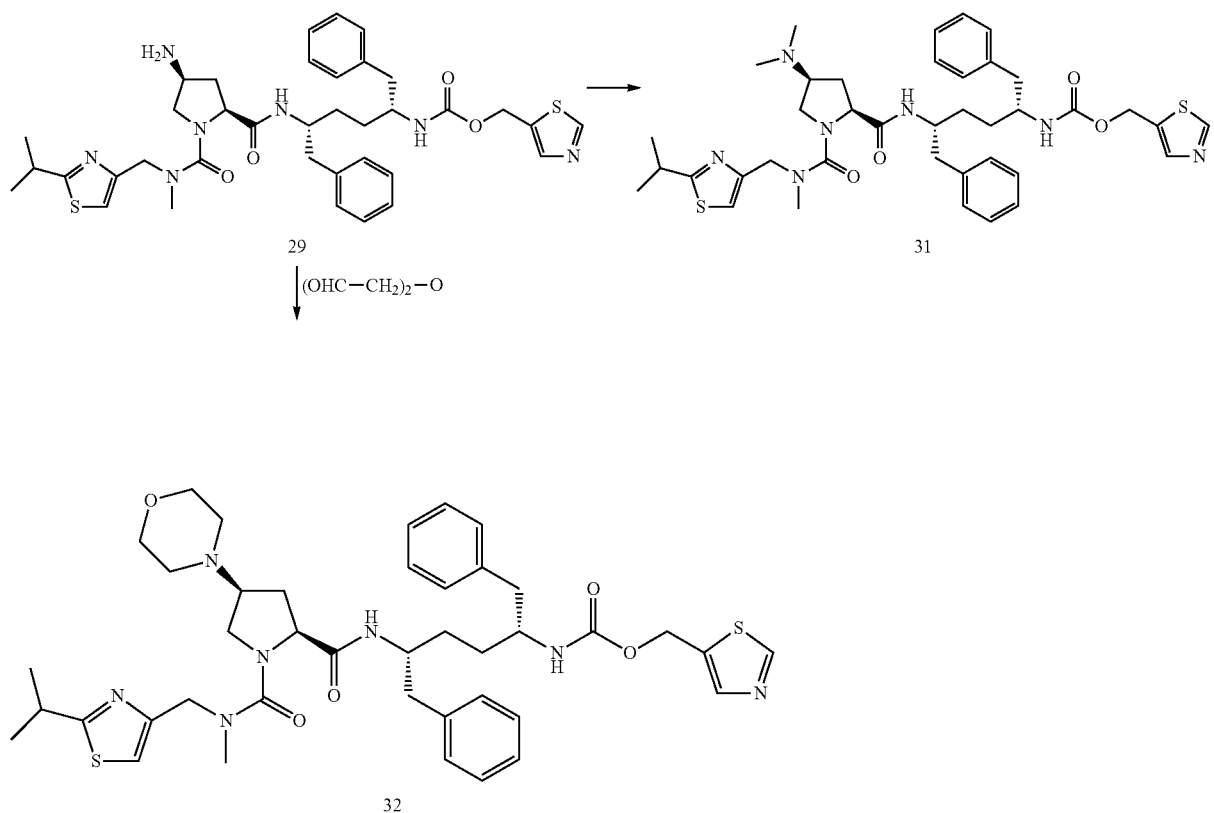

Preparation of compound 31: Compound 29 (50 mg, 0.07 mmol) was dissolved in CH$_3$CN. 37% Aqueous formaldehyde solution (104 µL, 1.39 mmol) and HOAc (8 µL, 0.139 mmol) were added and the reaction was stirred for 30 minutes. NaBH(OAc)$_3$ (148 mg, 0.7 mmol) was added and the reaction was stirred for 1 hour. Additional formaldehyde solution and NaBH(OAc)$_3$ were added and the reaction was stirred for 45 minutes. The reaction was diluted with EtOAc and washed with saturated aqueous sodium bicarbonate solution (2×) and saturated sodium chloride solution. The organic extracts were dried over anhydrous sodium sulfate and concentrated under reduced pressure. The crude material was purified with CombiFlash (0-5% MeOH in DCM) to give compound 31 (44 mg, 84%).

$^1$H NMR (CD$_3$OD): δ 8.97 (s, 1H), 7.82 (s, 1H), 7.19 (m, 11H), 5.21 (m, 2H), 4.48 (m, 3H), 4.03 (m, 1H), 3.76 (m, 2H), 2.86 (s, 3H), 2.73 (m, 5H), 2.30 (m, 1H), 2.24 (s, 6H), 1.52 (m, 5H), 1.39 (d, J=6.9 Hz, 6H). Mass Spectrum (m/e): (M+H)$^+$ 746.3, (M−H)$^-$ +HOAc 804.1.

Preparation of compound 32: Compound 29 (72 mg, 0.1 mmol) was dissolved in CH$_3$CN and water. The diadehyde (O(CH$_2$CHO)$_2$) (0.6 mmol) was added and the reaction was stirred for 15 minutes. NaBH$_3$CN (50 mg) and small amount of MeOH were added and the reaction was stirred for 16 hours. The reaction material was diluted with EtOAc and washed with saturated aqueous sodium bicarbonate solution (2×) and saturated sodium chloride solution. The organic extracts were dried over anhydrous sodium sulfate and concentrated under reduced pressure. The crude material was purified with prep C$_{18}$ HPLC to give compound 32 (40 mg, 51%). $^1$H NMR (CD$_3$OD): δ 8.98 (s, 1H), 7.83 (s, 1H), 7.45 (m, 1H), 7.19 (m, 10H), 5.21 (m, 2H), 4.48 (m, 3H), 4.05 (m, 1H), 3.68 (m, 6H), 2.85 (s, 3H), 2.72 (m, 5H), 2.42 (m, 5H), 1.52 (m, 5H), 1.39 (d, J=6.9 Hz, 6H). Mass Spectrum (m/e): (M+H)$^+$ 788.2, (M−H)$^-$ +HOAc 846.0.

Example 10

Preparation of Compound 35

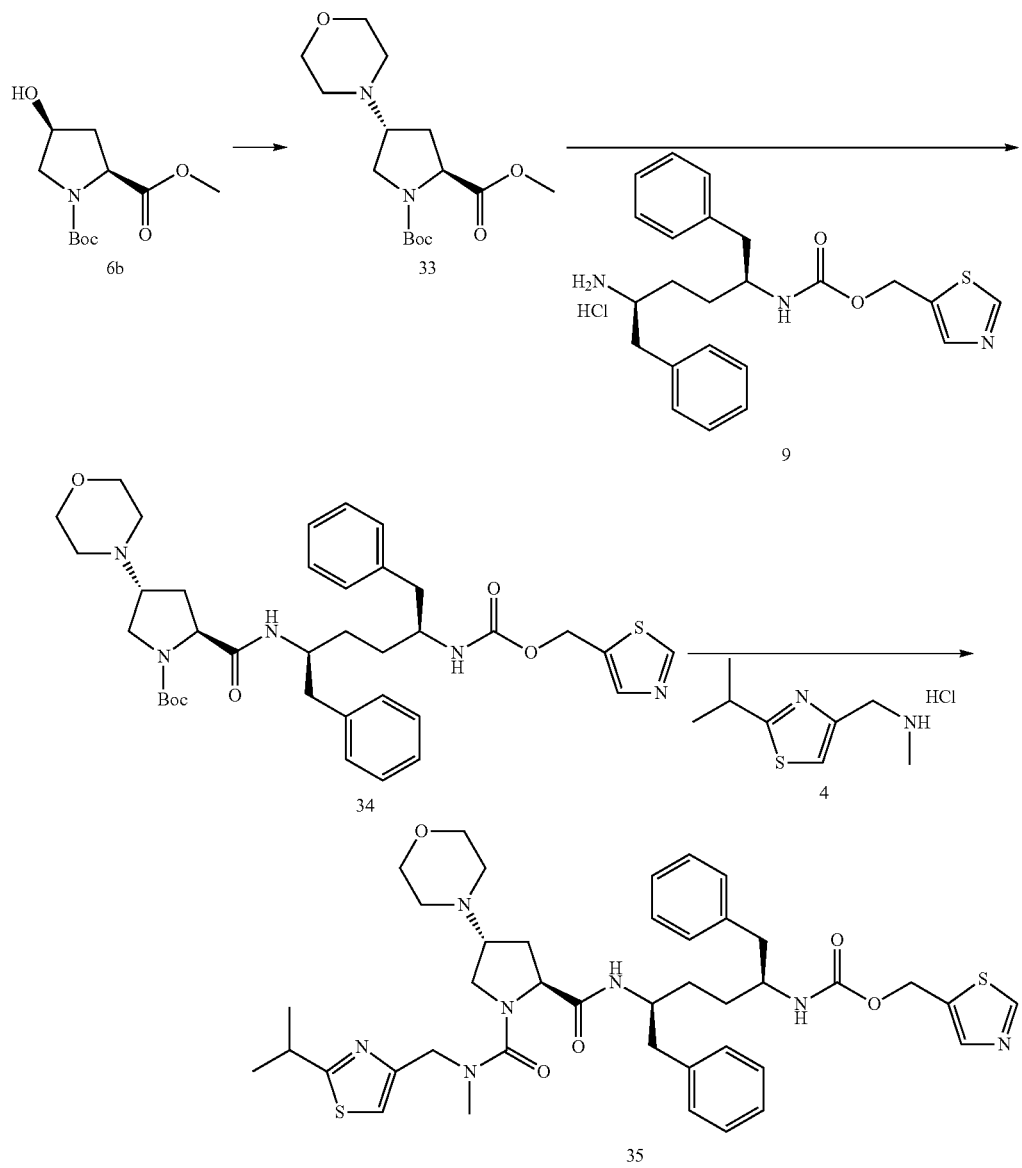

Preparation of Compound 35: To a solution of (2S,4R)-tert-butyl 2-(((2S,5S)-1,6-diphenyl-5-((thiazol-5-yl-methoxy)carbonyl)hexan-2-yl)carbamoyl)-4-morpholinopyrrolidine-1-carboxylate compound 34 (444 mg, 0.64 mmol) dissolved in MeOH (5 mL) was added 4N HCl in dioxane (5 mL). The mixture was stirred for 2 hr and concentrated under reduced pressure. It was then diluted with EtOAc and washed with saturated aqueous sodium bicarbonate solution and then saturated sodium chloride solution. The organic extracts were dried over anhydrous sodium sulfate and concentrated under reduced pressure to give the corresponding Boc-deprotected amine, which was used for next step without purification.

Triphosgene (35 mg, 0.118 mmol) was dissolved in anhydrous DCM (2 mL) and stirred under N2 (g) at 0° C. The above amine (100 mg, 0.169 mmol) was dissolved in anhydrous DCM (2 mL) and DIPEA (30 µL, 0.169 mmol), and was added dropwise to the triphosgene solution and then stirred for 30 mins. Compound 4 (102 mg, 0.845 mmol) was dissolved in anhydrous DCM (2 mL) and DIPEA (150 µL, 0.85 mmol) and added to the reaction in one portion. The reaction was then warmed to room temperature and stirred for 16 hrs, concentrated under reduced pressure and then dissolved with EtOAc and washed with saturated aqueous sodium bicarbonate solution and then saturated sodium chloride solution. The organic extracts were dried over anhydrous sodium sulfate and concentrated under reduced pressure. The crude material was purified using silica gel column (0-5% MeOH in DCM) to give compound 35 (82 mg, 62%). $^1$H NMR (CD$_3$OD): δ 8.97 (s, 1H), 7.82 (s, 1H), 7.25-7.13 (m, 11H), 5.20 (s, 2H), 4.45 (s, 2H), 4.34 (m, 1H), 4.18 (m, 1H), 3.80-3.65 (m, 6H), 3.43 (m, 1H), 3.25 (m, 1H), 2.87-2.80 (m, 5H), 2.69-2.59 (m, 3H), 2.37 (m, 4H), 1.90 (m, 1H), 1.62-1.33 (m, 11H). Mass Spectrum (m/z): (M+H)$^+$ 788.3.

Preparation of Compound 34

Preparation of Compound 33: Boc-cis-4-hydroxy-L-Proline methyl ester compound 6b (490 mg, 2 mmol), which was available commercially, was dissolved in anhydrous DCM (5 mL) and stirred under N2 (g) at −50° C. Triflic anhydride (404 µL, 2.4 mmol) was added in one portion. TEA (445 µL, 3.2 mmol) was dissolved in anhydrous DCM (1 mL) and added to the reaction dropwise. The resulting mixture was stirred for 1 hr. Morpholine (348 µL, 4 mmol) was then added. Reaction was warmed to room temperature and stirred for 16 hrs. The resulting reaction mixture was concentrated under reduced pressure, dissolved in EtOAc and washed with saturated aqueous sodium bicarbonate solution and then saturated sodium chloride solution. The organic extracts were dried over anhydrous sodium sulfate and concentrated under reduced pressure. Purification of the crude material using silica gel column gave compound 33 (535 mg, 85%). $^1$H NMR (CDCl$_3$): δ 4.45-4.33 (m, 1H), 3.90-3.80 (m, 1H), 3.75 (s, 3H), 3.71 (m, 4H), 3.29 (m, 1H), 2.98 (m, 1H), 2.51-2.40 (m, 4H), 2.17-2.06 (M, 2H), 1.47 (m, 9H).

Preparation of Compound 34: To a solution of compound 33 (267 mg, 0.85 mmol) dissolved in dioxane (4 mL) and water (4 mL) was added 1N aqueous NaOH solution to give pH 13. The resulting mixture was stirred for 2 hrs, neutralized to pH 7 with aqueous HCl was concentrated under reduced pressure to give the corresponding acid. HOBt (130 mg, 0.85 mmol) and EDCI (196 mg, 1.02 mmol) was mixed in anhydrous DMF (5 mL), and stirred for 30 mins, compound 9 (417 mg, 0.935 mmol) and TEA (118 µL, 0.85 mmol) were added. The resulting mixture was stirred for 16 hrs, diluted with EtOAc and washed with saturated aqueous sodium bicarbonate solution and then saturated sodium chloride solution. The organic extracts were dried over anhydrous sodium sulfate and concentrated under reduced pressure. Purification of the crude material using silica gel column (0-5% MeOH in DCM) gave compound 34 (444 mg, 76%). $^1$H NMR (CD$_3$OD): δ 8.97 (s, 1H), 7.82 (s, 1H), 7.18-7.05 (m, 11H), 5.21 (s, 2H), 4.14 (m, 2H), 3.85 (m, 1H), 3.67 (m, 5H), 3.05 (m, 1H), 2.85-2.56 (m, 6H), 2.34 (m, 4H), 1.81 (m, 1H), 1.61-1.37 (m, 16H).

Mass Spectrum (m/z): (M+H)$^+$ 692.1.

Example 11

Preparation of Compound 36

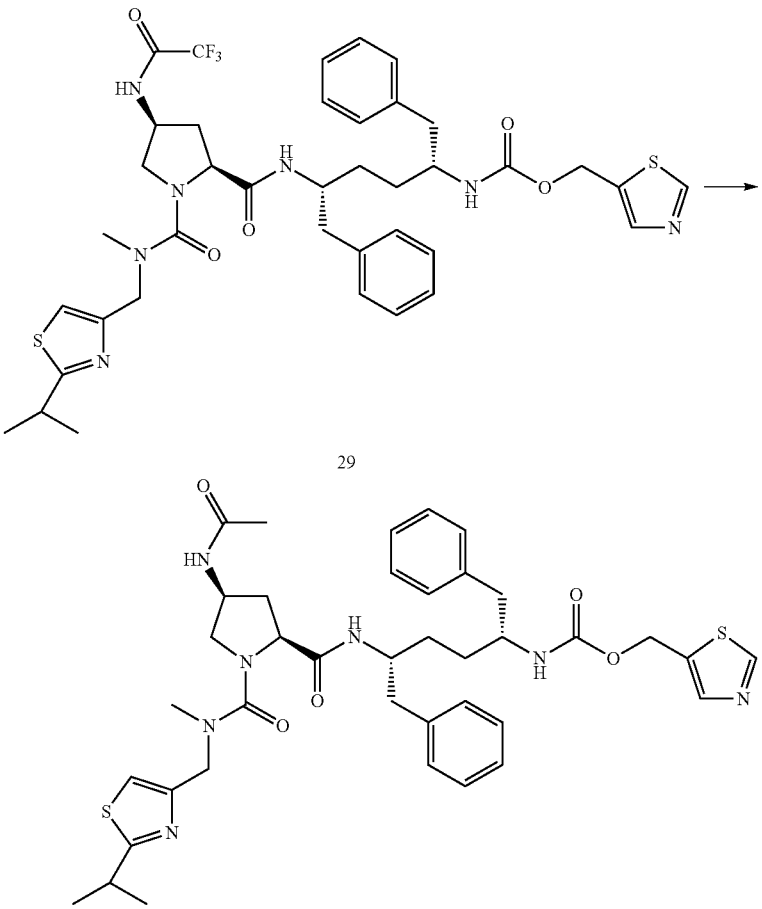

A solution of HOAc (4.1 µL, 0.072 mmol), HOBt (11 mg, 0.072 mmol) and EDCI (13.8 mg, 0.072 mmol) dissolved in anhydrous DMF was stirred for 40 mins. Compound 29 (43 mg, 0.06 mmol) was dissolved in anhydrous DMF and added to the above mixture along with TEA (25 µL, 0.18 mmol). The resulting mixture was stirred for 3 hrs, diluted with EtOAc and washed with saturated aqueous sodium bicarbonate solution and then saturated sodium chloride solution. The organic extracts were dried over anhydrous sodium sulfate and concentrated under reduced pressure. Purification of the material using silica gel column (0-10% MeOH in DCM gave compound 36 (25 mg, 55%). $^1$H NMR (CD$_3$OD): δ 8.98 (s, 1H), 7.83 (s, 1H), 7.71 (m, 1H), 7.25-7.13 (m, 11H), 6.82 (m, 1H), 5.21 (s, 2H), 4.56-4.36 (m, 3H), 4.25 (m, 1H), 4.09 (m, 1H), 3.78 (m, 2H), 3.32-3.20 (m, 4H), 2.84-2.68 (m, 7H), 2.37 (m, 1H), 1.95 (s, 3H), 1.63-1.43 (m, 5H), 1.38 (d, J=6.9 Hz, 6H). Mass Spectrum (m/z): (M+H)$^+$ 760.2.

Example 12

Preparation of Compound 39

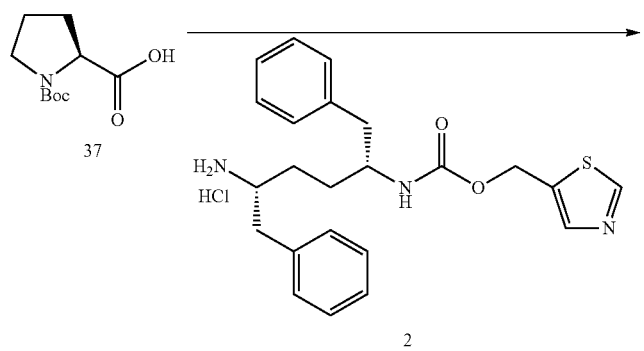

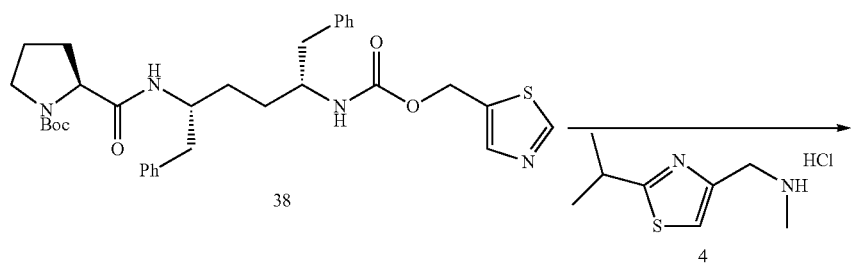

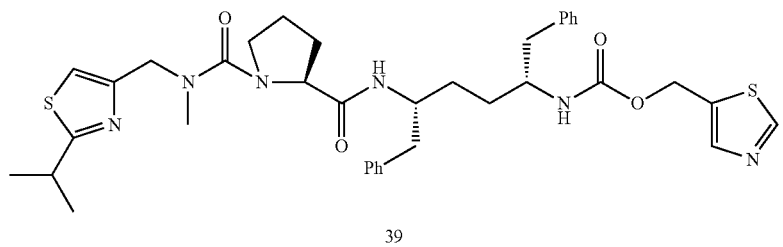

Compound 39 was prepared using the similar procedure for the preparation of compound 8, except that compound 7 was replaced with compound 38. Concentration and purification by flash chromatography (0-10% iPrOH in dichloromethane) gave compound 39 (90 mg). m/z: 703.1 (M+H)$^+$. $^1$H NMR (CD$_3$OD) δ 8.98 (1H, s), 7.82 (1H, s), 7.30-7.02 (11H, m), 5.21 (2H, s), 4.4-4.3 (3H, m), 4.05 (1H, m), 3.75 (1H, m), 3.40-3.25 (3H, m), 2.84 (3H, s), 2.8-2.6 (4H, m), 2.1-1.6 (4H, m), 1.6-1.4 (4H, m), 1.37 (6H, d, J=6.7 Hz).

Preparation of Compound 38

Compound 38 (570 mg) was prepared following the procedure used to prepare compound 7, except that compound 37 was used instead of compound 6. m/z: 607.0 (M+H)$^+$.

Example 13
Preparation of Compound 42
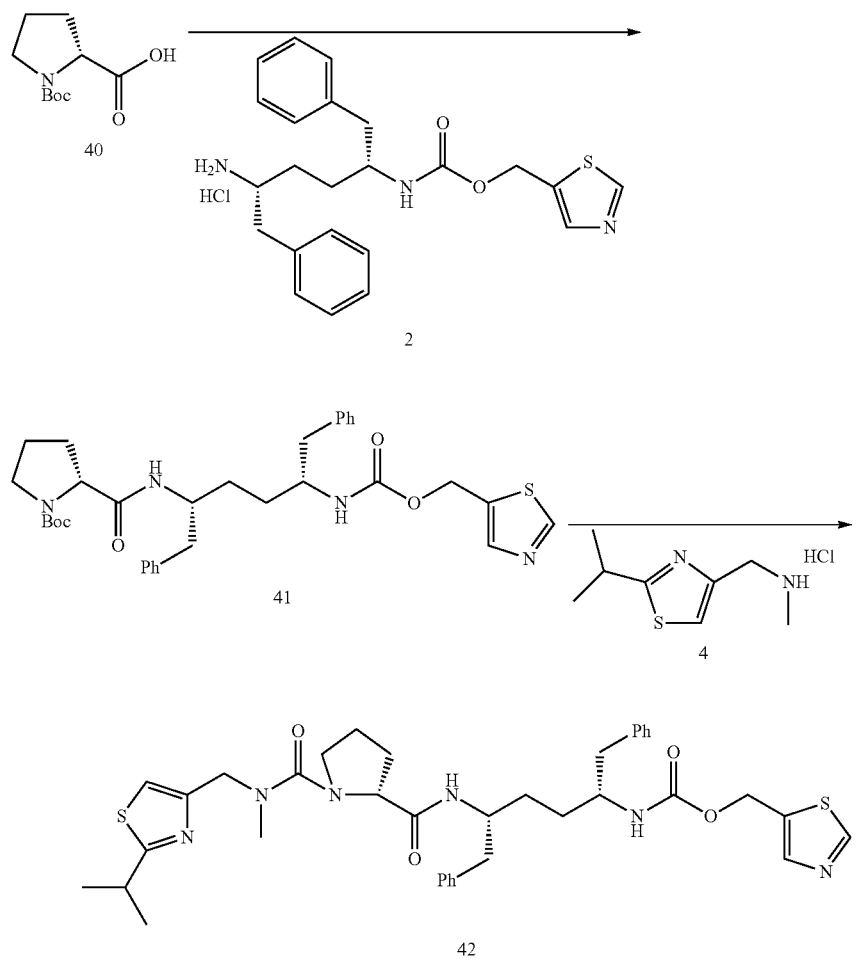
Compound 42 was prepared following the procedure for preparation of compound 39 except that compound 40 was used instead of compound 37. m/z: 703.1 (M+H)$^+$. $^1$H NMR (CD$_3$OD) δ 8.97 (1H, s), 7.81 (1H, s), 7.22-7.05 (11H, m), 5.20 (2H, s), 4.45 (2H, m), 4.3-4.1 (2H, m), 3.78 (1H, m), 3.46 (2H, m), 3.25 (1H, m), 2.88 (3H, s), 2.8-2.5 (4H, m), 2.0-1.4 (8H, m), 1.34 (6H, m).
Example 13
Preparation of Compound 49
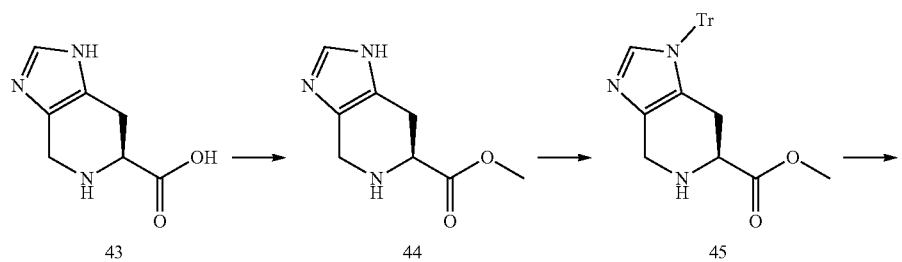

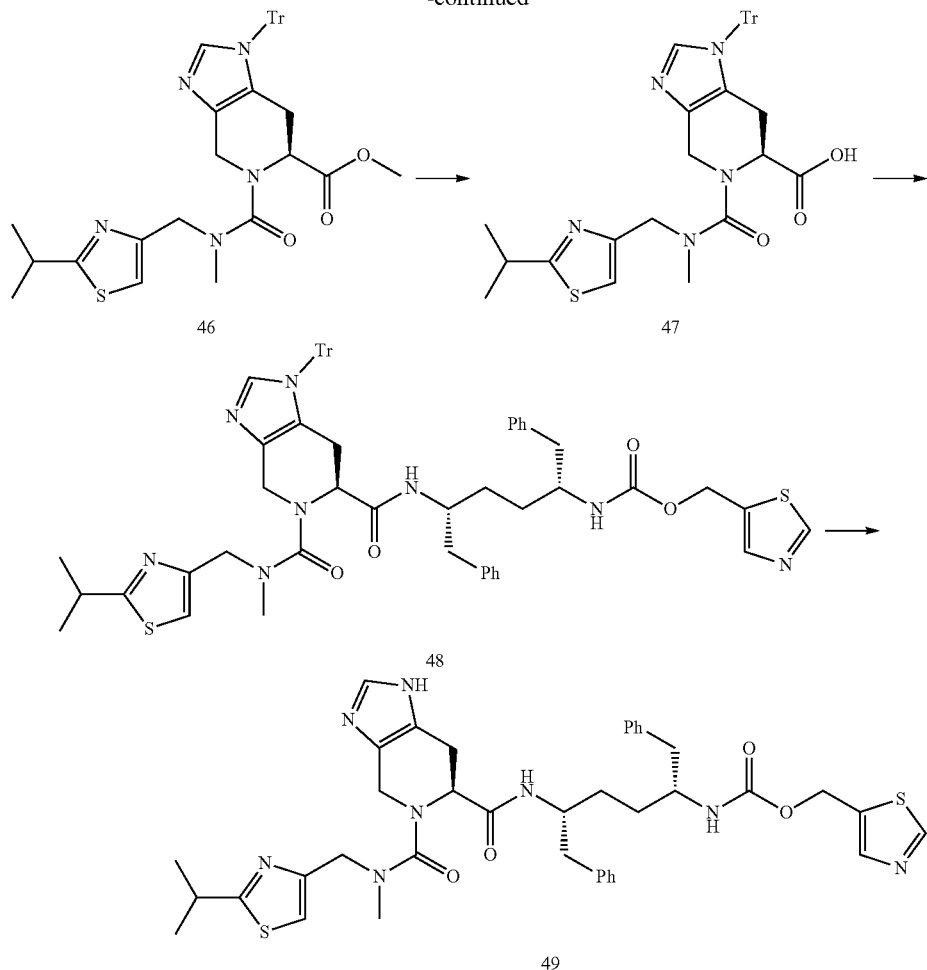

A mixture of compound 48 (20 mg, 0.02 mmol) and trifluoroacetic acid (0.5 mL, excess) was stirred at ambient temperature overnight, quenched with sodium bicarbonate solution. The mixture was extracted with ethyl acetate (3×10 mL) and the organic layer was washed with water and dried over Na$_2$SO$_4$. After filtration, the filtrate was concentrated under reduced pressure. The crude material was purified by column chromatography to give compound 49 (13 mg, 86%). $^1$H-NMR (300 MHz, CD$_3$OD) δ8.99 (s, 1H), 8.70 (s, 1H), 7.90-7.80 (m, 2H), 7.35 (s, 1H), 7.33-7.00 (m, 10H), 5.22 (s, 2H), 4.85-4.75 (m, 1H), 4.45-4.06 (m, 4H), 3.98-3.80 (m, 1H), 3.40-3.22 (m, 1H), 3.00-2.80 (m, 3H), 2.78-2.60 (m, 5H), 2.60-2.40 (m, 1H), 1.70-1.35 (m, 10H); m/z 755.1 (M+H)$^+$.

Preparation of Compound 48

Preparation of Compound 44: Compound 44 was prepared following the procedure used to make compound 94 in WO 2008/103949, except that compound 43, which was obtained from Chem-Impex., was used instead of compound 93 in WO 2008/103949. m/z 181.9 (M+H)$^+$.

Preparation of Compound 45: To the stirred solution of Compound 44 (650 mg, 2.6 mmol) and triethylamine (1.43 mL, 10.2 mmol) in dichloromethane (30 mL) was added a solution of trityl chloride (1570 mg, 5.6 mmol) in dichloromethane at 0° C. The mixture was stirred for 16 hours, quenched with addition of water. The organic layer was separated, dried over Na$_2$SO$_4$, and filtered. The filtrate was concentrated under vacuum. The obtained residue was dissolved into dichloromethane (20 mL), and trifluoroacetic acid (0.42 mL, 5.6 mmol) was added and stirred at 0° C. for 1 minute. The mixture was poured into saturated sodium bicarbonate solution. The mixture was extracted with dichloromethane (3×30 mL). The combined organic layer was washed twice with water and once with brine, and dried over Na$_2$SO$_4$. Concentration and purification by column chromatography to give the desired compound 45 (360 mg). $^1$H-NMR (300 MHz, CD$_3$OD) δ 7.45-7.35 (m, 9H), 7.32 (s, 1H), 7.20-7.10 (m, 6H), 4.00-3.76 (m, 2H), 3.61 (s, 3H), 3.56-3.48 (m, 1H), 2.00-1.80 (m, 2H).

Preparation of Compound 46: To a stirred solution of compound 45 (50 mg, 0.12 mmol) and triethylamine (0.02 mL, 0.14 mmol) in dichloromethane (2 ML) was added slowly a solution of phosgene in toluene (0.07 mL 20% in toluene, 0.13 mmol) at 0° C. The mixture was stirred at 0° C. for 1 hour. A solution of compound 4 (80 mg, 0.5 mmol) and triethylamine (0.02 mL, 0.14 mmol) in dichloromethane was added to the mixture in one pot. The mixture was stirred for another 3 hours before quenched with sodium bicarbonate solution. The mixture was extracted with dichloromethane (3×20 mL) and the organic layer was washed with water and dried over Na$_2$SO$_4$. After filtration, the filtrate was concentrated under vacuum. The obtained residue was purified by column chromatography to give the desired compound 46 (28 mg). m/z 619.8 (M+H)$^+$.

Preparation of Compound 47: Compound 47 was prepared following the procedure used to prepare compound 7, except that compound 46 was used instead of compound 6.

Preparation of Compound 48: Compound 48 was prepared following the procedure used in EXAMPLE C in WO 2008/103949, except that compound 47 was used instead of compound 7 in WO 2008/103949.

$IC_{50}$ Determinations for Human Liver Cytochrome P450
Materials and General Methods Pooled (n≥15 donors) human hepatic microsomal fraction was obtained from BD-Gentest (Woburn, Mass.) who also supplied hydroxy-terfenadine, 4'-hydroxydiclofenac and NADPH regenerating system. Ritonavir was prepared from commercial Norvir® oral solution (Abbott Laboratories, Abbott Park, Ill.). Other reagents were from Sigma-Aldrich (St. Louis, Mo.) and included terfenadine, fexofenadine, BRL 15572, diclofenac and mefenamic acid.

Incubations were performed in duplicate in 50 mM potassium phosphate buffer, pH 7.4 with NADPH regenerating system used as described by the manufacturer. The final microsomal protein concentrations had previously been determined to be within the linear range for activity and resulted in less than 20% consumption of substrate over the course of the incubation. The final substrate concentrations used were equal to the apparent Km values for the activities determined under the same conditions. Inhibitors were dissolved in DMSO, and the final concentration of DMSO, from both substrate and inhibitor vehicles, was 1% (v/v). Incubations were performed at 37° C. with shaking and were initiated by addition of substrate. Aliquots were then removed at 0.7 and 15 minutes. Samples were quenched by treatment with an acetonitrile, formic acid, water (94.8%/0.2%/5%, v/v/v) mixture containing internal standard. Precipitated protein was removed by centrifugation at 3000 rpm for 10 mM and aliquots of the supernatant were then subjected to LC-MS analysis.

The LC-MS system consisted of a Waters Acquity UPLC, with a binary solvent manager and a refrigerated (8° C.) sample organizer and sample manager, interfaced to a Micromass Quattro Premier tandem mass spectrometer operating in electrospray ionization mode. The column was a Waters Acquity UPLC BEH $C_{18}$ 2.1×50 mm, 1.7 inn pore size. Mobile phases consisted of mixtures of acetonitrile, formic acid and water, the composition for mobile phase A being 1%/0.2%/98.8% (v/v/v) and that for mobile phase B being 94.8%/0.2%/5% (v/v/v). The injection volumes were 5 µL and the flow rate was 0.8 mL/min. Concentrations of metabolites were determined by reference to standard curves generated with authentic analytes under the same conditions as the incubations.

$IC_{50}$ values (the concentration of inhibitor reducing CYP3A activity by 50%) were calculated by non-linear regression using GraphPad Prism 4.0 software and a sigmoidal model.

CYP3A Inhibition Assay

The potencies of the compounds as inhibitors of human hepatic cytochromes P450 of the CYP3A subfamily (particularly CYP3A4) were assessed using well-characterized selective activities: midazolam 1'-hydroxylase (Kronbach, T., et al. *Mol. Pharmacol.* 36, 89-96 [1989]) and testosterone 6β-hydroxylase (Waxman, D. J., et al. *Arch. Biochem. Biophys.* 263, 424-436, [1988]). For midazolam hydroxylase determination the final concentrations of microsomal protein and terfenadine substrate were 0.25 mg/mL and 2.5 µM, respectively, and the LC-MS internal standard was 1α-hydroxytriazolam. For testosterone hydroxylase activity the final microsomal protein concentration was 0.5 mg/mL, the substrate concentration was 50 µM and the LC-MS internal standard was $D_7$-labeled 6β-hydroxytestosterone. After incubation at 37° C. for 5 minutes, metabolic reactions were terminated by treatment with quench solution containing the appropriate internal standard and were subsequently centrifuged before aliquots of the supernatant were removed and diluted with 0.1% (v/v) formic acid for LC-MS analysis.

For LC-MS analysis the column was a Phenomenex Synergi Max RP 4 µm column (50×2.0 mm) and the injection volume was 5 µL. The MS/MS ion current metabolite/internal standard peak area ratios (PAR) were measured on an Applied Biosystems SciEx API4000 triple quadrupole mass spectrometer coupled to a Leap CTC PAL autosampler with a 20 µL loop and a Shimadzu LC pump with a 25 µL mixer. The initial mobile phase consisted of 94.9% water, 0.1% formic acid, and 5% acetonitrile (v/v/v) pumped at 0.5 mL/min. After 0.5 min the acetonitrile concentration was increased to 30% over 0.5 min. The acetonitrile concentration was then further increased to 100% over 0.5 min and held for 1.3 min, after which the column was re equilibrated at the initial conditions for 1.2 min. Rates of metabolite formation were determined from standard curves using PAR determined with authentic metabolite standards.

Experimental data based on representative Examples demonstrate that the compounds of formula I of the present invention have CYP3A4 inhibition activity in a range represented by an $IC_{50}$ from <100 nM to about 370 nM. Table I shows the activity of representative examples of the compounds of the invention for inhibition of CYP3A4.

CYP2C9 Inhibition Assay

The potencies of the compounds as inhibitors of human hepatic CYP2C9 were assessed using tolbutamide-4-hydroxylase as a well-characterized selective activity (Miners, J. O., et al. *Biochem. Pharmacol.* 37, 1137-1144 [1988]). The final concentrations of microsomal protein and tolbutamide substrate were 1.0 mg/mL and 120 µM, respectively and reactions were initiated by the addition of NADPH to 1 mM. Sulfaphenazole, a positive control CYP2C9 inhibitor was tested in parallel. After incubation at 37° C. for 60 minutes, metabolic reactions were terminated by treatment with quench solution and were subsequently centrifuged before aliquots of the supernatant were removed and diluted with 0.1% (v/v) formic acid for LC-MS analysis.

For LC-MS analysis the column was a Phenomenex Synergi Max RP 4 µm column (50×2.0 mm) and the injection volume was 5 µL. The MS/MS ion current metabolite/internal standard peak area ratios (PAR) were measured on an Applied Biosystems SciEx API4000 triple quadrupole mass spectrometer coupled to a Leap CTC PAL autosampler with a 20 µL loop and a Shimadzu LC pump with a 25 µL mixer. The initial mobile phase consisted of 94.9% water, 0.1% formic acid, and 5% acetonitrile (v/v/v) pumped at 0.5 mL/min. After 0.5 min the acetonitrile concentration was increased to 30% over 0.5 min. The acetonitrile concentration was then further increased to 100% over 0.5 min and held for 1.3 min, after which the column was re equilibrated at the initial conditions for 1.2 min. Rates of metabolite formation were determined from standard curves using PAR determined with authentic 4-hydroxytolbutamide metabolite standard.

Representative examples demonstrate that the compounds of formula I of the present invention have CYP2C9 inhibition activity in a range represented by an $IC_{50}$ from about 3.5 µM to >25 µM.

The following biological assays were used for characterizing representative compounds of the invention.

HIV-1 Protease Enzyme Assay (Ki)

The assay is based on the fluorimetric detection of synthetic hexapeptide substrate cleavage by HIV-1 protease in a defined reaction buffer as initially described by M. V. Toth and G. R. Marshall, *Int. J. Peptide Protein Res.* 36, 544 (1990) (herein incorporated by reference in its entirety for all purposes).

The assay employed (2-aminobenzoyl)Thr-Ile-Nle-(p-nitro)Phe-Gln-Arg as the substrate and recombinant HIV-1 protease expressed in *E. Coli* as the enzyme. Both of the reagents were supplied by Bachem California, Inc. (Torrance, Calif.; Cat. no. H-2992). The buffer for this reaction was 100 mM ammonium acetate, pH 5.3, 1 M sodium chloride, 1 mM ethylendiaminetetraacetic acid, 1 mM dithiothreitol, and 10% dimethylsulfoxide.

To determine the inhibition constant Ki, a series of solutions were prepared containing identical amount of the enzyme (1 to 2.5 nM) and the inhibitor to be tested at different concentrations in the reaction buffer. The solutions were subsequently transferred into a white 96-well plate (190 µl each) and pre-incubated for 15 min at 37° C. The substrate was solubilized in 100% dimethylsulfoxide at a concentration of 800 µM and 10 µl of 800 µM substrate was added into each well to reach a final substrate concentration of 40 µM. The real-time reaction kinetics was measured at 37° C. using a Gemini 96-well plate fluorimeter (Molecular Devices, Sunnyvale, Calif.) at $\lambda(Ex)=330$ nm and $\lambda(Em)=420$ nm. Initial velocities of the reactions with different inhibitor concentrations were determined and the Ki value (in picomolar concentration units) was calculated by using EnzFitter program (Biosoft, Cambridge, U.K.) according to an algorithm for tight-binding competitive inhibition described by Ermolieff J., Lin X., and Tang J., Biochemistry 36, 12364 (1997).

HIV-1 Protease Enzyme Assay (IC50)

As for the $K_i$ assay, above, the $IC_{50}$ assay is based on the fluorimetric detection of synthetic hexapeptide substrate cleavage by HIV-1 protease in a defined reaction buffer as initially described by M. V. Toth and G. R. Marshall, *Int. J. Peptide Protein Res.* 36, 544 (1990).

The assay employed (2-aminobenzoyl)Thr-Ile-Nle-(p-nitro)Phe-Gln-Arg as the substrate and recombinant HIV-1 protease expressed in *E. Coli* as the enzyme. Both of the reagents were supplied by Bachem California, Inc. (Torrance, Calif.; Cat. nos. H-2992 and H-9040, respectively). The buffer for this reaction was 100 mM ammonium acetate, pH 5.5, 1 M sodium chloride, 1 mM ethylendiaminetetraacetic acid, and 1 mM dithiothreitol, and 10% dimethylsulfoxide.

To determine the IC50 value, 170 µL of reaction buffer was transferred into the wells of a white 96-well microtiter plate. A series of 3-fold dilutions in DMSO of the inhibitor to be tested was prepared, and 10 µL of the resulting dilutions was transferred into the wells of the microtiter plate. 10 µL of a 20-50 nM enzyme stock solution in reaction buffer was added to each well of the 96-well plate to provide a final enzyme concentration of 1-2.5 nM. The plates were then preincubated for 10 minutes at 37° C. The substrate was dissolved in 100% dimethylsulfoxide at a concentration of 400 µM and 10 µl of the 400 µM substrate was added into each well to reach a final substrate concentration of 20 µM. The real-time reaction kinetics were measured using a Gemini 96-well plate fluorimeter (Molecular Devices, Sunnyvale, Calif.) at $\lambda(Ex)=330$ nm and $\lambda(Em)=420$ nm. Initial velocities of the reactions with different inhibitor concentrations were determined and the $IC_{50}$ value (in nanomolar concentration units) was calculated by using GraphPad Prism™ software to fit nonlinear regression curves.

Anti-HIV-1 Cell Culture Assay (EC50)

The assay is based on quantification of the HIV-1-associated cytopathic effect by a colorimetric detection of the viability of virus-infected cells in the presence or absence of tested inhibitors. HIV-1-induced cell death was determined using a metabolic substrate 2,3-bis(2-methoxy-4-nitro-5-sulfophenyl)-2H-tetrazolium-5-carboxanilide (XTT) which is converted only by intact cells into a product with specific absorption characteristics as described by Weislow O S, Kiser R, Fine D L, Bader J, Shoemaker R H and Boyd M R, *J. Natl. Cancer Inst.* 81, 577 (1989) (herein incorporated by reference in its entirety for all purposes).

MT2 cells (NIH AIDS reagent program, Cat #237) maintained in RPMI-1640 medium supplemented with 5% fetal bovine serum and antibiotics were infected with the wild-type HIV-1 strain IIIB (Advanced Biotechnologies, Columbia, Md.) for 3 hours at 37° C. using the virus inoculum corresponding to a multiplicity of infection equal to 0.01. The infected cells in culture media were distributed into a 96-well plate (20,000 cells in 100 µl/well), and incubated in the presence of a set of solutions containing 5-fold serial dilutions of the tested inhibitor (100 µl/well) for 5 days at 37° C. Samples with untreated infected and untreated mock-infected control cells were also distributed to the 96-well plate and incubated under the same conditions.

To determine the antiviral activity of the tested inhibitors, a substrate XTT solution (6 mL per assay plate) at a concentration of 2 mg/mL in a phosphate-buffered saline pH 7.4 was heated in water-bath for 5 min at 55° C. before 50 µl of N-methylphenazonium methasulfate (5 µg/mL) was added per 6 mL of XTT solution. After removing 100 µl media from each well on the assay plate, 100 µl of the XTT substrate solution was added to each well. The cells and the XTT solution were incubated at 37° C. for 45 to 60 min in a $CO_2$ incubator. To inactivate the virus, 20 µl of 2% Triton X-100 was added to each well. Viability, as determined by the amount of XTT metabolites produced, was quantified spectrophotometrically by the absorbance at 450 nm (with subtraction of the background absorbance at 650 nm). Data from the assay was expressed as the percentage absorbance relative to untreated control and the fifty percent effective concentration ($EC_{50}$) was calculated as the concentration of compound that effected an increase in the percentage of XTT metabolite production in infected, compound treated cells to 50% of that produced by uninfected, compound-free cells.

Anti-HIV-1 Cell Culture Assay ($EC_{50}$) in Presence of 40% Human Serum or Human Serum Proteins This assay is almost identical to the Anti-HIV-1 Cell Culture Assay described above, except that the infection was made in the presence or absence of 40% human serum (Type AB Male Cambrex 14-498E) or human serum proteins (Human α-acid Glycoprotein, Sigma G-9885; Human Serum Albumin, Sigma A1653, 96-99%) at physiological concentration. The HIV-1-induced cell death was determined as described above, except that the infected cells distributed in the 96-well plate were incubated in 80% Human Serum (2× concentration) or in 2 mg/mL Human α-acid Glycoprotein+ 70 mg/mL HSA (2× concentration) rather than in culture media.

Cytotoxicity Cell Culture Assay ($CC_{50}$)

The assay is based on the evaluation of cytotoxic effect of tested compounds using a metabolic substrate 2,3-bis(2-methoxy-4-nitro-5-sulfophenyl)-2H-tetrazolium-5-carboxanilide (XTT) as described by Weislow O S, Kiser R, Fine D L, Bader J, Shoemaker R H and Boyd M R, *J. Natl. Cancer Inst.* 81, 577 (1989). This assay is almost identical to the previous assay described (Anti-HIV-1 Cell Culture Assay), except that the cells were not infected. The compound induced cell death (or growth reduction) was determined as previously described.

MT-2 cells maintained in RPMI-1640 medium supplemented with 5% fetal bovine serum and antibiotics were distributed into a 96-well plate (20,000 cells in 100 µl/well) and incubated in the presence or absence of 5-fold serial dilutions of the tested inhibitor (100 µl/well) for 5 days at 37° C. Controls included untreated infected cells and infected cells protected by 1 µM of P4405 (Podophyllotoxin, Sigma Cat #P4405).

To determine cytotoxicity, an XTT solution (6 mL per assay plate) at a concentration of 2 mg/mL in phosphate-buffered saline pH 7.4 was heated in the dark in a water-bath for 5 min at 55° C. before 50 µl of N-methylphenazonium methasulfate (5 µg/mL) was added per 6 mL of XTT solution. After removing 100 µl media from each well on the assay plate, 100 µL of the XTT substrate solution was added to each well. The cells and the XTT solution were incubated at 37° C. for 45 to 60 min in a $CO_2$ incubator. To inactivate the virus, 20 µl of 2% Triton X-100 was added to each well. Viability, as determined by the amount of XTT metabolites produced, is quantified spectrophotometrically by the absorbance at 450 nm (with subtraction of the background absorbance at 650 nm). Data from the assay is expressed as the percentage absorbance relative to untreated control, and the fifty percent cytotoxicity concentration ($EC_{50}$) was calculated as the concentration of compound that affected an increase in the percentage of cell growth in compound treated cells to 50% of the cell growth provided by uninfected, compound-free cells.

Experimental data based on representative Examples also demonstrate that the compounds of formula I of the present invention have a protease inhibition activity as represented by HIV $EC_{50}$ of greater than 2 µM.

TABLE I

Activity against CYP3A4
Activity of representative compounds of the invention against CYP3A4

| Compound number | CYP3A4 $IC_{50}$ (µM) (midazolam) | CYP3A4 $IC_{50}$ (µM) (testosterone) |
|---|---|---|
| 5 | 0.16 | 0.23 |
| 8 | 0.17 | 0.24 |
| 11 | 0.12 | 0.30 |
| 16 | 0.20 | 0.30 |
| 18 | 0.16 | 0.26 |
| 21 | 0.19 | 0.34 |
| 24 | 0.15 | 0.34 |
| 25 | 0.14 | 0.30 |
| 29 | 0.19 | 0.31 |
| 30 | 0.17 | 0.36 |
| 31 | 0.15 | 0.33 |
| 32 | 0.12 | 0.35 |
| 35 | <0.1 | 0.15 |
| 36 | <0.1 | 0.37 |
| 39 | 0.13 | 0.26 |
| 42 | 0.11 | 0.25 |
| 49 | 0.19 | 0.37 |

What is claimed is:
1. A compound of formula I:

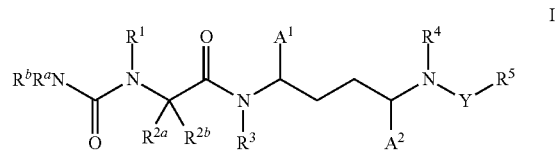

wherein:
$A^1$ is $(C_1$-$C_6)$alkyl, aryl$(C_1$-$C_6)$alkyl, heteroaryl$(C_1$-$C_6)$alkyl, $(C_3$-$C_6)$carbocyclyl$(C_1$-$C_6)$alkyl or heterocyclyl$(C_1$-$C_6)$alkyl, wherein any $(C_1$-$C_6)$alkyl of $A^1$ is optionally substituted with one or more $Z^2$ groups and wherein any aryl$(C_1$-$C_6)$alkyl, heteroaryl$(C_1$-$C_6)$alkyl, $(C_3$-$C_6)$carbocyclyl$(C_1$-$C_6)$alkyl or heterocyclyl$(C_1$-$C_6)$alkyl of $A^1$ is optionally substituted with one or more $Z^3$ groups;

$A^2$ is $(C_1$-$C_6)$alkyl, aryl$(C_1$-$C_6)$alkyl, heteroaryl$(C_1$-$C_6)$alkyl, $(C_3$-$C_6)$carbocyclyl$(C_1$-$C_6)$alkyl or heterocyclyl$(C_1$-$C_6)$alkyl, wherein any $(C_1$-$C_6)$alkyl of $A^2$ is optionally substituted with one or more $Z^2$ groups, and wherein any aryl$(C_1$-$C_6)$alkyl, heteroaryl$(C_1$-$C_6)$alkyl, $(C_3$-$C_6)$carbocyclyl$(C_1$-$C_6)$alkyl or heterocyclyl$(C_1$-$C_6)$alkyl of $A^2$ is optionally substituted with one or more $Z^3$ groups;

Y is —C(O)O— or —C(O)$NR^c$—;

$R^1$ is H or $(C_1$-$C_6)$alkyl, and $R^{2a}$ and $R^{2b}$ taken together with the carbon to which they are attached form a heterocyclyl or a carbocyclyl; or $R^{2b}$ is H, and $R^{2a}$ and $R^1$ taken together with the atoms to which they are attached form a heterocyclyl, wherein any heterocyclyl or carbocyclyl of $R^{2a}$ and $R^{2b}$ or $R^{2a}$ and $R^1$ is optionally substituted with one or more $Z^1$ groups;

$R^3$ is H or $(C_1$-$C_6)$alkyl;

$R^4$ is H or $(C_1$-$C_6)$alkyl;

$R^5$ is aryl, aryl$(C_1$-$C_6)$alkyl, heteroaryl, heteroaryl$(C_1$-$C_6)$alkyl, heterocyclyl or heterocyclyl$(C_1$-$C_6)$alkyl, wherein any aryl, aryl$(C_1$-$C_6)$alkyl, heteroaryl, heteroaryl$(C_1$-$C_6)$alkyl, heterocyclyl or heterocyclyl$(C_1$-$C_6)$alkyl of $R^4$ is optionally substituted with one or more $Z^4$ groups;

$R^a$ is H or $(C_1$-$C_6)$alkyl;

$R^b$ is heteroaryl$(C_1$-$C_6)$alkyl optionally substituted with one or more $Z^5$ groups;

$R^c$ is H or $(C_1$-$C_6)$alkyl;

each $R^d$ and $R^e$ is independently selected from H and $(C_1$-$C_6)$alkyl;

$R^f$ is H or $(C_1$-$C_6)$alkyl;

$R^g$ is $(C_1$-$C_6)$alkyl;

each $Z^1$ is independently selected from halogen, OH, —$CF_3$, —$OCF_3$, oxo, CN, $(C_1$-$C_6)$alkyl, —O$(C_1$-$C_6)$alkyl, —S$(C_1$-$C_6)$alkyl, —SO$(C_1$-$C_6)$alkyl, —$SO_2$ $(C_1$-$C_6)$alkyl, —$NR^dR^e$, —$NR^fC(O)R^g$, —$NR^fS(O)_2R^g$, heterocyclyl and heteroaryl;

each $Z^2$ is independently selected from OH, oxo, halogen, —$OCF_3$, CN, —O$(C_1$-$C_6)$alkyl, —S$(C_1$-$C_6)$alkyl, —SO$(C_1$-$C_6)$alkyl, —$SO_2$ $(C_1$-$C_6)$alkyl, —$NR^dR^e$, —$NR^fC(O)R^g$ and —$NR^fS(O)_2R^g$;

each $Z^3$ is independently selected from OH, oxo, halogen, —$CF_3$, —$OCF_3$, —$NO_2$, CN, $(C_1$-$C_6)$alkyl, —O$(C_1$-$C_6)$alkyl, —S$(C_1$-$C_6)$alkyl, —SO$(C_1$-$C_6)$alkyl, —$SO_2$ $(C_1$-$C_6)$alkyl, —$NR^dR^e$, —$NR^fC(O)R^g$ and —$NR^fS(O)_2R^g$;

each $Z^4$ is independently selected from OH, oxo, halogen, —$CF_3$, —$OCF_3$, —$NO_2$, —CN, $(C_1$-$C_6)$alkyl, —O$(C_1$-$C_6)$alkyl, and —$NR^dR^e$; and each $Z^5$ is independently selected from OH, oxo, halogen, —CF$_3$, —OCF$_3$, —NO$_2$, —CN, (C$_1$-C$_6$)alkyl, —O(C$_1$-C$_6$)alkyl, and —NR$^d$R$^e$;
or a salt thereof.

2. The compound of claim 1, or a salt thereof, wherein R$^{2b}$ is H, and R$^{2a}$ and R$^1$ taken together with the atoms to which they are attached form a heterocyclyl, wherein any heterocyclyl of R$^{2a}$ and R$^1$ is optionally substituted with one or more Z$^1$ groups.

3. The compound of claim 1, or a salt thereof, wherein R$^1$ is H or (C$_1$-C$_6$)alkyl, and R$^{2a}$ and R$^{2b}$ taken together with the carbon to which they are attached form a heterocyclyl or a carbocyclyl, wherein any heterocyclyl or carbocyclyl of R$^{2a}$ and R$^{2b}$ is optionally substituted with one or more Z$^1$ groups.

4. The compound of claim 3, or a salt thereof, wherein R$^1$ is H.

5. The compound of claim 3, or a salt thereof, wherein R$^1$ is CH$_3$.

6. The compound of claim 3, or a salt thereof, wherein R$^{2a}$ and R$^{2b}$ taken together with the carbon to which they are attached form a heterocyclyl, wherein any heterocyclyl of R$^{2a}$ and R$^{2b}$ is optionally substituted with one or more Z$^1$ groups.

7. The compound of claim 1, or a salt thereof, wherein Z$^1$ is OH, (C$_1$-C$_6$)alkyl, —NR$^d$R$^e$, —NR$^f$C(O)R$^g$, or heterocyclyl.

8. The compound of claim 1, or a salt thereof, wherein R$^3$ is H.

9. The compound of claim 1, or a salt thereof, wherein R$^4$ is H.

10. The compound of claim 1, or a salt thereof, wherein Y is —C(O)O—.

11. The compound of claim 1, or a salt thereof, wherein R$^5$ is heteroaryl(C$_1$-C$_6$)alkyl, wherein any heteroaryl(C$_1$-C$_6$)alkyl of R$^5$ is optionally substituted with one or more Z$^4$ groups.

12. The compound of claim 1, or a salt thereof, wherein R$^a$ is (C$_1$-C$_6$)alkyl.

13. The compound of claim 1, or a salt thereof, wherein R$^b$ is heteroaryl-CH$_2$—, wherein any heteroaryl-CH$_2$— of R$^b$ is optionally substituted with one or more Z$^5$ groups.

14. The compound of claim 1, or a salt thereof, wherein A$^1$ and A$^2$ are each aryl(C$_1$-C$_6$)alkyl, wherein any aryl(C$_1$-C$_6$)alkyl of A$^1$ or A$^2$ is optionally substituted with one or more Z$^3$ groups.

15. The compound of claim 1, or a salt thereof, wherein A$^1$ and A$^2$ are each phenyl-CH$_2$—.

16. The compound of claim 1 which is:

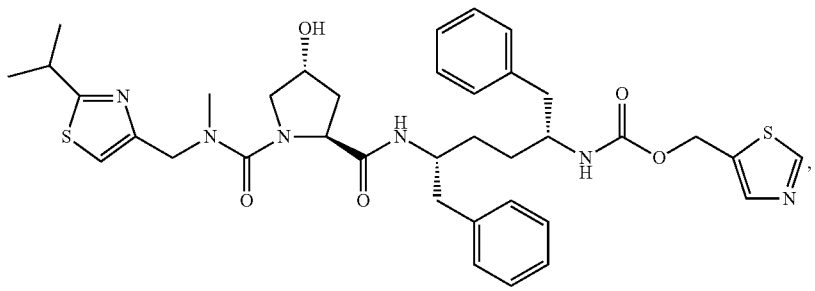

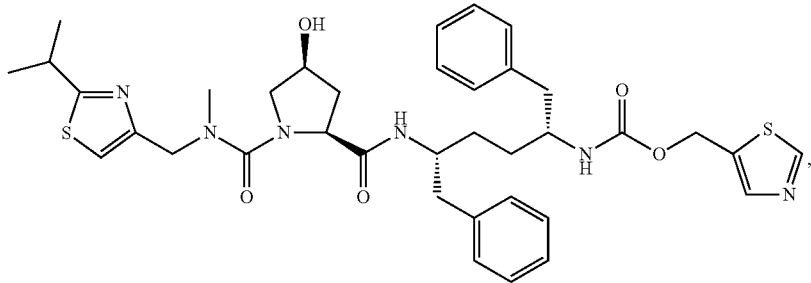

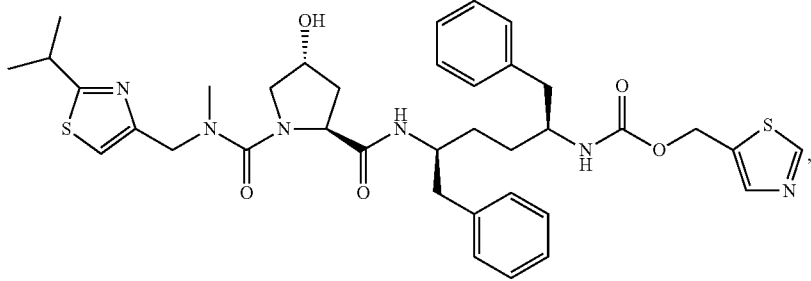

-continued
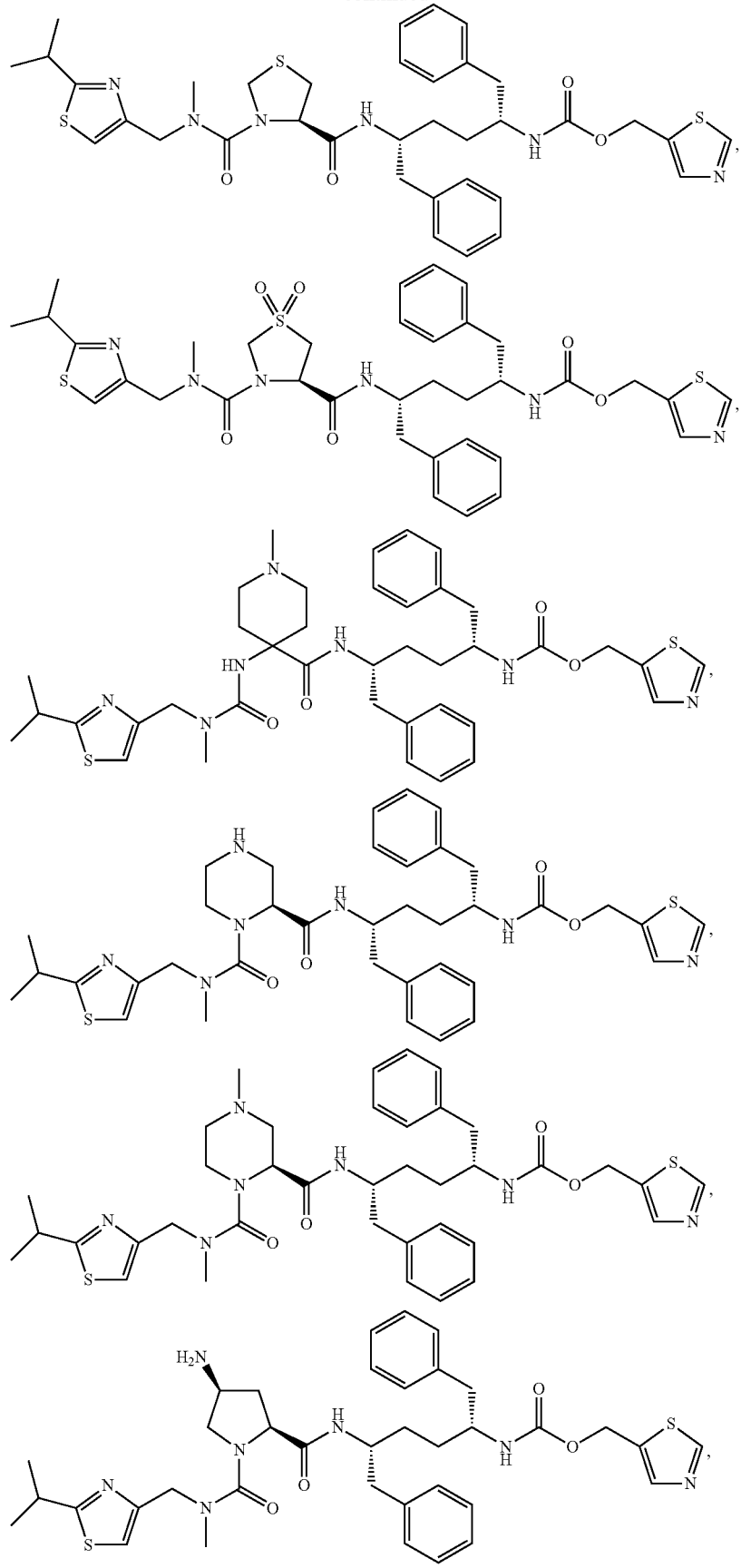

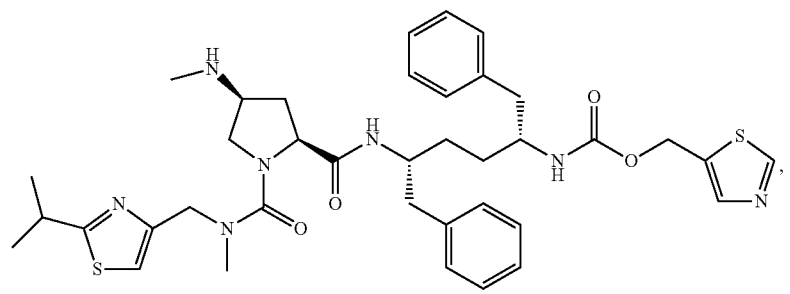,
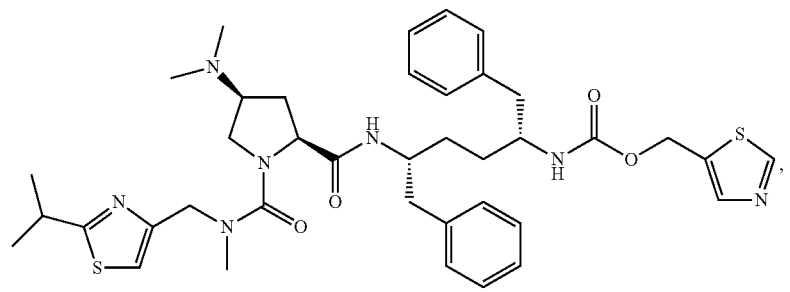,
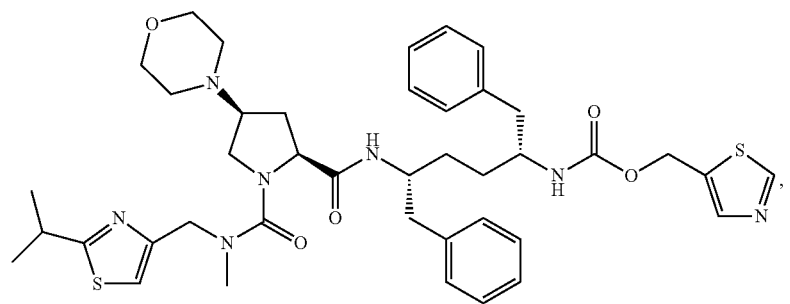,
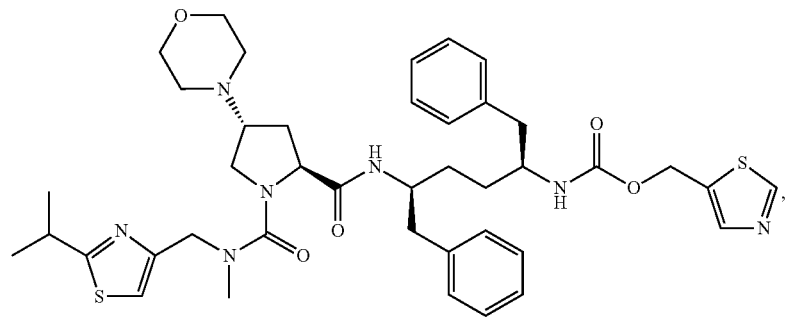,
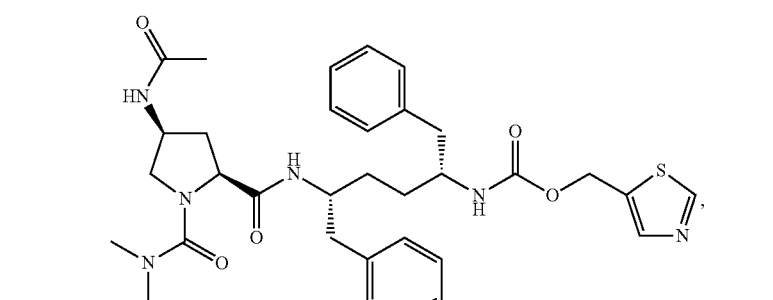
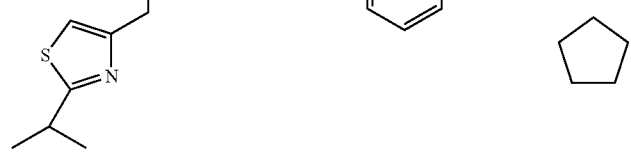

-continued

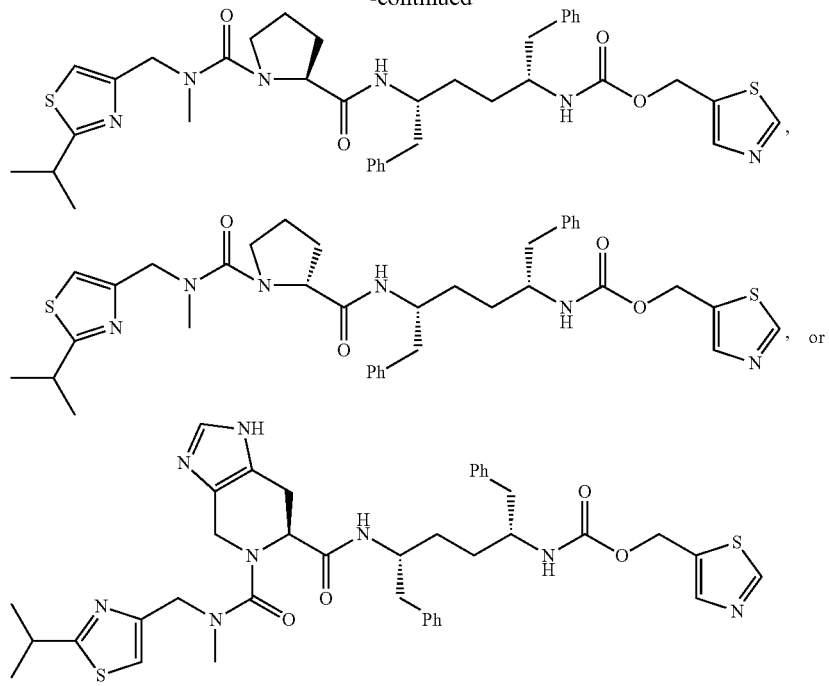

or a salt thereof.

17. A pharmaceutical composition comprising a compound of formula I of claim 1, or a pharmaceutically acceptable salt thereof, and a pharmaceutically acceptable carrier or excipient.

18. The pharmaceutical composition of claim 17, further comprising one or more therapeutic agents metabolized by cytochrome P450 monooxygenase.

19. The pharmaceutical composition of claim 18 wherein the therapeutic agents metabolized by cytochrome P450 are selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, interferons, ribavirin analogs, NS5b polymerase inhibitors, NS3 protease inhibitors, alpha-glucosidase 1 inhibitors, hepatoprotectants, non-nucleoside inhibitors of HCV and other drugs for treating HCV.

20. A method for improving the pharmacokinetics or increasing blood plasma levels of one or more therapeutic agents metabolized by cytochrome P450 monooxygenase, comprising co-administering to a patient treated with one or more therapeutic agents metabolized by cytochrome P450 monooxygenase, a pharmacokinetic improving or blood plasma level increasing effective amount of a compound of formula I as described in claim 1, or a pharmaceutically acceptable salt thereof.

* * * * *